United States Patent
Gellman et al.

(10) Patent No.: US 9,044,392 B2
(45) Date of Patent: Jun. 2, 2015

(54) NYLON-3 CO-POLYMERS AND SYNTHETIC LUNG SURFACTANT COMPOSITIONS CONTAINING SAME

(75) Inventors: Samuel H. Gellman, Madison, WI (US); Shannon S. Stahl, Madison, WI (US); Brendan P. Mowery, San Marcos, CA (US); Annelise Barron, Palo Alto, CA (US); Michelle Dohm, Palos Park, IL (US)

(73) Assignees: Wisconsin Alumni Research Foundation, Madison, WI (US); Northwestern University, Evanston, IL (US)

( * ) Notice: Subject to any disclaimer, the term of this patent is extended or adjusted under 35 U.S.C. 154(b) by 0 days.

(21) Appl. No.: 13/634,576

(22) PCT Filed: Mar. 17, 2011

(86) PCT No.: PCT/US2011/028813
§ 371 (c)(1),
(2), (4) Date: Sep. 13, 2012

(87) PCT Pub. No.: WO2011/116188
PCT Pub. Date: Sep. 22, 2011

(65) Prior Publication Data
US 2013/0004453 A1  Jan. 3, 2013

Related U.S. Application Data

(60) Provisional application No. 61/315,708, filed on Mar. 19, 2010.

(51) Int. Cl.
| | |
|---|---|
| C08G 69/22 | (2006.01) |
| A61K 31/785 | (2006.01) |
| A61P 11/00 | (2006.01) |
| C08G 69/48 | (2006.01) |
| A61K 9/00 | (2006.01) |
| A61K 47/32 | (2006.01) |
| C08L 77/02 | (2006.01) |

(52) U.S. Cl.
CPC .............. *A61K 9/0082* (2013.01); *A61K 47/32* (2013.01); *C08L 77/02* (2013.01)

(58) Field of Classification Search
CPC ....... C08G 69/22; C08G 69/00; A61K 9/0082
See application file for complete search history.

(56) References Cited

U.S. PATENT DOCUMENTS

2006/0194728 A1*  8/2006  Killian et al. .................. 514/12
2007/0087404 A1*  4/2007  Stahl et al. .................. 435/68.1

FOREIGN PATENT DOCUMENTS

WO    WO 2008011559 A2 *  1/2008

OTHER PUBLICATIONS

Zhang, JACS, 131, 2009.*
Waring, A.; Taeusch, H.W.; Bruni, R.; Amirkhanian, J.D.; Fan, B,R.; Stevens, R.; Young, J., Synthetic amphipathic sequences of surfactant protein-B mimic several physiochemical and in vivo properties of native pulmonary surfactant proteins, *Pept. Res.* 1989, 2, 308-313.
Waring, A. J.; Walther, F.; Gordon, L. M.; Hernandez-Juviel, J.; Hong, T.; Sherman, M.A.; Alonso, C.; Alig, T.; Brauner, J. W.; Bacon, D.; Zasadzinski, J., The role of charged amphipathic helices in the structure and function of surfactant protein B, *J. Pept. Res.* 2005, 66, 364-374.
Andersson, M., Curstedt, T.; Jornvall, H.; Johansson, J., An amphipathic helical motif common to tumorolytic polypeptide NK-lysin and pulmonary surfactant polypeptide SP-B, *FEES Lett.* 1995, 362, 328-332.
Appella, D.H.; Christianson, L.A.; Karle, I.L.; Powell, D.R.; Gellman, S.H., β-Peptide Foldamers: Robert Helix Formation in a New Family of β-Amino Acid Oligomers, *J. Am. Chem. Soc.* 1996, 118, 13071-13072.
Avery, M.E.; Mead, J., Surface Properties in Relation to Atelectasis and Hyaline Membrane Disease, *Am. J. Dis. Child.* 1959, 97, 517-523.
Beck, D.C.; Ikegami, M.; Na, C.L.; Zaltash, S.; Johansson, J.; Whitsett, J. A., Weaver, T.E., The Role of Homodimers in Surfactant Protein B function in Vivo, *J. Biol. Chem.* 2000,275, 3365-3370.
Bernardino De La Senna, J.; Perez-Gil, J.; Simonsen, A.C.; Bagatolli, L. A., Cholesterol Rules—Direct Observation of the Coexistence of Two Fluid Phases in Native Pulmonary Surfactant Membranes at Physiological Temperatures, *J. Biol. Chem.* 2004, 279, 40715-40722.
Bi, X.H.; Flack C.R.; Perez-Gil, J.; Plasencia, L.; Andreu, D.; Oliveira, E.; Mendelsohn, R., Secondary Structure and Lipid interactions of the N-Teratinal Segment of Pulmonary Surfactant SP-C in Langmuir Films: IR Reflection-Absorption Spectroscopy and Surface Pressure Studies, *Biochemistry* 2002,41, 8385-8395.

(Continued)

*Primary Examiner* — Susan Tran
*Assistant Examiner* — William Craigo
(74) *Attorney, Agent, or Firm* — Joseph T. Leone, Esq.; Daniel A. Blasiole; DeWitt Ross & Stevens S.C.

(57) ABSTRACT

Non-natural oligomers have recently shown promise as functional analogues of lung surfactant proteins Band C (SP-B and SP-C), two helical and amphiphilic proteins that are clitical for normal respiration. The generation of non-natural mimics of SP-B and SP-C has previously been restlicted to step-by-step, sequence-specific synthesis, which results in discrete oligomers that are intended to manifest specific structural attributes. Presented herein an alternative approach to SP-R mimicry that is based on sequence-random copolymers containing cationic and lipophilic subunits. These materials, members of the nylon-3 family, arc prepared by ling-opening polymelization of 13-lactams. The best of the nylon-3 polymers display promising in vitro surfactant activities in a mixed lipid film. Pulsating bubble surfactometry data indicate that films containing the most surface-active polymers attain adsorptive and dynamic-cycling properties that surpass those of discrete peptides intended to mimic SP-B.

15 Claims, 9 Drawing Sheets

(56) References Cited

OTHER PUBLICATIONS

Bringezu, F.; Ding, J.Q.; Brezesinski, G.; Zasadzinski, J.A., Changes in Model Lung Surfactant Monolayers Induced by Palmitic Acid, *Langmuir* 2001, 17, 4641-4648.

Brown, N.J.; Wu, C.W.; Seurynck-Servoss, S.L.; Barron, A.E., Effects of Hydrophobic Helix Length and Side Chain Chemistry on Biomimicry in Peptoid Analogues of SP-C, *Biochemistry* 2008, 47, 1808-1818.

Bruni, R.; Taeusch, H.W.; Waring, A.J., Surfactant protein B: Lipid interactions of synthetic peptides representing the amino-terminal amphipathic domain, *Proc. Natl. Acad. Sci. U. S. A.* 1991, 88, 7451-7455.

Cheng, R.P.; Gellman, S.H.; Degrado, W.F., β-Peptides: From Structure to Function, *Chem. Rev.* 2001A, 101, 3219-3232.

Cheng, M.; Deming, T.J., Controlled Polymerization of β-Lactams Using Metal-Amino Complexes: Synthesis of Block Copoly(β-peptides), *J. Am. Chem. Soc.* 2001B, 123, 9457-9458.

Cih-Kung, A.F.; Bozzelli, K. N.; Lockwood, N.A.; Haseman, J.R.; Mayo, K. H.; Tirrell, M., Promotion of Peptide Antimicrobial Activity by Fatty Acid Conjugation, *Bioconj. Chem.* 2004, 15, 530-535.

Cochrane, C.G.; Revak, S.D., Pulmonary Surfactant Protein B (SP-B): Structure-Function Relationships, *Science* 1991, 254, 566-568.

Creuwels, L.A.; Boer, E.H.; Demel, R.A.; Van Golde, L.M.G.; Haagsman, H.P., Neutralization of the Positive Charges of Surfactant Protein C, *J. Biol. Chem.* 1995, 270, 16225-16229.

Creuwels, L.; Vangolde, L.M.G.; Haagsman, H.P., The Pulmonary Surfactant System: Biochemical and Clinical Aspects, *Lung* 1997, 175, 1-39.

Dohm, M.T.; Seurynck-Servoss, S.L.; Seo, J.; Zuckermann, R. N.; Barron, A.E., Close Mimicry of Lung Surfactant Protein B by "Clicked" Dimers of Helical, cationic Peptoids, *Biopolymers Peptide Science* 2009, 92, 6, 538-553.

Epand, R.F.; Mowery, B.P.; Lee, S,E.; Stahl, S.S.; Lehrer, R.I.; Gellman, S.H., Dual Mechanism of Bacterial Lethality for a Cationic Sequence-Random Copolymer that Mimics Host-Defense Antimicrobial Peptides, *J. Mol. Biol.* 2008, 379, 38-50.

Gelman, M.A.; Lynn, D.M.; Weisblum, B.; Gellman, S.H., Biocidal Activity of Polystyrenes That are Cationic by Virtue of Protonation, *Org. Lett.* 2004, 6, 557-60.

Haagsman, H.P.; Diemel, R.V., Surfactant-associated proteins: functions and structural variation, *Camp. Biochem. Physiol. A. Mol. Integr. Physiol.* 2001, 129, 91-108.

Hashimoto, K., Ring-opening polymerization of lactams. Living anionic polymerization and its applications, *Prog. Polym. Sci.* 2000,25, 1411-1462.

Hawgood, S.; Schiffer, K., Structures and Properties of the Surfactant-Associated Proteins, *Annu. Rev. Physiol.* 1991, 53, 375-394.

Hawgood, S.; Ogawa, A.; Yukitake, K.; Schlueter, M.; Brown, C.; White, T.; Buckley, D.; Lesikar, D.; Benson, B.J., Lung Function in Premature Rabbits Treated with Recombinant Surfactant Protein-C, *Am. J. Respir. Crit. Care Med.* 1996, 154, 484-490.

Hayen, A.; Schmitt, M.A.; Ngassa, F.; Thomasson, K.A.; Gellman, S.H., Two Helical Conformtions from a Single Foldamer Backbone: "Split Personality" in Short α/β-Peptides, *Angew. Chem. Int. Ed.* 2004, 43, 505-510.

Horne, W.S.; Gellman S.H., Foldamers With Heterogeneous Backbones, *Ace. Chem. Res.* 2008, 41, 1399-1408.

Johansson, J.; Szyperski, T.; Curstedt, T.; Wuthrich, K., The NMR Structure of the Pulmonary Surfactant-Associated Polypeptide SP-C in an Apolar solvent Contains a Valyl-Rich α-Helix. *Biochemistry* 1994A, 33, 6015-6023.

Johansson, J.; Curstedt, T.; Robertson, B., The proteins of the surfactant system, *Eur. Respir. J.* 1994B, 7, 372-391.

Johansson, J.; Curstedt. T., Molecular structures and interactions of pulmonary surfactant components, *Eur. J. Biochem,* 1997, 244, 675-693.

Kirshenbaum, K.; Barron, A.E.; Goldsmith, R.A.; Armand, P.; Bradley, E.K.; Truong, K.T.V.; Dill K.A.; Cohen, F.E.; Zuckermann, R.N., Sequence-specific polypeptides: A diverse family of heteropolymers with stable secondary structure, *Proc. Natl. Acad. Sci. U. S. A.* 1998, 95, 4303-4308.

Kramer, A,; Wintergalen, A.; Sieber, M.; Galla, H.J.; Amrein, M.; Guckenberger, R., Distribution of the Surfactant-Associated Protein C within a Lung Surfactant Model Film Investigated by Near-field optical Microscopy, *Biophys. J.* 2000, 78, 458-465.

Lee, MR, Stahl, S.S., Gellman, S.H., Masters, K.S., Nylon-3 Copolymers that Generate Cell-Adhesive Surfaces Identified by Library Screening, 2009, *J. Am. Chem. Soc.*, 131, 16779-16789.

Lewis, J.E.; Jobe, A.H., Surfactant and the Adult respiratory Distress Syndrome, *Am. Rev. Respir. Dis.* 1993, 147, 218-233.

Merrifield, R.B., Solid Phase Peptide Synthesis. I. the Synthesis of a Tetrapeptide, *J. Am. Chem. Soc.* 1963, 85, 2149-2154.

Mingarro, L.; Lukovic, D.; Vilar, M.; Perez-Gil, J., Synthetic pulmonary surfactant preparations: new developments and future trends, *Curr. Med. Chem.* 2008, 15, 393-403.

Mowery, B.P.; Lee, S.E.; Kissounko, D.A.; Epand, R.F.; Epand, R.M.; Weisblum, B.; Stahl, S.S.; Gellman, S.H., Mimicry of Antimicrobial Host-Defense Peptides by Random Copolymers, *J. Am. Chem. Soc.* 2007, 129, 15474-15476.

Mowery, B.P.; Lindner, A.H.; Weislbum, B.; Stahl, S.S.; Gellman, S.H., Structure-activity Relationships among Random Nylon-3 Copolymers That Mimic Antibacterial Host-Defense Peptides, *J. Am. Chem. Soc.* 2009,131, 9735-9745.

Moya, F.; Maturana, A., Animal-Derived Surfactants Versus Past and Current Synthetic Surfactants: Current Status, *Clin. Perinatal.* 2007,34, 145-177.

Nadolski, M.J.; Linder, M.E., Protein lipidation, *FEES J.* 2007, 274, 5202-5210.

Notter, R.H. *Lung Surfactants: Basic Science and Clinical Applications;* Marcel Dekker: New York, 2000 (Copy Not Provided).

Orgeig, S.; Bernhard, W.; Biswas, S.C.; Daniels, C.B.; Hall, S.B.; Hetz, S.K.; Lang, C.J.; Maina, J.N.; Panda, A.K.; Perez-Gil, J.; Posmayer, F.; Veldhuizen, R.A.; Yan, W., The anatomy, physics, and physiology of gas exchange surfaces: is there a universal function for pulmonary surfactant in animal respiratory structures?, *Integr. Comp. Biol.* 2007, 47, 610-627.

Perez-Gil, J., Structure of pulmonary surfactant membranes and films; the role of proteins and lipid-protein interactions, *Biochim. Biophys. Acta* 2008, 1778, 1676-1695.

Pison, U.; Seeger, W.; Buchhorn, R.; Joka, T.; Brand, M.; Obertacke, U.; Neuhof, H.; Schmit-Nauerburg, K.P., Surfactant Abnormalities in Patients with Respiratory Failure after Multiple Trauma, *Am. Rev. Respir. Dis.* 1989, 140, 1033-1039.

Putz, G.; Goerke, J.; Taeusch, H.W.; Clements, J.A., comparison of captive and pulsating bubble surfactometers with use of lung surfactants, *J. Appl. Physiol.* 1994, 76, 1425-1431.

Ryan, M.A.; Qi, X.; Serrano, A.G.; Ikegami, M.; Perez-Gil, J.; Johansson, J.; Weaver, T.E., Mapping and Analysis of the Lytic and Fusogenic Domains of the Surfactant Protein B, *Biochemistry* 2005,44, 861-872.

Ryan, M.A.; Akinbi, H.T.; Serrano, A.G.; Perez-Gil, J.; Wu, H.X.; McCormack, F.X.; Weaver, T.E., Antimicrobial Activity of Native and Synthetic Surfactant Protein B Peptides, *J. Immunol.*, 2006, 176,416-425.

Schmitt, M.A.; Weisblum, B.; Gellman, S.H., Interplay among Folding, Sequence, and Lipophilicity in the Antibacterial and Hemolytic Activities of α/β-Peptides. *J. Am. Chem. Soc.* 2007, 129, 417-428.

Schurch, S.; Qanbar, R.; Bachofen, H.; Possmayer, F., The Surface-Associated Surfactant Reservoir in the Alveolar Lining, *Biol. Neonate* 1995, 67, 61-76.

Serrano, A.G.; Ryan, M.A.; Weaver, T.E.; Perez-Gil, J., Critical Structure-function Determinants within the N-Terminal Region of Pulmonary Surfactant Protein SP-B, *Biophys. J.* 2006, 90, 238-249.

Seurynck, S. L.; Patch, J. A.; Barron, A.E., Simple, Helical Peptoid Analogs of Lung Surfactant Protein B, *Chem. Biol.* 2005A, 12, 77-88.

Seurynck, S.L.; Brown, N.J.; Wu, C.W.; Germino, K.W.; Kohlmeir, E.K.; Ingenito, E.P.; Glucksberg, M.R. Barron, A.E.; Johnson, M., Optical monitoring of bubble size and shape in a pulsating bubble surfactometer. *J. Appl. Physiol.* 2005B, 99, 624-633.

Seurynck-Servoss, S.L.; Dohm, M.T.; Barron, A.E., Effects of Including an N-Terminal Insertion Region and Arginine-Mimetic

(56) References Cited

OTHER PUBLICATIONS

Side Chains in Helical Peptoid Analogues of Lung Surfactant Protein B, *Biochemistry* 2006, 45, 11809-11818.

Seurynck-Servoss, S. L.; Brown, N.J.; Dohm, M. T.; Wu, C. W.; Barron, A. E. *Coll. Surf B. Biointerfaces* 2007, 57, 37-55.

Shai, Y., Mechanism of the binding, insertion and destabilization of phospholipid bilayer membranes by α-helical antimicrobial and cell non-selective membrane-lytic peptides, *Biochim. Biophys. Acta* 1999, 1462, 55-70.

Tanaka, Y.; Takei, T.; Aiba, T.; Masuda, K.; Kiuchi, A.; Fujiwara, T., Development of synthetic lung surfactants, *J. Lipid Res.* 1986, 27, 475-485.

Vandenbussche, G.; Clercx, A.; Clercx, M.; Curstedt, T.; Johansson, J.; Jornvall, H.; Ruysschaert, J.M., Secondary Structure and Orientation of the Surfactant Protein SP-B in a Lipid Environment. A Fourier Transform Infrared Spectroscopy Study, *Biochemistry* 1992,31, 9169-9176.

Veldhuizen, E.J.A.; Waring, A.J.; Walther, F.J.; Batenburg, J. J.; Van Golde, L.M.G.; Haagsman, H. P., Role of pulmonary surfactant components in surface film formation and dynamics, *Biophys. J.* 2000A, 79, 377-384.

Veldhuizen, E.J.A.; Haagsman, H.P., Dimeric N-Terminal Segment of Human Surfactant Protein B (dSP-$B_{1-25}$) Has enhanced Surface Properties Compared to Monomeric SP-$B_{1-25}$, *Biochim. Biophys. Acta* 2000B, 1467, 255-270.

Wang, Y.D.; Rao, K.M.K.; Demchuk, E., Topographical Organization of the N-Terminal Segment of Lung Pulmonary Surfactant Protein B (Sp-$B_{1-25}$) in Phospholipid Bilayers, *Biochemistry* 2003, 42,4015-4027.

Waring, A.; Taeusch, H.W.; Bruni, R.; Amirkhanian, J.D.; Fan, B.R.; Stevens, R.; Young, J., The role of charged amphipathic helices in the structure and function of surfactant protein B, *Pept. Res.* 1989, 2, 308-313.

Waring, A. J.; Walther, F.; Gordon, L. M.; Hernandez-Juviel, J.; Hong, T.; Sherman, M.A.; Alonso, C.; Alig, T.; Brauner, J. W.; Bacon, D.; Zasadzinski, J. *J. Pept. Res.* 2005, 66, 364-374.

Wu, C.W.; Seurynck, S.L.; Lee, K.Y.C.; Barron, A.E., Helical Peptoid Mimics of Lung Surfactant Protein C, *Chem. Biol.* 2003, 10, 1057-1063.

Zhang, J.; Kissounko, D.A.; Lee, S.E.; Gellman, S.H.; Stahl, S.S., Access to poly-β-peptides with functionalized side chains and End Groups via controlled Ring-Opening Polymerization of β-Lactams, *J. Am. Chem. Soc.* 2009,131, 1589-1597.

Zuckermann, R.N.; Kerr, J.M.; Kent, S.B.H.; Moos, W.H., Efficient Method for the Preparation of Peptoids [Oligo(N-substituted glycines)] by Submonomer solid-Phase Synthesis, *J. Am. Chem. Soc.* 1992, 114, 10646-10647.

\* cited by examiner

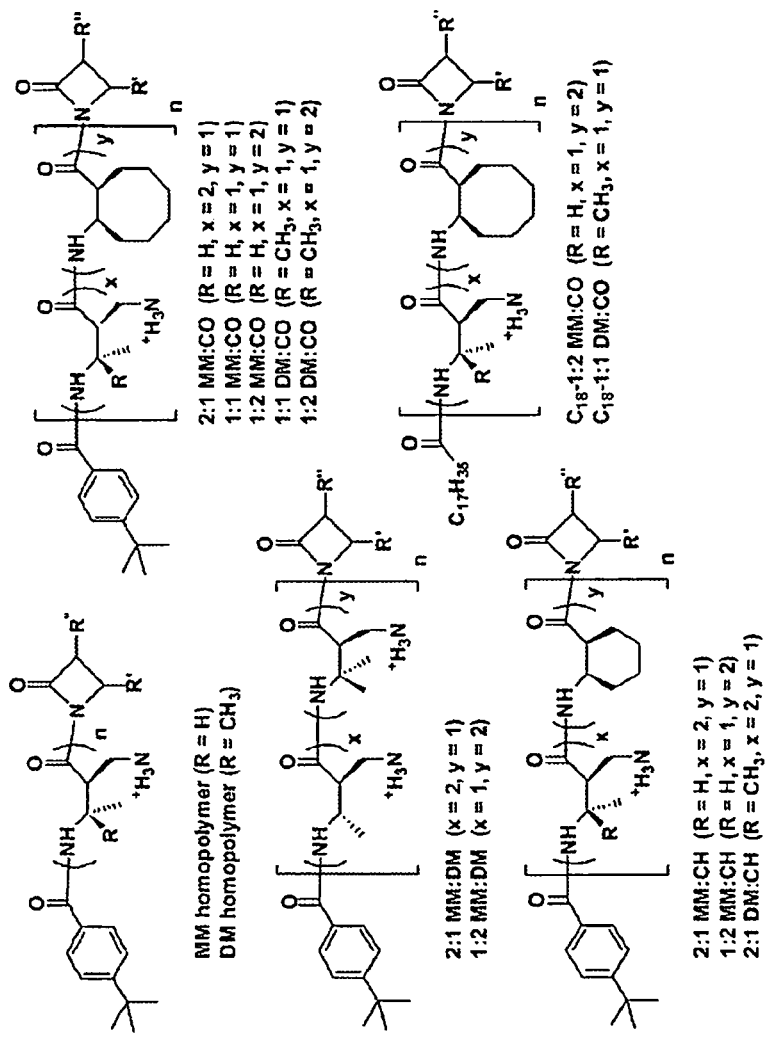
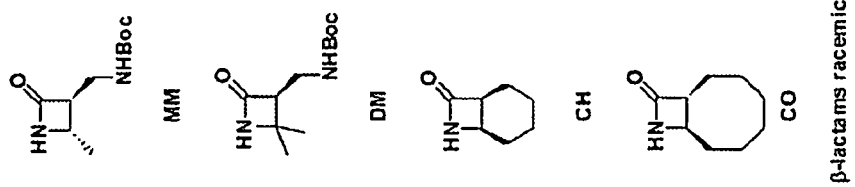

FIG. 7

Bar chart showing Concentration (μg mL$^{-1}$) — ID50:

- SP-B (1-25): 4.4
- Peptoid B1: 1.7
- 2DM:1CH: 12.0
- 1MM:2CO a: 28.0
- C18-1MM:2CO: 22.7
- 2MM:1CO a: 17.3
- 2MM:1CO b: 17.1
- 1DM:1CO a: 23.0
- 1DM:1CO c: 10.9
- C18-1DM:1CO: 11.2
- 2DM:1CO a: 9.0

US 9,044,392 B2

NYLON-3 CO-POLYMERS AND SYNTHETIC LUNG SURFACTANT COMPOSITIONS CONTAINING SAME

CROSS-REFERENCE TO RELATED APPLICATIONS

The present application is a U.S. National Phase application of PCT/US2011/028813, filed Mar. 17, 2011, which claims the benefit of priority to U.S. Provisional Patent Application No. 61/315,708, filed Mar. 19, 2010.

FEDERAL FUNDING STATEMENT

This invention was made with government support under 0404704, 0425880, and 0101195 awarded by the National Science Foundation and HL067984 awarded by the National Institutes of Health. The government has certain rights in the invention.

REFERENCES CITED

Complete bibliographic citations are included in the References section. All reference cited are incorporated herein by reference.

FIELD OF THE INVENTION

The invention is directed to synthetic nylon-3 co-polymers, synthetic lung surfactant compositions containing them, and methods to treat pulmonary disorders (notably infant, adult, and acute respiratory distress syndromes) using the compositions.

BACKGROUND

Lung surfactant proteins SP-B and SP-C are required for the biophysical activity of lung surfactant (LS), the complex lipid-protein mixture that coats the internal air-liquid (a/l) interface of the vertebrate lung and reduces the work of breathing.[1,2] Both proteins (~1.5-2.0 combined wt % of natural LS) contain a high proportion of lipophilic residues, and they adopt amphiphilic and helical conformations. The main function of LS is to regulate surface tension ($\gamma$, mN m$^{-1}$) in the alveoli (tiny sacs that mediate gas exchange between the blood and air spaces of the lung) by optimizing available surface area, maximizing lung compliance, and stabilizing the alveolar network against collapse.[3] Three crucial functional characteristics of LS are: (1) rapid adsorption to the a/l interface, (2) near-zero $\gamma$ upon film compression, and (3) efficient re-spreading of material and minimal loss to the subphase through multiple breathing cycles.[4]

Deficient or dysfunctional LS results in infant or acute respiratory distress syndromes (IRDS or ARDS, respectively).[5,6] Although no current exogenous treatment for ARDS exists,[7] IRDS can be successfully treated with porcine- or bovine-derived surfactant replacement therapies (SRTs).[8] Use of animal-derived substances, however, is non-ideal because of the risk of zoonotic infection and the high cost of large-scale extraction, isolation, and purification. To eliminate dependence on animal-derived material, many groups have sought to develop biomimetic LS replacements based on synthetic surfactant protein analogues.[4] This approach could lead to a safe and bioavailable alternative to SRTs that may be able to treat or mitigate both IRDS and ARDS.

SP-B in monomeric form is a 79-residue protein (8.7 kDa) with a net cationic charge, and is postulated to contain four or five facially amphiphilic helices. SP-B forms four disulfide bonds: three intramolecular connections that presumably constrain conformational flexibility, and one intermolecular bond that results in homodimerization.[9-12] SP-C contains just 35 residues and forms a single helix.[13] This protein has two palmitoylation points (positions 5 and 6), two cationic residues (11 and 12), and an extremely lipophilic poly-valine helix that approximates the length necessary for spanning a lipid bilayer.[12,14-17] The sequences and structural attributes of both proteins are highly conserved across mammalian species, implying that these features are necessary for their ability to organize and regulate lipid film formation, and to anchor the film to the a/l interface.[3,18] Unfortunately, these attributes render the proteins very troublesome to obtain on a large scale by extraction or chemical synthesis; efforts to synthesize SP-B or SP-C or fragments thereof are often hampered by misfolding or aggregation.[4]

The main approaches toward functional mimicry of surfactant proteins have involved peptide fragment synthesis, limited dimerization of SP-B, recombinant protein expression, and more recently, peptoid synthesis, the subject of recent contributions in this field.[19-24] Although a recombinant form of SP-C is available,[25] it is not palmitoylated, and no recombinant form of SP-B has yet been reported. Chemically synthesized, surface-active peptide fragments of SP-B such as SP-B$_{1-25}$[26,27] and the dimeric constructs dSP-B$_{1-25}$[28] and "Mini-B",[29] have demonstrated in vitro and in vivo success, but the challenge of generating these materials on a large scale is a stumbling block to pharmaceutical development. The chronic problem of achieving the desired extent of dimerization and multiple amphiphilic helices when mimicking SP-B has prompted recent endeavors to determine whether the incorporation of dimerization points can be circumvented while retaining good surfactant activity.[24,30]

The high cost of large-scale, step-wise synthesis and purification represents a significant barrier to the development of peptide-based drugs and has generated an interest in alternatives for use in an LS replacement.[4] Non-natural oligomers, such as peptoids,[31] $\beta$-peptides[32,33] and $\alpha/\beta$-peptides[34,35] can circumvent some peptide-associated problems, including irreversible aggregation and protease susceptibility; however, step-wise synthesis is required for preparation of these sequence-specific oligomers, and reversed-phase high performance liquid chromatography (RP-HPLC) is necessary for their purification.[32,36] Therefore, although these types of peptide mimics can display impressive biological activities and thereby shed light on relationships between molecular structure and resultant biophysical activities, sequence-specific non-natural oligomers do not alleviate the production cost problem.

SUMMARY

The invention is directed to a method of treating pulmonary disorders involving deficient or dysfunctional lung surfactant in mammals, including humans, as well as a corresponding composition for carrying out the method. The method comprises administering to a mammalian subject in need thereof an artificial lung surfactant composition comprising an amount of a nylon-3 homopolymer or random copolymer whose monomers are selected from the group consisting of:

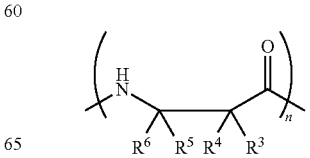

wherein $R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl; or one of $R^3$ and $R^4$ combined with of $R^5$ and $R^6$, together with the carbon atoms to which they are attached, define a cyclic moiety "A"

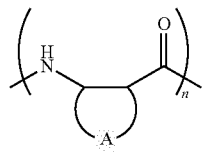

wherein "A" is selected from the group consisting of substituted or unsubstituted $C_5$-$C_{12}$ cycloalkyl, $C_5$-$C_{12}$ cycloalkenyl, and five- to twelve-membered heterocyclic; provided that at least two. of $R^3$, $R^4$, $R^5$, or $R^6$ are not hydrogen; and wherein "n" is a positive integer (preferably from about 5 to about 500, and more preferably from about 10 to about 100). The composition may be used to treat infant, acute, or adult respiratory distress syndromes.

The copolymers may also be fabricated in non-random fashion, such as block copolymers, which may also be used to treat the various pulmonary ailments described herein.

More specific subsets of the subject compounds may also be used. For example, compound can be used where one of $R^3$ and $R^4$ combined with one of $R^5$ and $R^6$, together with the carbon atoms to which they are attached, define a cyclic moiety "A"

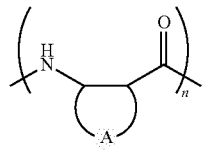

wherein "A" is selected from the group consisting of substituted or unsubstituted $C_5$-$C_{12}$ cycloalkyl, $C_5$-$C_{12}$ cycloalkenyl, and five- to twelve-membered heterocyclic; and the other of $R^3$ and $R^4$ and the other of $R^5$ and $R^6$ are independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl. In this situation, the backbone of the compounds are rigidified by the presence of a cyclic moiety that includes the two backbone carbon atoms of each monomer.

Also disclosed herein is an artificial lung surfactant composition comprising a nylon-3 homopolymer, random copolymer, or non-random copolymer, whose monomers are selected from the group consisting of:

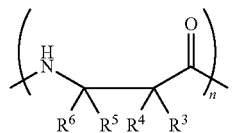

wherein:
$R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl; or one of $R^3$ and $R^4$ combined with one of $R^5$ and $R^6$, together with the carbon atoms to which they are attached, define a cyclic moiety "A"

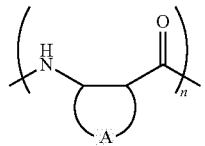

wherein "A" is selected from the group consisting of substituted or unsubstituted $C_5$-$C_{12}$ cycloalkyl, $C_5$-$C_{12}$ cycloalkenyl, and five- to twelve-membered heterocyclic;

provided that at least two of $R^3$, $R^4$, $R^5$, or $R^6$ are not hydrogen; and wherein "n" is a positive integer.

Optionally, the artificial lung surfactant may be further admixed with a lipid delivery vehicle. It is preferred, although not required, that "n" is an integer from about 5 to about 500, and more preferably from about 10 to about 100.

BRIEF DESCRIPTION OF THE FIGURES

FIGS. 1A and 1B depict the exemplary monomers (FIG. 1A) and polymers (FIG. 1B) described in the Examples. The copolymers are sequence-random. Because the β-lactams are racemic, the polymers are heterochiral and stereo-random. The C-terminal imide unit is derived from the beta-lactam(s) used in the polymerization reaction. Thus, for each copolymer, R' and R" could correspond to either of the β-lactam precursors. All polymers are cationic and were isolated as trifluoroacetate salts. Nomenclature, characterization, and synthesis details are presented in the Examples.

FIG. 7 is a historgram depicting cytotoxicity assay data for polymers and peptide or peptoid positive controls. Cytotoxicity data for select polymers, the SP-B$_{1-25}$ peptide, and Peptoid B1 against NIH/3T3 fibroblast cells. Error bars represent the standard error of the mean (SEM).

FIGS. 8A and 8B each represent a Tanaka lipid (TL, DPPC:POPG:PA) monolayer at the air-liquid interface, with black spheres representing DPPC, gray spheres representing POPG, and white spheres representing PA. Copolymers with a p-(cert-butyl)benzoyl end group (FIG. 8A) adopt an amphiphilic conformation and insert into the lipid film, where they are able to retain attached lipids via Coulombic interactions between cationic subunits and charged lipid head groups, or hydrophobic interactions between lipophilic subunits and the lipid acyl chains. However, octadecanoylated copolymers (FIG. 8B) could act as lipid "anchors" by increasing the degree of insertion into the lipid acyl chains through hydrophobic hydrocarbon chain-chain interactions. These polymers may also be able to sustain sublayer lipid structures by either adopting a lipid-associated amphiphilic conformation, or utilizing the octadecanoyl chain to retain pockets of lipid material.

DETAILED DESCRIPTION

Figure 2:
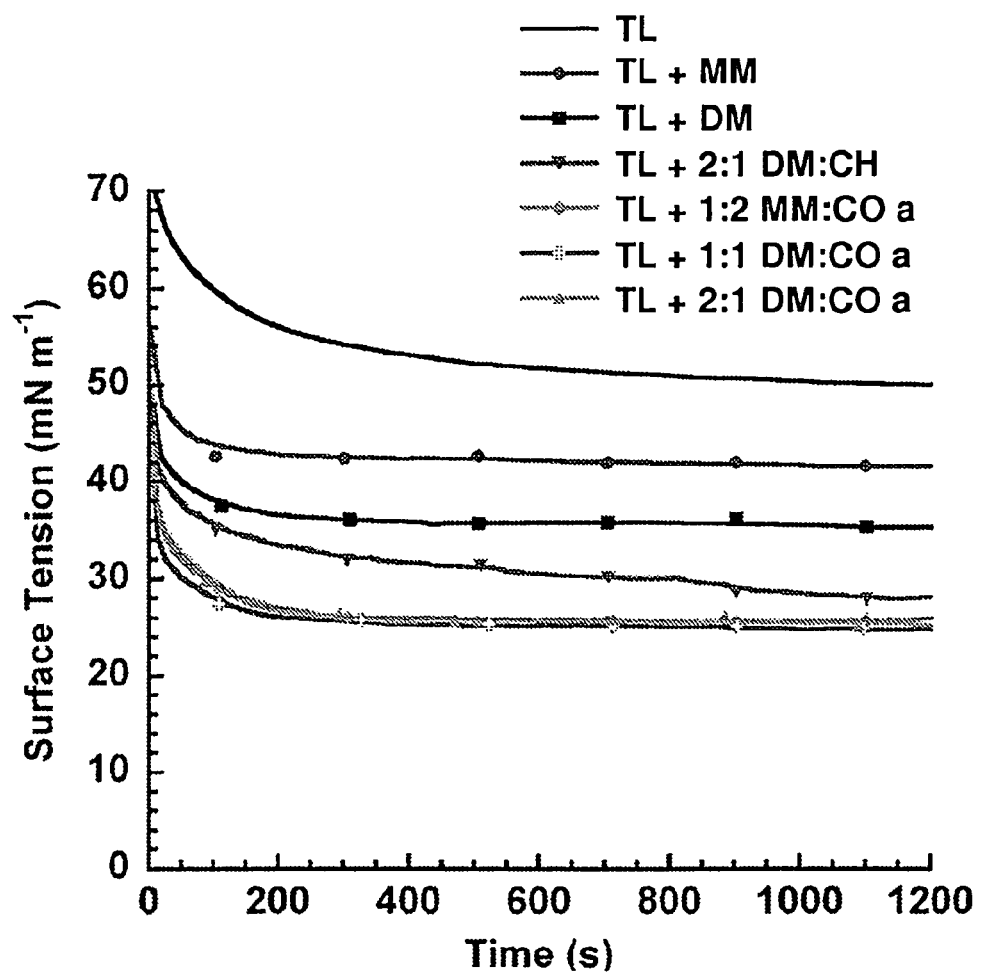
FIG. 2 is a graph depicting PBS Adsorption for Lipid-Polymer Films in Static-Bubble Mode at 37° C. Representative static-bubble adsorption traces for Tanaka lipids alone (TL) and TL+10 relative weight % of each mimic in an aqueous buffer (150 mM NaCl, 10 mM HEPES, 5 mM $CaCl_2$, pH 6.9) suspension at 37° C.

It is generally assumed that the function of a protein depends upon the sequence of amino acid residues and the three-dimensional arrangement of amino acid side chains (or a subset thereof) that results from adoption of a specific secondary or tertiary structure. Recently, however, it was proposed that discrete sequences and folding patterns may not be necessary for mimicry of the cell type-selective toxicity of host-defense peptides.[37,38] Many of these natural antimicrobial peptides adopt helical conformations upon interaction with bacterial membranes and ultimately compromise the barrier function of the membrane; these peptides are generally selective as membrane-disrupting agents, acting on bacteria in preference to eukaryotic cells.[39] In the present work, it has been hypothesized that nylon-3 copolymers might be able to mimic lung surfactant proteins SP-B and SP-C, the function of which depends upon interaction with lipids,[18] as is true of natural antimicrobial peptides.

The invention is thus directed to nylon-3 homopolymers and sequence-random copolymers that mimic lung surfactant protein B. These polymers are useful to treat pulmonary disorders involving deficient or dysfunctional lung surfactant, such as infant, acute, and adult respiratory distress syndrome. (As used herein, the term "pulmonary disorder" encompasses a wide variety of lung ailments that adversely impact natural lung surfactant, including the above-noted respiratory distress syndromes, as well as pneumonia, other types of sepsis, meconium aspiration, acute lung injury, respiratory syncytial virus infection, and the like.) These polymers can be incorporated into synthetic lung surfactant compositions to be instilled into the lungs of a mammalian subject in need of such treatment. The efficacy of the designs was estimated by in vitro surfactant behavior in a mixed lipid film. Surface activity has been evaluated by pulsating bubble surfactometry (PBS)[43,44] of copolymers in a Tanaka lipid (TL) film[45] (1,2-diacyl-sn-glycero-3-phosphocholine (DPPC): 1-palmitoyl-2-oleoyl-sn-glycero-3-[phospho-rac-(1-glycerol)] (POPG): palmitic acid (PA) 68:22:9 by weight). The materials, which were synthesized via anionic ring-opening polymerization of β-lactams,[42,46] display increased surface-active behavior relative to known peptide- and peptoid-based SP-B mimics, with values approaching that of native SP-B in the TL film.[30] These nylon-3 copolymers display lower toxicity toward mammalian cells than do an SP-B-derived peptide and a peptoid-based mimic. The polymers are heterochiral because they were prepared from racemic β-lactams; therefore, these nylon-3 copolymers cannot adopt specific and regular conformations. Thus, the results challenge the notion that a helix or other regular conformation is strictly required if a molecule is to achieve global amphiphilicity (i.e., global segregation of lipophilic and hydrophilic subunits), a property that is thought to be necessary for SP-B-like activity. It is postulated that the nylon-3 copolymers are able to achieve global amphiphilicity in irregular conformations after association with lipids, which facilitate their surfactant behavior.

As demonstrated herein, nylon-3 copolymers with random sequences of cationic and lipophilic subunits and random backbone stereochemistry can display in vitro surfactant activity in mixed lipid films analogous to that of SP-B or of a sequence-specific peptide- or peptoid-based surfactant protein B mimic. In many cases, the surface activities of the polymers match or exceed those of peptide- and peptoid-based positive controls. The cytotoxicities of the nylon-3 copolymers toward mammalian cells are lower than those of a well-studied peptide fragment of SP-B and Peptoid B1. These results are highly significant because the polymers presumably cannot adopt a regular conformation that would lead to global segregation of lipophilic and cationic side chains. In addition, the copolymers are much less costly to prepare than are sequence-specific oligomers such as peptides.

The polymer synthesis method employed[46] enables facile variation of subunit identities and the N-terminal group, and this capability was utilized to make and evaluate a set of nylon-3 materials as LS protein mimics. Variations in polymer composition led to clear trends in terms of in vitro surface activity. In adsorption experiments, copolymers containing both lipophilic and cationic subunits display the most desirous behavior. Two different lipophilic subunits were examined, CH and CO (see FIG. 1A). Incorporation of CO subunits (FIG. 1A) yielded compositions that achieved properties similar to those of SP-B in the same lipid film (these properties of SP-B are described in a submitted manuscript).[30] The best properties were observed for copolymers containing ≥50% CO subunits, with the remainder of the subunits cationic (MM or DM). Variation in the N-terminal group, p-(tert-butyl)benzoyl vs. octadecanoyl, had little impact on the static measurements. However, in the dynamic cycling measurements, the octadecanoyl end group proved to be superior.

The structural difference between the two cationic subunits employed, DM and MM, is relatively subtle: DM contains an additional $CH_2$ unit relative to MM. Nevertheless, favorable effects of DM vs. MM are noticeable in the dynamic measurements. Films containing DM:CO copolymers reached a slightly lower $\gamma_{max}$, more consistently attained a near-zero $\gamma_{min}$, and exhibited significantly less percent surface area compression to reach a surface tension of 20 mN m$^{-1}$ relative to films containing MM:CO copolymers. In these two copolymer families, placement of an octadecanoyl group at the N-terminus was quite beneficial, leading to the lowest $\gamma_{max/min}$ values and the lowest percent surface area compression to reach 20 mN m$^{-1}$ of all the lipid-polymer films examined. In addition, for the N-terminal octadecanoyl polymers, the loop shape manifested by the lipid-copolymer films is substantially more like that of Infasurf®[44] or of SP-B in a lipid film (submitted manuscript),[+] exhibiting significantly less hysteresis and more uniform loop shape, relative to the N-terminal p-(tert-butyl)benzoyl polymers.

Protein lipidation as a natural modification enhances protein-membrane interactions and lipid-associated functioning,[54] and examples of designed peptide-fatty acid conjugation to enhance biological activity are present in the literature.[55] In the nylon-3 copolymers, replacing the p-(tert-butyl)benzoyl end group with a more lipophilic octadecanoyl end group probably enhances lipid-polymer interactions, especially in highly compressed surfactant states, a situation in which a polymer lacking the highly lipophilic end group might otherwise be excluded from (or "squeezed-out" of) the lipid film. In addition, incorporation of the octadecanoyl group may promote polymer-polymer association through hydrophobic interactions of the hydrocarbon chains.[42]

Figure 8A:
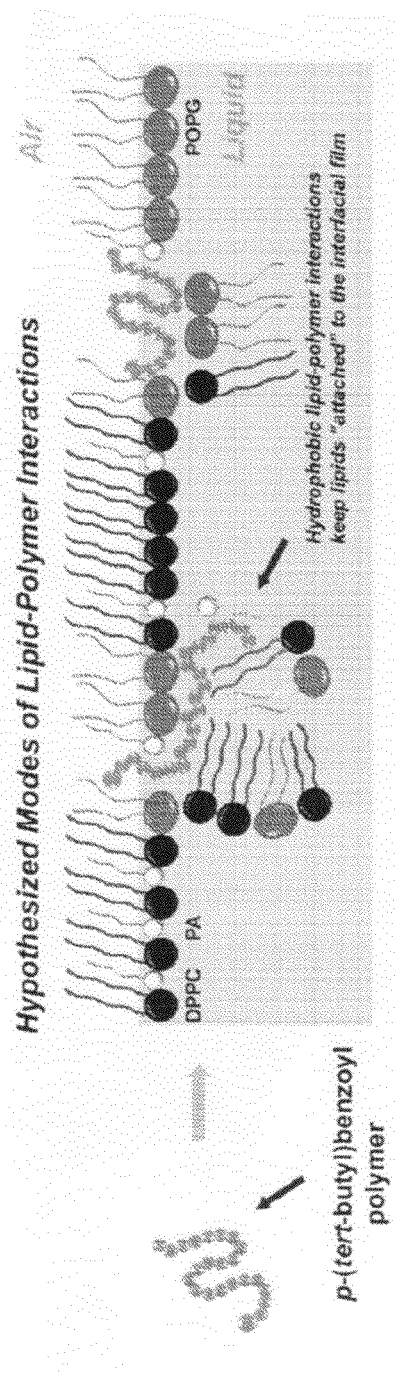
FIGS. 8A and 8B are schematic diagrams depicting hypothesized modes of lipid-polymer interactions. While not being limited to any specific mechanism or underlying biological phenomenon, these are the hypothesized lipid-polymer interaction(s) contributing to enhanced surface activity. For the polymers, blue spheres represent the lipophilic units while red spheres indicate cationic units. The gray sphere in the "polymer sequence" of FIG. 8A represents the p-(cert-butyl)benzoyl end group, while the gray line extending from the "polymer sequence" in FIG. 8B represents the octadecanoyl chain. Therefore, the picture outlines two possibilities of modes of action: one for polymers without an octadecanoyl chain (FIG. 8A), and one for octadecanoylated polymers (FIG. 8B).
Figure 8B:
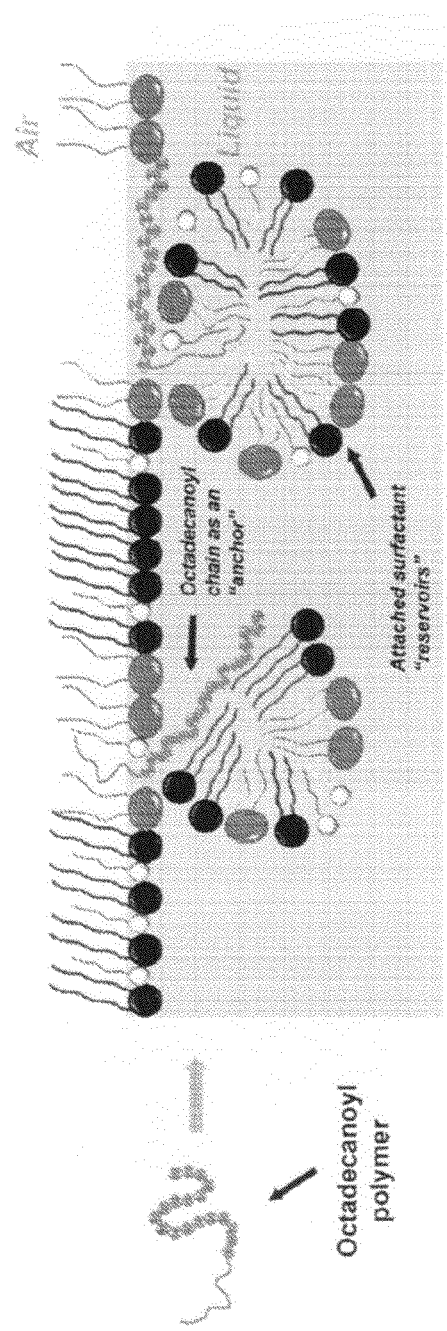

FIGS. 8A and 8B propose distinct modes of lipid-polymer interaction for the copolymers bearing an N-terminal p-(tert-butyl)benzoyl group (small gray lipophilic unit; hypothesis A) vs. copolymers bearing an N-terminal octadecanoyl group (large gray -lipophilic unit; hypothesis B). FIGS. 8A and 8B each represent DPPC:POPG:PA lipid monolayers at the air-liquid interface. At physiological temperature in the relevant surface tension regime assayed by the PBS (~0-40 mN/m surface tension), the lipid monolayer is composed of lipid-ordered regions, consisting of tightly packed saturated lipids DPPC:PA, and lipid-disordered regions that largely comprise unsaturated POPG.[56] From previous work, it is known that natural SP-B and SP-C, as well as peptide- and peptoid-based surfactant protein mimics, reside in the fluid phase of the film. Therefore it is assumed that the P would likely occupy the same region.[30,57] In FIG. 8A, on one hand, the polymer adopts a lipid-associated amphiphilic conformation and "inserts" into the lipid film. The cationic subunits of the polymer could be favorably solvated by the aqueous buffered subphase or be attracted Coulombically to the anionic lipid head groups of POPG and PA, while the lipophilic subunits could facilitate interactions with the lipid acyl chains in or below the interfacial film. In FIG. 8B, on the other hand, the large lipophilic end group could enable a polymer molecule to behave as a lipid "anchor," facilitating deeper insertion into the acyl chains of the interfacial lipid monolayer, and sustaining a "surfactant reservoir" of lipids attached to the interfacial lipid film via favorable interactions between the polymer and lipids in both the interfacial film and the reservoir. Such reservoirs are known to occur in natural LS and are believed to be responsible for increasing interfacial adsorption, reducing γ, and allowing efficient re-spreading of the interfacial film upon inspiration.[58] This behavior is postulated to occur more substantially with SP-C than with SP-B, where the highly lipophilic helix of SP-C is capable of spanning the length of a lipid bilayer;[59] thus, it is possible that the octadecanoyl polymers emulate some surface-active attributes of both SP-B and SP-C. Applicants note that the mechanisms depicted in FIGS. 8A and 8B are hypotheses only. The invention disclosed and claimed herein is not limited to any specific mechanisms or underlying biological phenomena.

It is widely believed that the global segregation of cationic and lipophilic side chains on the surface of SP-B, i.e., the protein's global amphiphilicity, is critical to the interactions of this protein with lipids and the overall surfactant function.[29,61] This global amphiphilicity, in turn, depends upon adoption of a specific folding pattern. Most mimics of surfactant proteins examined to date have been sequence-specific oligomers, either peptides or peptoids;[4] these oligomers have been designed to adopt a specific conformation, usually a helix, that is globally amphiphilic by virtue of the amino acid sequence.

If one assumes that a specific globally amphiphilic conformation must be adopted in order for an oligomer or polymer to display surfactant protein-like behavior, then it might seem pointless to explore sequence- and stereo-random copolymers in this regard, despite the profound advantages offered by such copolymers in terms of synthesis, relative to sequence-specific oligomers. However, the favorable in vitro properties observed for some of the nylon-3 copolymers suggest that the adoption of a specific conformation may not be required for effective lung surfactant protein B mimicry. It is proposed that the nylon-3 copolymers can achieve global amphiphilicity via irregular conformations that lead to induced segregation of cationic and lipophilic side chains in a lipid-buffer environment.

The current study provides the first evidence that sequence-random copolymers can mimic the behavior of surfactant protein B in terms of in vitro surface activity in a mixed lipid film. The findings indicate that nylon-3 copolymers can be used in a lung surfactant replacement therapy. These polymers represent a cost-effective strategy for generating lung surfactant protein mimics that does not rely on step-wise synthesis, extensive purification, or generating complex structural motifs through more complex chemistries. This work thus effectively demonstrates that: (1) sequence-random copolymers positively interact with a lipid film to dramatically enhance surface activity; (2) cyclooctyl subunit inclusion in the sequence substantially lowers the surface tension of the interfacial film; and (3) N-terminus octadecanoylation provides additional surface activity improvement, demonstrating that both SY-B and SY-C can be effectively mimicked with one molecule. These findings challenge the notion that helicity is a strict requirement for amphiphilicity where lipid-bound molecules are concerned. Instead, it is postulate that the copolymers can adopt an irregular conformation that nevertheless is globally amphiphilic and surface-active.

Chemistry

As used herein, the phrase "substituted or unsubstituted," when referring to a chemical moiety, means that the chemical moiety may appear as the basic unsubstituted moiety (e.g., an alkyl group having no other molecules beyond carbon and hydrogen), or the chemical moiety is substituted with one or more substituents, e.g. alkyl, halogen, alkoxy, acyloxy, amino, hydroxy, mercapto, carboxy, benzyl, etc.

The homopolymers and copolymers described herein can be fabricated via a ring-opening polymerization of β-lactam-containing monomers. Exemplary reactions are shown in Reaction Schemes 1 and 2:

Reaction Scheme 1

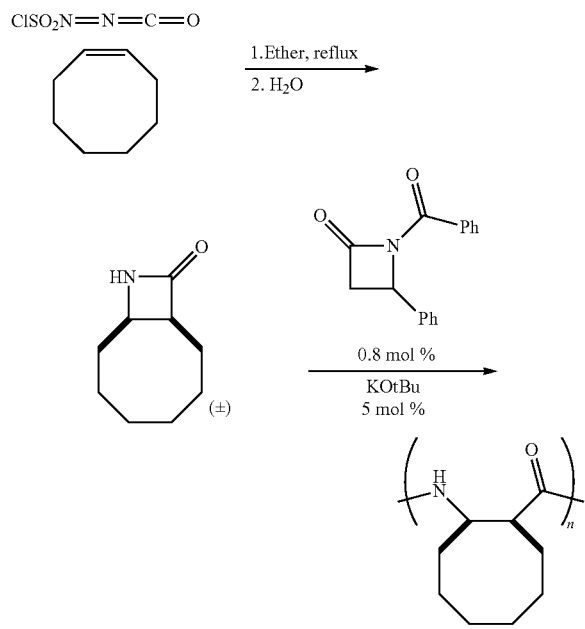

Reaction Scheme 2

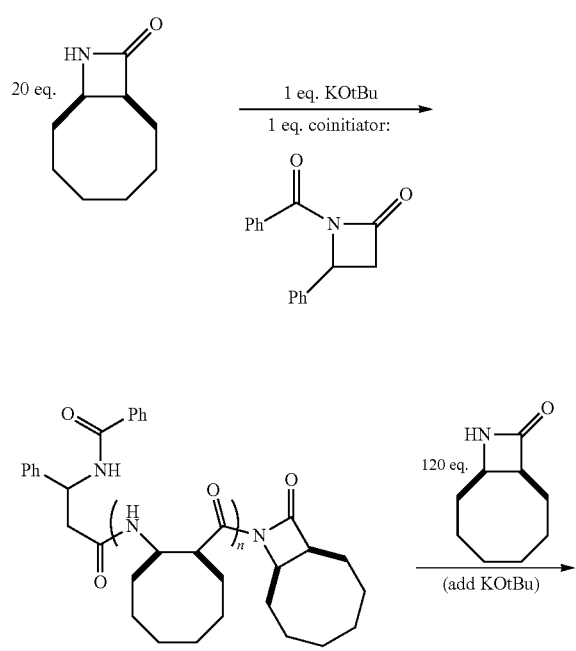

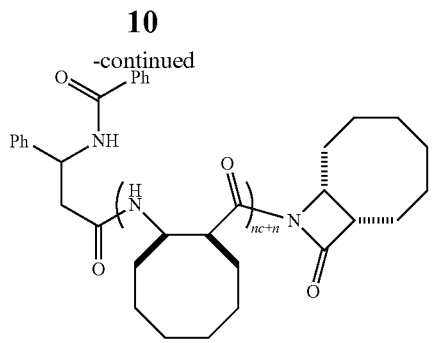

Note that the reactant monomers can be monocyclic (e.g., see monomers 10 and 13 in the Examples) or bicyclic (e.g., see Reaction Schemes 1 and 2, which illustrate the polymerization of compound 6; see the Examples). As shown in Reaction Schemes 1 and 2, the reaction proceeds in the presence of a base (potassium-t-butoxide in these two representative reactions) and a co-initiator (N-benzoyl-4-phenyl-β-lactam, also known systematically as N-benzoyl-4-phenyl azetidin-2-one).

The inventive reaction route is extremely versatile and has a great many benefits. Most notably, β-peptides of controlled molecular weights (Mn) of anywhere from about 1,000 Da to about 20,000 and larger can be obtained, using very common (and cheap) reagents. In typical reactions (where the time of reaction is not being unduly extended), β-peptides of controlled molecular weights of from about 1,000 Da to about 12,000 Da are readily obtained. Many of the β-polypeptide polymers thus obtained are soluble in common organic solvents, including dichloromethane, chloroform, and tetrahydrofuran (THF). The molecular weight distribution of the resulting polymers is quite narrow. For example, the monomer shown in Reaction Scheme 1 (a bicyclic compound comprising a β-lactam ring fused to a cyclooctane ring) was polymerized according to the present invention via an opening of the β-lactam ring to yield a polymer having an Mn of 11,400 Da (as measured by gel permeation chromatography), with a polydispersity index (PDI, calculated via gel permeation chromatography using a laser light-scattering detectors) of only 1.05. ("Polydispersity index" is also sometimes referred to as "molecular weight distribution" and is the ratio of the weight-average molecular weight (Mw) to number-average (Mn) molecular weight.) As a general rule, the inventive method will generate β-polypeptides with a PDI of less than about 2.0, more preferably less than about 1.5, and more preferably still less than about 1.3.

The reaction can proceed either in the presence or absence of a co-initiator. The polymerization reaction will proceed without an co-initiator, but the PDI tends to rise without the co-initiator. Suitable non-β-lactam co-initiators include aromatic acyl halides, preferably substituted or unsubstituted benzoyl halides, such as 4-tert-butyl-benzoyl chloride and 4-chloromethyl benzoyl chloride (both of which can be obtained commercially from several international suppliers, including Sigma-Aldrich, Milwaukee, Wis.), and the like.

As shown in Reaction Scheme 2, the reaction is a living polymerization and thus can be used to fabricate homopolymers, random co-polymers, block co-polymers, and the like. As used herein, the term "living polymerization" assumes its conventional meaning in the art, namely: a polymerization in which the ability of a growing polymer chain to terminate has been inhibited or abolished. Thus, the polymerization reaction can be carried out in stages, using monomers, first-stage pre-polymers, and/or second-stage (and/or subsequent-stage) pre-polymers as the reactants. Because the reaction is a living polymerization, the inventive route described herein provides exquisite control of the polymerization process.

The reactions shown in Reaction Scheme 2 and resulting GPC curves (not shown) demonstrate the ability of the present invention to fabricate co-polymers. Moving left-to-right across Reaction Scheme 2, in a first reaction, a β-polypeptide homopolymer was fabricated from compound 6 (see the Examples). The resulting homopolymer, shown in the middle of Reaction Scheme 2 had a molecular weight (Mn) of 2,500, and a PDI of 1.13).

Alternatively, a reactive terminal end-group can be used for terminal functionalization of the polymer or a different monomer can be introduced to yield a co-polymer. As shown in the right-hand portion of Reaction Scheme 2, additional monomer was added to the on-going polymerization to alter the ultimate molecular weight of the resulting polymer. The "m+n" co-polymer shown in Reaction Scheme 2 had the following characteristics: Mn=17,300, PDI=1.23. The increased molecular weight of the "m+n" co-polymer of Reaction Scheme 2 as compared to the homopolymer of Reaction Scheme 2 is readily apparent by the leftward shift of the GPC peak of the co-polymer as compared to the GPC peak for the homopolymer. The comparability of the PDIs is also apparent as evidenced by the widths of the two peaks, which are quite similar (PDI=1.13 for the homopolymer, 1.23 for the co-polymer). These data are significant because they demonstrate that the present invention can be used to fabricate β-peptides of vastly different molecular weights (homopolymers, co-polymers, and terminally-functionalized polymers) in a controlled fashion (and without significantly increasing the polydispersity of the resulting polymers). In short, the exemplary reaction depicted in Reaction Scheme 2 yields a relatively small homopolymer and a comparatively far larger co-polymer, yet the PDI's for both products are very similar. See the Examples for a further discussion.

The present inventive reaction is both highly flexible and robust. Unlike past approaches, which are very sensitive to solvent effects and impurities, the present reaction will proceed using a host of low-cost initiators and solvents. The reaction is also robust and tolerant of impurities.

For example, polymerization of cyclooctyl-β-lactam was also tested in the presence of up to 20% mol of water or benzyl amine. The molecular weight and the PDI of the resulting polymers were unaffected relative to analogous reactions without the added water or benzyl amine. In the polymerization of compound 6, using the method of the present invention, product having a PDI less than 1.5 were obtained under a host of less-than-ideal conditions. The general reaction is shown in Reaction Scheme 3:

Reaction Scheme 3

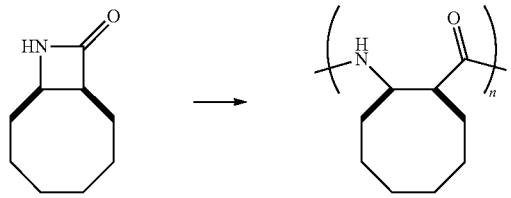

β-polypeptides were fabricated according to Reaction Scheme 3 using bicyclic β-lactam ring-opening anionic polymerization in common solvents including dichloromethane, tetrahydrofuran, and dimethylsulfoxide. The reaction can be initiated using common base initiators, including (without limitation) KOtBu, LiN(TMS)$_2$, and MeONa (in tetrahydrofuran).

Another distinct advantage of the present invention is that it allows a host of functional groups to be incorporated into the resulting polymer (either during the polymerization itself or via subsequent reactions involving reactive side groups post-polymerization.) For example, the β-lactam monomers can include functional groups on the side chains that are hydrophilic, hydrophobic, anionic, cationic, etc. The ratios of these various side chains within the final polymer can be controlled by controlling the relative amounts of each monomer in the co-polymerization reaction. The hydrophobic and cationic co-polymers, which are shown in the Examples, are particularly noteworthy because these side chains contribute to the antibacterial functionality of the polymers. Of course, the side chains can be manipulated to optimize any other desired property of the resulting polymer, be it solubility, biological activity, etc.

Additional monocyclic and bicyclic β-lactam monomers that have been fabricated and polymerized are shown in Reaction Scheme 4 (bicyclic monomers) and Reaction Scheme 5 (monocyclic monomers):

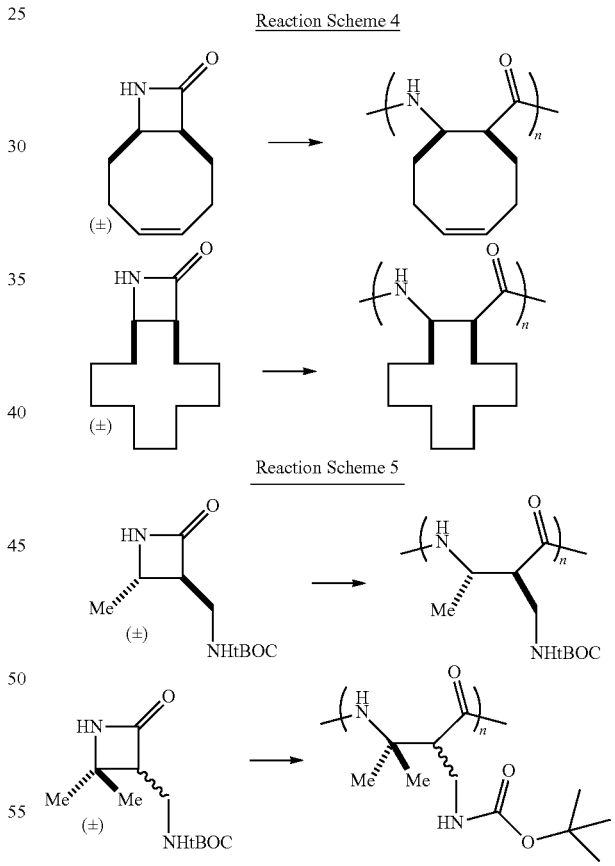

Reaction Scheme 4 illustrates the polymerization of bicyclic β-lactam monomers. Shown in the Reaction Scheme 4 are monomers that include a fused cyclooctene ring and a fused cyclododecane ring. Reaction Scheme 5 illustrates the polymerization of di- and tri-substituted monocyclic β-lactam monomers. The resulting polymers shown in Reaction Schemes 4 and 5 are obtained in high-yield (>90%), with very low molecular weight distributions (PDI's<1.5). See the Examples for further details.

Not all β-lactam-containing monomers will yield soluble products. Note, however, that the invention explicitly encompasses methods that yield soluble or insoluble polymeric products. For example, the following two β-lactam-containing monomers yield insoluble polymers when polymerized according to the present invention:

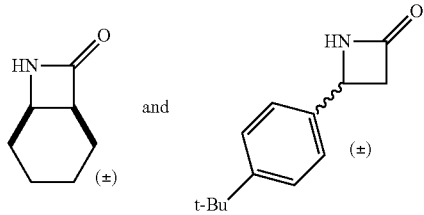

(See the Examples for a complete recitation of the reaction specifics.) Of particular note, however, is that all of these monomers can be readily polymerized in $CH_2Cl_2$ or THF, and the resulting polymers have very small PDIs, generally <1.5.

The synthetic route described herein is highly useful because a number of β-peptides and related compounds have been shown to be antimicrobial. See, for example, the Gellman et al. patents noted in the Background section. Thus, the present inventive method provides a new and robust route to making large quantities of β-peptides for medicinal use.

Additionally, the present invention is useful because it provides a versatile method to polymerize β-lactam-containing monomers under controlled conditions. The resulting polymers can then be used for systematic probing of a large array of polymer structures. For example, the present method allows systematic fabrication of homopolymers of known molecular weight and polydispersity. The method also allows for the systematic fabrication of random and block co-polymers using different combinations of co-monomers, mono-cyclic and bicyclic, including, without limitation, the following β-lactam-containing monomers:

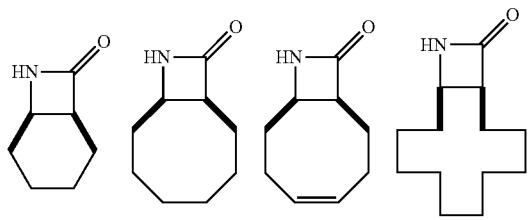

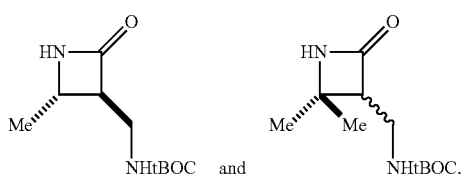

As a result, a whole host of β-peptides can be fabricated systematically, in molecular weights up to and greater than 20 kDa, including homopolymers, for example:

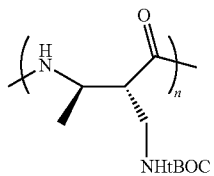

random co-polymers, for example:

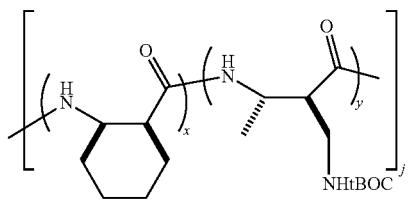

and block co-polymers, for example:

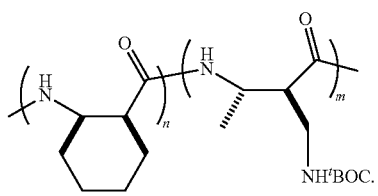

If the ultimate product is to be incorporated into a pharmaceutical composition, notably a synthetic lung surfactant, the composition is preferably formulated by means generally known in the industry. Thus, pharmaceutical compositions according to the present invention comprise an effective amount of a nylon-3 polypeptide or a pharmaceutically acceptable salt thereof together with a pharmaceutically acceptable carrier, typically including one or more lipids for a synthetic lung surfactant composition. Optionally, other therapeutically active substances or accessory agents may be included in addition to the nylon-3 polymer or the salt thereof.

The term "pharmaceutically acceptable salt" refers to any acid or base addition salt whose counter-ions are non-toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, such as polymers containing the MM and DM residues noted in FIG. 1A, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, quinates, and the like. If an acidic side-chain is present, base addition salts include those derived from alkali or alkaline earth metal bases or conventional organic bases, such as triethylamine, pyridine, piperidine, morpholine, N-methylmorpholine, and the like.

The pharmaceutical compositions of the invention comprise an amount of nylon-3 polymer, copolymer, or a pharmaceutically acceptable salt thereof that is effective to pulmonary maladies relating to deficient or dysfunctional lung surfactant in a mammal (including humans). The carrier must be pharmaceutically acceptable in the sense of being compatible with the other ingredients in the particular composition and not deleterious to the recipient of the composition. The compositions generally include those suitable for inhalation or via instillation into the alveoli.

In a particular aspect, the pharmaceutical compositions comprise the active ingredient (a nylon-3 polymer or a pharmaceutically acceptable salt thereof) presented in unit dosage form. The term "unit dosage" or "unit dose" designates a predetermined amount of the active ingredient sufficient to be effective to treat each of the indicated activities. Preferred unit dosage formulations are those containing a daily dose, daily sub-dose, or an appropriate fraction thereof, of the administered active ingredient.

The pharmaceutical compositions may be prepared by any of the methods well known in the art of pharmacy. All methods include the step of bringing the active ingredient into association with a carrier which constitutes one or more accessory ingredients. In general, the compositions are prepared by uniformly and intimately bringing the active ingredient into association with a liquid or solid carrier and then, if necessary, shaping the product into the desired unit dosage form. For inhaled compositions, the unit dosage may be pre-packaged into an inhaler, nebulizer, or the like, or pre-packaged into single-use containers than can be opened and dispensed using an inhaler or nebulizer. The compositions may also be delivered to the lungs intratracheally (via a breathing tube) as a liquid bolus. The compositions may contain conventional adjuvants such as buffers, bacteriostats, viscosity-altering agents, and the like. The compositions may be presented in unit dose or multi-dose containers, for example, sealed vials.

Compositions suitable for inhalation or instillation administration may include a micronized powder (if the carrier is a solid) formulation having a particle size in the range of from about 5 microns or less to about 500 microns, or a liquid formulation, for rapid inhalation through the nasal or oral passage from a conventional inhaler, nebulizer, or the like. Suitable liquid nasal compositions include conventional nasal sprays, nasal drops and the like, of aqueous solutions of the active ingredient and optional adjuvants.

In addition to the aforementioned ingredients, the compositions of this invention may further include one or more optional accessory ingredients(s) utilized in the an of pharmaceutical formulations, e.g., diluents, buffers, flavoring agents, colorants, binders, surfactants, thickeners, lubricants, suspending agents, preservatives (including antioxidants) and the like.

The amount of active ingredient required to be effective for each of the indicated activities will, of course, vary with the individual mammal being treated and is ultimately at the discretion of the medical or veterinary practitioner. The factors to be considered include the species and sex of the mammal, the ailment being treated, the route of administration, the nature of the formulation, the mammal's body weight, surface area, age and general condition, and the particular compound to be administered.

EXAMPLES

Materials: All commercially available compounds were purchased from Sigma-Aldrich (Milwaukee, Wis.) or ACROS (Geel, Belgium) and used as received unless otherwise noted. Peptide and peptoid synthesis reagents and supplies were obtained from Applied Biosystems (ABI) (Foster City, Calif.) and Aldrich. Fmoc-protected amino acids and resins were purchased from EMD Biosciences (NovaBiochem, San Diego, Calif.). Primary amines for peptoid synthesis, highest percent purity and enantiomeric excess available, di-tert-butyl dicarbonate (Boc), and palmitic acid (PA) were obtained from Aldrich. All buffer salts, and solvents acetonitrile, chloroform, methanol, and trifluoroacetic acid (TFA), HPLC grade or better, were purchased from Fisher Scientific (Pittsburgh, Pa.). $CDCl_3$ and DA) for NMR were purchased from Aldrich. DPPC and POPG were obtained from Avanti Polar Lipids (Alabaster, Ala.) and used as received. MTS reagent was purchased from Promega (Madison, Wis.), Hank's Balanced Salt Solution (HBSS) from Lonza (Basel, Switzerland), Dulbecco's Modified Eagle's Media (DMEM) from ATCC or Invitrogen (Carlsbad, Calif.), and the microplate reader from Molecular Devices (Sunnyvale, CA). Water was Milli-Q 18.2 mΩ·cm quality.

Polymerization reactions were carried out in an MBraun UniLab double glove box under a nitrogen atmosphere. Yields refer to chromatographically and spectroscopically pure compounds, unless otherwise stated. Masses of final polymers were confirmed by MALDI-TOF mass spectrometry using a Bruker REFLEX II™ (Billerica, Mass.) spectrometer in positive ion mode (acceleration voltage=25 kV), equipped with a 337 nm laser, a reflectron, and delayed extraction. $^1H$ NMR spectra were obtained on a Broker AC-300 spectrometer at 300 MHz. DMSO-$d_6$. $D_2O$ for NMR was purchased from Aldrich. $^1H$ chemical shifts are reported relative to HOD (δ 4.79) for $D_2O$. Gel permeation chromatography (GPC) was performed on an instrument comprising a Shimadzu LC-10AD liquid chromatography (HPLC) pump and a Wyatt Technology miniDAWN multi-angle light scattering (MALS) detector (690 nm, 30 mW) in series with a Wyatt Technology Optilab-Rex refractive index detector (690 nm). GPC was performed using two Waters columns (Styragel HR4E, particle size 5 μm) with THF (Fisher HPLC-grade, used without further treatment) as mobile phase at a flow rate of 1.0 mL min-1 at 40° C. The refractive index increment (dn/dc) of the polymers was measured in THF at 30° C. using the refractive index detector, and used to determine the $M_n$ and polydispersity (PDI) values of each polymer. The data were processed using ASTRA 5.3.2.15 software (Wyatt Technology).

Characterization of Polymers: The methods for determining molecular weights and polydispersities detailed below have been reported previously.[42]

GPC calculations: The values derived from the GPC data detailed in Table 1 were determined according to the following methods:

Target $M_n$: The target number-average molecular weight ($M_n$) is determined by the following formula:

$$\text{Target } M_n = M_{cg} + a(M_{cat}) + b(M_{cy})$$

where $M_{cg}$ is the mass of the N-terminal end group (e. g. t-$BuC_6H_4$—CO—), $M_{cat}$ is the mass of the cationic monomer, $M_{cy}$ is the mass of the cyclic monomer, a is the total number of cationic monomers, and b is the total number of cyclic monomers in the molecule, such that a+b=the intended degree of polymerization (DP). For example, for the Boc-precursor of polymer 1:1 MM:CO (Table 1), the target $M_n$ is 161.22+10(214.26)+10(153.22)=3836.0.

Obs. $M_n$ and PDI: The observed $M_n$ and polydispersity index (PDI) are determined from the gel-permeation chromatogram of the Boc-protected precursors as described above using Astra® software.

Obs. DP: The observed degree of polymerization was calculated from the observed Mn value using the following formula:

$$DP=(M_n-M_{eg})/[M_{cat}x+M_{cy}(1-x)]$$

where x is the mole fraction of cationic monomer in the feed ratio. The reported number is rounded to the nearest integer. For example, the Boc-precursor of polymer 2:1 MM:CH (Table 1) has an Mn value of 5830 Da by GPC. Its degree of polymerization is (5830−161.22)/[(214.26*0.67)+(125.17*0.33)]=30.7, rounded off to 31 residues.

MALDI calculations: The values derived from the MALDI data detailed in the foregoing table are determined from the highest-intensity mass peak of the spectrum according to the following methods. We do not calculate any average molecular weight or polydispersity information from the MALDI spectrum because the largest members of the polymer population are underrepresented, and the recorded spectrum cannot be assumed to be representative of the population as a whole. All information regarding polymer size is calculated only for the mass peak identified.

MALDI Target MW: The target MW value for the final compounds is calculated the same way as for the Boc-precursors, except using the mass of the deprotected cationic monomer for Me m, and using exact masses.

MALDI Obs. DP: The degree of polymerization corresponding to the highest-intensity mass peak is calculated after determining the ratio of cationic to cyclic monomer corresponding to that mass. The ratio is determined as follows:

$$\text{Obs. } m/z=M_{eg}+a(M_{cat})+b(M_{cy})+M_{ion}$$

where $M_{ion}$ is the mass of the complexed ion in the volatile species. The integers a and b are varied until the calculated mass is obtained, and the mass of the complexed ion (or water) is added only if it results in a more exact mass than can be obtained without. For example, the highest-intensity mass of polymer 2:1 DM:CH (Table 1) corresponds to a 22-mer: 161.10+14(128.10)+8(125.08)+38.964 (for $K_+$)=2994.1 (the nearest calculated value to the observed m/z). Masses corresponding to $(M+H_2O)_+$ may indicate a polymer molecule where the C-terminal β-lactam has been hydrolyzed to a carboxylic acid.

TABLE 1

Molecular weights and polydispersities of p-(t-butyl)benzamide nylon-3 copolymers and their Boc-protected precursors. All polymers' target degree of polymerization was 20.

| | GPC Data for Boc-Polymers | | | | MALDI data for final polymers[a] | | |
| --- | --- | --- | --- | --- | --- | --- | --- |
| Polymer | Target Mn | Obs. Mn (Da)[b] | PDI[b] | Obs. DP[c] | Target Mn | Highest AI m/z | Obs. DPc (cat:cycl) |
| MM homopolymer | 4447 | Ins[d] | — | — | 2443 | 2005 | 16 (16:0) |
| DM homopolymer | 4727 | 6380 | 1.08 | ~27 | 2723 | 4190 | 31 (31:0 + K + H2O) |
| 1:2 MM:DM | 4640 | 6560 | 1.18 | ~29 | 2636 | NS[e] | — |
| 2:1 MM:DM | 4546 | 6510 | 1.14 | ~29 | 2542 | NS[e] | — |
| 1:2 MM:CH | 3259 | 5880 | 1.04 | ~37 | 2516 | 2649 | 20 (1:19) |
| 2:1 MM:CH | 3852 | 5830 | 1.06 | ~31 | 2589 | 2335 | 18 (7:11) |
| 2:1 DM:CH | 4040 | 6350 | 1.07 | ~32 | 2703 | 2993 | 22 (14:8 + K) |
| 1:1 MM:CO | 3836 | 5170 | 1.07 | ~27 | 2833 | 2678 | 20 (14:6 + H) |
| 1:2 MM:CO a | 3633 | 5250 | 1.06 | ~29 | 2963 | 2564 | 19 (13:6 + H) |
| 1:2 MM:CO b | 3633 | 6360 | 1.06 | ~36 | 2963 | 3197 | 22 (9:13 + H2O) |
| 1:2 MM:CO c | 3633 | 4780 | 1.06 | ~26 | 2963 | 2814 | 21 (15:6 + Na) |
| C18-1:2 MM:CO | 3739 | 5640 | 1.05 | ~31 | 3069 | 3050 | 22 (16:6 + H2O + Na) |
| 2:1 MM:CO a | 4040 | 5110 | 1.07 | ~25 | 2703 | 2300 | 16 (9:7 + Na + H2O) |
| 2:1 MM:CO b | 4040 | 5260 | 1.08 | ~26 | 2703 | 2300 | 16 (9:7 + Na + H2O) |
| 1:1 DM:CO a | 3976 | 7100 | 1.06 | ~36 | 2973 | 3363 | 22 (7:15 + Li) |
| 1:1 DM:CO b | 3976 | 5590 | 1.09 | ~28 | 2973 | 2647 | 17 (5:12 + Li) |
| 1:1 DM:CO c | 3976 | 7340 | 1.06 | ~38 | 2973 | 2799 | 20 (17:3 + H) |
| C18-1:1 DM:CO | 4083 | 6140 | 1.05 | ~31 | 3079 | 2817 | 18 (9:9 + H2O) |
| 2:1 DM:CO a | 4227 | 6110 | 1.11 | ~29 | 2890 | 2965 | 21 (18:3 + K) |
| 2:1 DM:CO b | 4227 | 5670 | 1.15 | ~27 | 2890 | 3006 | 20 (9:11 + Li) |

[a]Molecular weight assignments by MALDI were based on the highest-intensity mass peaks from the spectrum.
[b]$M_n$ and PDI were calculated as described previously using Astra ® software.2
[c]DP = degree of polymerization.
[d]Ins = insoluble in THF, therefore preventing collection of GPC data.
[e]NS = no spectrum was produced.

For most of the MALDE masses reported in Table 1, the ratio of monomers indicated may not correlate with the ratio of monomers in the polymerization feed. It cannot be assumed that all polymer molecules are volatilized with the same intensity, nor can it be assumed that all polymer molecules possess the same ratio of monomers as the feed. The ratio, 2:1 MM:CH for example. refers to the ratio of monomers in the entire population of molecules; individual ratios may vary from molecule to molecule.

Pulsating Bubble Surfactometry Data, Batch-to-Batch Reproducibility. Polymer activities were re-evaluated in subsequent batches in PBS static- and dynamic-bubble mode, as well as for toxic effects against NIH 3T3 fibroblasts. It should be noted that even the largest inter-batch variations did not alter the conclusions of the work. The labor-intensive nature of sample preparation, the PBS assays, and the cytotoxicity experiments precluded evaluating inter-batch variation for every polymer. However, observations, on the whole, indicate that inter-batch variation was minimal, and in almost every case, polymer activities were reproduced within the range of uncertainty for the experiments. See Tables 2-6:

TABLE 2

PBS Adsorption Data at Selected Time Intervals of Originally Synthesized Polymers, 37° C.

| Film | γ* 1 min Avg | σ† | γ 2.5 min Avg | σ | γ 5 min Avg | σ | γ 10 min Avg | σ | γ$_{eq}$ 20 min Avg | σ |
|---|---|---|---|---|---|---|---|---|---|---|
| TL‡ | 61.8 | 1.6 | 58.5 | 1.7 | 55.8 | 1.8 | 53.2 | 1.7 | 50.7 | 1.7 |
| TL + MM¥ | 45.9 | 3.7 | 44.9 | 2.8 | 44.0 | 2.6 | 43.6 | 2.6 | 43.2 | 3.0 |
| TL + DM | 39.3 | 3.1 | 37.8 | 3.6 | 36.8 | 4.2 | 35.7 | 4.6 | 34.6 | 4.4 |
| TL + 1:2 MM:DM | 43.7 | 2.7 | 42.8 | 2.3 | 41.7 | 2.1 | 40.6 | 1.9 | 39.4 | 2.1 |
| TL + 2:1 MM:DM | 48.1 | 1.8 | 46.7 | 1.5 | 45.3 | 1.1 | 44.4 | 1.4 | 43.6 | 1.4 |
| TL + 1:2 MM:CH | 39.3 | 2.3 | 35.0 | 2.5 | 33.8 | 2.5 | 32.7 | 2.4 | 31.6 | 1.2 |
| TL + 2:1 MM:CH | 43.0 | 2.5 | 41.3 | 1.8 | 39.7 | 1.5 | 37.1 | 2.6 | 32.8 | 3.4 |
| TL + 2:1 DM:CH | 36.6 | 2.2 | 34.1 | 2.3 | 32.0 | 0.9 | 30.4 | 1.1 | 29.2 | 1.5 |
| TL + 1:1 MM:CO | 35.4 | 0.8 | 32.4 | 0.7 | 30.4 | 0.7 | 28.8 | 0.5 | 26.1 | 0.6 |
| TL + 1:1 MM:CO | 30.1 | 2.0 | 28.1 | 1.5 | 26.5 | 1.2 | 25.7 | 0.2 | 25.8 | 0.3 |
| TL + 2:1 MM:CO | 38.7 | 2.8 | 36.1 | 4.9 | 34.8 | 5.3 | 33.5 | 4.9 | 30.7 | 3.2 |
| TL + 1:1 DM:CO | 29.5 | 1.1 | 27.1 | 0.7 | 25.9 | 0.4 | 25.7 | 0.5 | 25.2 | 0.8 |
| TL + 2:1 DM:CO | 33.5 | 2.9 | 30.8 | 2.7 | 28.2 | 1.6 | 26.9 | 1.1 | 25.7 | 0.4 |
| TL + SP-B1-25 | 40.5 | 1.2 | 39.4 | 1.9 | 37.9 | 1.2 | 36.8 | 1.0 | 35.6 | 1.3 |
| TL + KL4 | 27.7 | 0.8 | 24.7 | 1.3 | 22.4 | 0.7 | 22.4 | 0.7 | 21.6 | 0.8 |
| TL + Peptoid B1 | 44.6 | 3.0 | 42.5 | 2.8 | 40.7 | 2.3 | 39.2 | 1.9 | 38.1 | 1.2 |

*Mean surface tension in mN m−1
‡Tanaka lipid mixture, DPPC:POPG:PA 68:22:9 [wt]
¥Mimics added at 10 wt % relative to the total lipid content
†σ is the standard deviation of the mean

TABLE 3

PBS Adsorption Data at Selected Time Intervals of Re-Synthesized Polymers, 37° C.

| Film | γ* 1 min Avg | σ† | γ 2.5 min Avg | σ | γ 5 min Avg | σ | γ 10 min Avg | σ | γ$_{eq}$ 20 min Avg | σ |
|---|---|---|---|---|---|---|---|---|---|---|
| TL‡ | 61.8 | 1.6 | 58.5 | 1.7 | 55.8 | 1.8 | 53.2 | 1.7 | 50.7 | 1.7 |
| TL + 1:2 MM:CO a¥ | 30.1 | 2.0 | 28.1 | 1.5 | 26.5 | 1.2 | 25.7 | 0.2 | 25.8 | 0.3 |
| TL + 1:2 MM:CO b | 30.5 | 1.2 | 28.8 | 1.2 | 26.2 | 1.5 | 25.0 | 0.5 | 24.3 | 0.2 |
| TL + 1:1 MM:CO c | 29.3 | 1.5 | 27.6 | 2.3 | 25.9 | 0.9 | 24.6 | 0.8 | 23.4 | 1.9 |
| TL + C18-1:2 MM:CO | 30.0 | 1.9 | 27.7 | 1.6 | 25.0 | 0.7 | 24.5 | 0.9 | 24.1 | 2.3 |
| TL + 2:1 MM:CO a | 38.7 | 2.8 | 36.1 | 4.9 | 34.8 | 5.3 | 33.5 | 4.9 | 30.7 | 3.2 |
| TL + 2:1 MM:CO b | 48.5 | 0.5 | 45.4 | 0.7 | 42.1 | 0.5 | 39.6 | 0.9 | 36.1 | 2.6 |
| TL + 1:1 DM:CO a | 29.5 | 1.1 | 27.1 | 0.7 | 25.9 | 0.4 | 25.7 | 0.5 | 25.2 | 0.8 |
| TL + 1:1 DM:CO b | 29.0 | 0.9 | 27.0 | 1.0 | 25.3 | 1.3 | 24.8 | 0.9 | 24.5 | 1.2 |
| TL + 1:1 DM:CO c | 29.6 | 0.9 | 26.9 | 0.8 | 25.1 | 0.5 | 24.4 | 0.7 | 22.8 | 1.5 |
| TL + C18-1:1 DM:CO | 28.6 | 0.5 | 26.4 | 0.3 | 24.6 | 0.4 | 24.2 | 0.2 | 23.9 | 0.3 |
| TL + 2:1 DM:CO a | 33.5 | 2.9 | 30.8 | 2.7 | 28.2 | 1.6 | 26.9 | 1.1 | 25.7 | 0.4 |
| TL + 2:1 DM:CO b | 33.7 | 1.5 | 31.0 | 1.0 | 28.8 | 0.7 | 26.1 | 0.2 | 24.2 | 0.4 |

*Mean surface tension in mN m−1
‡Tanaka lipid mixture, DPPC:POPG:PA 68:22:9 [wt]
¥Mimics added at 10 wt % relative to the total lipid content
†σ is the standard deviation of the mean

TABLE 4

PBS Dynamic Data at Selected Time Intervals of Originally Synthesized Polymers, 37° C.

| Film | 1 min γ max Avg | σ | γ min Avg | σ | 2.5 min γ max Avg | σ | γ min Avg | σ | 10 min γ max Avg | σ | γ min Avg | σ |
|---|---|---|---|---|---|---|---|---|---|---|---|---|
| TL‡ | 60.8 | 2.8 | 15.0 | 2.5 | 61.0 | 2.4 | 14.3 | 2.9 | 60.1 | 2.3 | 12.0 | 2.9 |
| TL + MM¥ | 49.9 | 1.3 | 7.95 | 3.63 | 49.7 | 1.4 | 6.38 | 2.38 | 48.1 | 1.7 | 5.03 | 1.41 |
| TL + DM | 46.3 | 0.7 | 5.84 | 2.57 | 46.0 | 0.7 | 5.10 | 1.83 | 44.2 | 1.4 | 5.75 | 1.93 |
| TL + 1:2 MM:DM | 47.9 | 0.7 | 3.11 | 3.0 | 47.4 | 0.9 | 2.62 | 2.36 | 45.9 | 0.8 | 2.62 | 2.89 |
| TL + 2:1 MM:DM | 47.9 | 1.3 | 7.79 | 2.58 | 47.6 | 1.4 | 7.43 | 3.12 | 46.9 | 0.6 | 5.37 | 1.70 |
| TL + 1:2 MM:CH | 47.4 | 0.8 | <1 | — | 47.3 | 0.8 | <1 | — | 47.5 | 0.6 | <1 | — |
| TL + 2:1 MM:CH | 48.1 | 1.9 | 2.72 | 2.44 | 46.9 | 1.0 | 3.08 | 2.67 | 44.3 | 1.1 | 3.03 | 2.63 |

TABLE 4-continued

PBS Dynamic Data at Selected Time Intervals of Originally Synthesized Polymers, 37° C.

| | 1 min | | | | 2.5 min | | | | 10 min | | | |
|---|---|---|---|---|---|---|---|---|---|---|---|---|
| | γ max | | γ min | | γ max | | γ min | | γ max | | γ min | |
| Film | Avg | σ | Avg | σ | Avg | σ | Avg | σ | Avg | σ | Avg | σ |
| TL + 2:1 DM:CH | 44.6 | 1.0 | 2.81 | 0.54 | 44.0 | 1.3 | 3.08 | 0.63 | 42.5 | 1.5 | 4.45 | 0.60 |
| TL + 1:1 MM:CO | 44.0 | 0.4 | <1 | — | 43.9 | 0.6 | <1 | — | 42.8 | 0.2 | <1 | — |
| TL + 1:1 MM:CO | 43.1 | 1.2 | <1 | — | 42.5 | 0.7 | <1 | — | 44.5 | 1.3 | <1 | — |
| TL + 2:1 MM:CO | 45.7 | 0.6 | 1.67 | 1.97 | 44.9 | 0.7 | 1.84 | 1.53 | 42.2 | 1.5 | 2.47 | 1.95 |
| TL + 1:1 DM:CO | 39.5 | 0.7 | <1 | — | 39.3 | 1.1 | <1 | — | 42.0 | 2.6 | <1 | — |
| TL + 2:1 DM:CO | 41.4 | 1.2 | <1 | — | 40.1 | 1.5 | <1 | — | 39.6 | 2.6 | <1 | — |
| TL + SP-B1-25 | 49.6 | 0.5 | <1 | — | 49.9 | 0.7 | <1 | — | 49.8 | 0.7 | <1 | — |
| TL + KL4 | 47.2 | 1.3 | <1 | — | 47.9 | 1.2 | <1 | — | 48.2 | 1.3 | <1 | — |
| TL + Peptoid B1 | 48.9 | 1.7 | <1 | — | 49.2 | 1.6 | <1 | — | 49.0 | 1.6 | <1 | — |

*Mean surface tension in mN m−1
‡Tanaka lipid mixture, DPPC:POPG:PA 68:22:9 [wt]
¥Mimics added at 10 wt % relative to the total lipid content
†σ is the standard deviation of the mean. No σ values are available for "<1" table entries.

TABLE 5

PBS Dynamic Data at Selected Time Intervals of Re-Synthesized Polymers, 37° C.

| | 1 min | | | | 2.5 min | | | | 10 min | | | |
|---|---|---|---|---|---|---|---|---|---|---|---|---|
| | γ max | | γ min | | γ max | | γ min | | γ max | | γ min | |
| Film | Avg | σ | Avg | σ | Avg | σ | Avg | σ | Avg | σ | Avg | σ |
| TL‡ | 60.8 | 2.8 | 15.0 | 2.5 | 61.0 | 2.4 | 14.3 | 2.9 | 60.1 | 2.3 | 12.0 | 2.9 |
| TL + 1:2 MM:CO a¥ | 43.1 | 1.2 | <1 | — | 42.5 | 0.7 | <1 | — | 44.5 | 1.3 | <1 | — |
| TL + 1:2 MM:CO b | 42.6 | 0.8 | <1 | — | 41.8 | 0.2 | <1 | — | 40.9 | 0.3 | <1 | — |
| TL + 1:1 MM:CO c | 43.6 | 0.7 | <1 | — | 43.7 | 1.3 | <1 | — | 44.2 | 0.8 | <1 | — |
| TL + C18-1:2 MM:CO | 42.1 | 0.8 | <1 | — | 41.2 | 0.3 | <1 | — | 40.0 | 0.0 | <1 | — |
| TL + 2:1 MM:CO a | 45.7 | 0.6 | 1.67 | 1.97 | 44.9 | 0.7 | 1.84 | 1.53 | 42.2 | 1.5 | 2.47 | 1.95 |
| TL + 2:1 MM:CO b | 48.3 | 0.8 | <1 | — | 47.5 | 0.8 | <1 | 0.8 | 45.8 | 1.5 | <1 | — |
| TL + 1:1 DM:CO a | 39.5 | 0.7 | <1 | — | 39.3 | 1.1 | <1 | — | 42.0 | 2.6 | <1 | — |
| TL + 1:1 DM:CO b | 43.0 | 0.4 | <1 | — | 41.9 | 0.2 | <1 | — | 42.0 | 0.5 | <1 | — |
| TL + 1:1 DM:CO c | 42.8 | 0.9 | <1 | — | 42.5 | 0.7 | <1 | — | 42.7 | 0.4 | <1 | — |
| TL + C18-1:1 DM:CO | 38.3 | 1.2 | <1 | — | 37.6 | 0.9 | <1 | — | 37.5 | 1.0 | <1 | — |
| TL + 2:1 DM:CO a | 41.4 | 1.2 | <1 | — | 40.1 | 1.5 | <1 | — | 39.6 | 2.6 | <1 | — |
| TL + 2:1 DM:CO b | 43.4 | 0.5 | <1 | — | 42.7 | 0.7 | <1 | — | 41.3 | 0.5 | <1 | — |

*Mean surface tension in mN m−1
‡Tanaka lipid mixture, DPPC:POPG:PA 68:22:9 [wt]
¥Mimics added at 10 wt % relative to the total lipid content
†σ is the standard deviation of the mean. No σ values are available for "<1" table entries.

TABLE 6

Percent Bubble Surface Area Compression Required to Reach 20 mN m-1 Upon Compression, at 5 minutes of Dynamic-Bubble Pulsation on the PBS, 37° C.

| Film | Avg % Comp | σ† |
|---|---|---|
| TL | 42.5 | 2.9 |
| TL + MM | 31.1 | 4.6 |
| TL + DM | 27.0 | 1.5 |
| TL + 1:2 MM:DM | 28.8 | 1.3 |
| TL + 2:1 MM:DM | 29.5 | 2.5 |
| TL + 1:2 MM:CH | 28.3 | 1.4 |
| TL + 2:1 MM:CH | 30.5 | 1.3 |
| TL + 2:1 DM:CH | 28.3 | 2.2 |

TABLE 6-continued

Percent Bubble Surface Area Compression Required to Reach
20 mN m-1 Upon Compression, at 5 minutes of Dynamic-Bubble
Pulsation on the PBS, 37° C.

| Film | Avg % Comp | σ† |
|---|---|---|
| TL + 1:1 MM:CO | 23.9 | 2.0 |
| TL + 1:2 MM:CO a | 22.4 | 3.0 |
| TL + 1:2 MM:CO b | 16.4 | 0.7 |
| TL + 1:2 MM:CO c | 22.0 | 3.8 |
| TL + C18-1:2 MM:CO | 13.9 | 1.5 |
| TL + 2:1 MM:CO a | 26.4 | 1.8 |
| TL + 2:1 MM:CO b | 29.5 | 2.1 |
| TL + 1:1 DM:CO a | 17.5 | 3.1 |
| TL + 1:1 DM:CO b | 21.1 | 1.5 |
| TL + 1:1 DM:CO c | 20.9 | 3.8 |
| TL + C18-1:1 DM:CO | 11.6 | 2.1 |
| TL + 2:1 DM:CO a | 18.4 | 1.3 |
| TL + 2:1 DM:CO b | 23.2 | 2.0 |
| TL + SP-B1-25 | 33.2 | 2.7 |
| TL + KL4 | 24.9 | 3.7 |
| TL + Peptoid B1 | 31.4 | 1.2 |

† σ is the standard deviation of the mean. No σ values are available for "<1" table entries.

Peptide and Peptoid Synthesis and Purification: The modified peptide SP-$B_{1-25}$ (Cys8,11→Ala)[20,21,26,27] and the $KL_4$ peptide[20,21,53] were synthesized by standard SPPS[62] Fmoc chemistry on a 0.25 mmol scale using preloaded Wang resin and an ABI 433A automated peptide synthesizer. Peptoid B1[20,21] was synthesized by the submonomer method[36] using Rink amide resin on a 0.25 mmol scale, and an ABI 433A, with Boc protection of N-(4-aminobutyl)glycine (NLys). SP-$B_{1-25}$, $KL_4$, and Peptoid B1 were cleaved from their respective resins by agitation in 90-95% TFA/water [v/v], along with the appropriate scavengers, for 10 minutes up to 1 hour. Crude product for purification was obtained by immediate resin filtration of the mixture, dilution with ACN/water, repeated lyophilization, and re-dissolution in ACN/water. SP-$B_{1-25}$, $KL_4$, and Peptoid B1 were purified on a Waters (Waters Corp., Milford, MA) RP-HPLC system with a Grace Vydac (Deerfield, Ill.) C4-silica column. All SPPS-based molecules were purified using a linear gradient of percent solvent B in percent solvent A over a selected time period (solvent A is 0.1% TFA in water [v/v] and solvent B is 0.1% TFA in ACN [v/v]), using standard purification techniques. Final purities were confirmed to be >97% by analytical RP-HPLC and molecular weights were obtained by either electrospray ionization mass spectrometry (ESI/MS) or matrix-assisted laser desorption/ionization time-of-flight mass spectrometry (MALDI-TOF/MS) (MW (Da) calc:found as follows: SP-$B_{1-25}$, 2865.55:2865.30; $KL_4$, 2469.40:2469.70; Peptoid B1, 2592.40:2592.50).

Polymer Synthesis and Characterization: Polymers were synthesized using previously reported procedures,[40,46] and detailed polymer characterization (MALDI-TOF/MS, GPC, and $^1$H NMR) are available. See also the Examples provided below.

Surfactant Sample Preparation: The lipids DPPC, POPG, and PA were individually dissolved in a chloroform/methanol solution (3/1 [v/v]) to a known concentration (~2 or 4 mg $mL^{-1}$). Single-lipid solutions were then combined by volume at the ratio of DPPC:POPG:PA, 68:22:9 [wt:wt:wt] and to a known total lipid concentration (~2 mg $mL^{-1}$). This well-characterized and well-known lipid formulation is considered an adequate mimic of the non-protein (lipid) fraction of LS.[45] The peptides, peptoid, and copolymers were individually dissolved in methanol from a lyophilized powder to a known concentration (1-2 mg $mL^{-1}$). For the PBS studies, the peptides, peptoids, and polymers were 'spiked' into the lipid mixture at 10 wt % relative to the total lipid content (9.1 absolute wt %), and to a final concentration of ~1 mg $mL^{-1}$. For comparative purposes, the inclusion of peptide/peptoid/copolymer at 10 wt % corresponds to 10 wt % SP-$B_{1-25}$ (9.1 absolute wt %) relative to the total lipid content. The total combined protein fraction in natural LS is estimated to be ~10 wt %.[18] For PBS experiments, all σ reported is the standard deviation of the mean.

Pulsating Bubble Surfactometry: A commercial PBS instrument (General Transco, Largo, Fla.), modified with a direct, real-time imaging system, which has been previously described and validated in detail,[44] was utilized to obtain both static-mode and dynamic-mode data. Samples were dried from chloroform/methanol 3/1 [v/v] in Eppendorf tubes using a DNA 120 speedvac (Thermo Electron, Holbrook, N.Y.), forming a pellet. The pellet was suspended in buffer (150 mM NaCl, 10 mM HEPES, 5 mM $CaCl_2$, pH 6.9) to 1.0 mg lipid $mL^{-1}$, with a final known volume of ~70 μL. The samples were then mixed with a pipette 20 times, sonicated with a Fisher Model 60 probe sonicator for two 15 second spurts, and then mixed again 20 times to form a dispersed suspension. Samples were then loaded into a small plastic sample chamber (General Transco) using a modified leak-free methodology.[43,44] The sample chamber was then placed in the instrument, surrounded by a water bath held at 37° C. A bubble with a radius of 0.4 mm was then formed, and surface area was monitored throughout the experiment. Bubble size gradually increased in both data collection modes, but had a negligible effect on γ.

Figure 5:
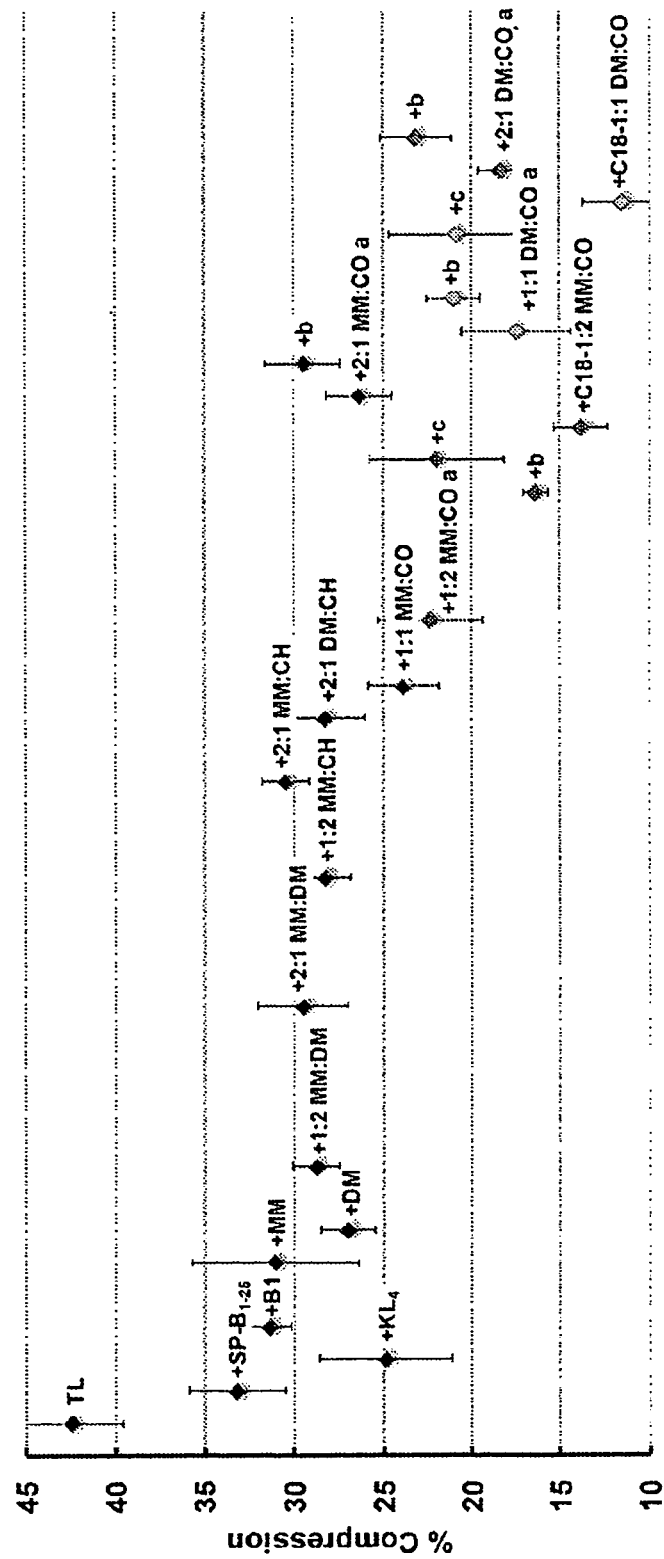
FIG. 5 is a graph depicting PBS percent compression data for films in dynamic-bubble mode at 5 minutes at 37° C. The corresponding mean percent surface area (SA) compression (percent compression) to reach 20 mN m$^{-1}$ at 5 minutes pulsation is depicted. Percent compression is defined here as $100*[(SA_{max}-SA_{20})/(SA.)]$, where $SA_{max}$ was the maximum bubble surface area (SA) at expansion, and $SA_{20}$ was the SA at which γ first reaches 20 mN m$^{-1}$ upon compression at 5 minutes pulsation. Error bars are the standard deviation of the mean (σ). See Tables 4-6 for mean dynamic γ data±σ at selected time intervals and tabulated % Compression data±σ.

Static-mode adsorption data were collected for 20 minutes, where the suspension was allowed to adsorb to the bubble surface over time. Adsorption data were smooth fit to a curve in the Kaleidagraph program by applying a Stineman function to the data, where the output of this function then had a geometric weight applied to the current point and ±10% of the data range to arrive at the smoothed curve (see FIG. 2). Dynamic-mode data were then subsequently obtained for each sample at the adult respiratory cycle frequency of 20 cpm for 10 minutes, with a 50% reduction in surface area per pulsation cycle. PBS experiments were repeated three to six times for each sample to ensure repeatability. Representative PBS loops are presented at five minutes of cycling, and indicate clockwise bubble expansion and counterclockwise compression (see FIGS. 6A, 6B, 6C, and 6D). Average γ±σ at selected time intervals are listed in the Examples for both data collection modes. Percent compression is defined here as $100*[(SA_{max}-SA_{20})/(SA_{max})]$, where $SA_{max}$ was the maximum SA value at expansion, and $SA_{20}$ was the SA at which γ first reaches 20 mN $m^{-1}$ upon compression (FIG. 5).

Cytotoxicity (MTS) Assay: The cytotoxicities of SP-$B_{1-25}$, Peptoid B1, and select copolymers against NIH/3T3 fibroblast cells were evaluated using a 3-(4,5-diemethylthiazol-2-yl)-5-(3-carboxymethoxyphenyl)-2-(4-sulfophenyl)-2H-tetrazolium salt (MTS) (Promega) colorimetric assay. NIH/3T3 fibroblast cells (ATCC, Manassas, Va.) were cultured at 37° C. and 5% $CO_2$ in Dulbecco's Modified Eagle's Media (DMEM) (ATCC or Invitrogen) supplemented with 1% sodium pyruvate, 1% penicillin-streptomycin, 1.5 g $L^{-1}$ $NaHCO_3$, and 10% fetal bovine serum (cDMEM). Cells were seeded at a density of 5,000 cells per well for NIH/3T3 cells in 96-well plates (100 μL, total volume). A SP-$B_{1-25}$ peptide, Peptoid B1, or copolymer solution plate (100 μl per well) was prepared by serial dilution of aqueous peptide or copolymer stock solutions of known concentration (~5 mg $mL^{-1}$) in Hank's Balanced Salt Solution (HBSS) (Lonza). A day-old monolayer of cells plated at 5000 cells per well (100 μl) was washed once, and the media was replaced with HBSS to minimize interference with absorbance readings. Peptide, peptoid, or copolymer solutions were then transferred to corresponding wells of the cell plate. 40 μl MTS reagent (Promega) was then added to each well, and the plate was subsequently incubated at 37° C. for 3 h, after which UV/Vis (Molecular Probes) absorbance measurements at λ~490 nm were recorded. Percent inhibition=[1−(A−$A_{test\ blank}$)/($A_{control}$−$A_{blank}$)]*100, where A is the UV/Vis absorbance of the test well, and $A_{control}$ is the average absorbance of wells with cells exposed to media and MTS (no peptide or copolymer). $A_{test\ blank}$ (media, MTS, and peptide or copolymer) and $A_{blank}$ (media and MTS) were background absorbances measured in the absence of cells. Results are reported as the inhibitory dose (μg mL$^{-1}$) at which 50% of cells experienced metabolic inhibition (ID50). The average of six replicates is reported, where error is the standard error of the mean (SEM) (see FIG. 7).

Results

Copolymer Design, Synthesis, and Characterization: All monomers and polymers described here were prepared using previously reported procedures;[40,42,46] their chemical structures are presented in FIGS. 1A and 1B, respectively. The main variables in copolymer design were N-terminal modification and subunit composition. The β-lactams employed herein gave rise both to lipophilic subunits, CH (for "cyclohexyl") or CO ("cyclooctyl"), and to cationic subunits, MM ("monomethyl") and DM ("dimethyl"). Incorporation of these subunits ensured that the polymers bear a net positive charge in aqueous solution and are amphiphilic. as is true of SP-B itself. However, in contrast to SP-B, the subject polymers cannot achieve global segregation of lipophilic and cationic side chains by adopting a specific and regular conformation, because the sequence of lipophilic and cationic subunits varies among polymer molecules. In addition, because the β-lactam monomers are racemic, stereochemistry varies among polymer chains.

The CH and CO subunits in the present nylon-3 copolymers were intended to mimic the roles of lipophilic side chains and cyclically constrained residues in SP-B. The so-called "insertion region" of human SP-B, residues 1-9, contains a high proportion of residues that are aromatic and lipophilic (Phe1, Tyr5, and Trp8) or that are cyclically constrained (Pro2, Pro4, and Pro6). In previous work, this region was shown to be critical for the γ-reducing behavior of SP-B.[47,48] Furthermore, when aromatic residues or prolines were substituted with alanine, the resulting peptides showed significantly decreased surface activity.[48] It has been hypothesized that the N-terminal region of SP-B inserts transiently into the lipid layer with Trp as an anchor,[49] thus allowing the protein to function overall as a lipid organizer and transporter.

The designations employed for the nylon-3 polymers (FIG. 1B) indicate the subunit identities and proportions, the latter determined by the ratio of β-lactams used in the polymerization reaction. The subunit sequence is random within the copolymers, and because the β-lactams were racemic, each polymer sample contains a mixture of backbone configurations. Most of the polymers have a p-(cert-butyl)benzoyl group at the N-terminus, but two of the copolymers were prepared with an octadecanoyl group at the N-terminus in an attempt to introduce an SP-C-like lipophilic tail into the SP-B mimetic polymers described herein. Peptoid-based SP-C analogues that bear one or two octadecyl groups at the N-terminus have previously been examined.[50] The favorable impact of the lipophilic tail(s) on surface activity prompted an examination of similar modifications of peptoid-based SP-B analogues, and again a marked improvement in surfactant activities relative to unalkylated analogues was observed.[30] These findings with sequence-specific surfactant protein mimics led to an exploration of analogous N-terminal modifications of nylon-3 copolymers.

The β-lactams required for nylon-3 copolymer synthesis were prepared by previously published methods involving the [2+2] cycloaddition of chlorosulfonyl isothiocyanate (CSI) to alkenes. Anionic ring-opening copolymerization of the β-lactams[51,52] followed by acid-mediated removal of the t-butylcarbamate protecting groups yielded nylon-3 materials that are cationic at neutral pH.[40] Gel permeation chromatography (GPC) performed before deprotection indicated polydispersity indices (PDI) in the range 1.04-1.18 (see the Examples). Polydispersity could not be measured after side chain deprotection, but it is assumed that this process does not alter polydispersity. NMR measurements suggested that deprotection reactions proceeded to completion.

Copolymers identified as promising in early PBS screenings (1:2 and 2:1 MM:CO, and 1:1 and 2:1 DM:CO) were re-synthesized to establish the reproducibility of the polymer preparation protocol, as manifested in surface activity and cytotoxicity. For these polymers, different batches are denoted as a, b and c.

Pulsating Bubble Surfactometry: Static-Bubble Mode. The immediate adsorptive, γ-reducing effect, and stability of the films over time at a bubble all interface were assessed via PBS in static-bubble mode. Polymers dried with lipids (Tanaka Lipids, TL, DPPC:POPG:PA 68:22:9 [wt:wt:wt]) were suspended in aqueous buffer (150 mM NaCl, 10 mM HEPES, 5 mM CaCl$_2$, pH 6.9) at 37° C. and allowed to adsorb to the interface of a 0.40 mm radius bubble for 20 minutes, yielding γ as a function of time. In this study, a mimic is considered very surface-active in the lipid film if it adsorbs to ~25 mN m$^{-1}$ within 1-5 minutes; for instance, Infasurf®, an animal-derived SRT, attains a low γ ~ 23 mN m$^{-1}$ within 1-2 minutes on the PBS,[44] and TL+porcine-derived SP-B films reach ~26 mN m$^{-1}$ at 5 minutes.[30] Select polymer adsorption traces are depicted in FIG. 2, while the adsorbed y of all the lipid films containing polymers and positive controls, including lipids alone (TL), the peptides SP-B$_{1-25}$ and KL$_4$ (the latter is a peptide-based SP-B mimic with broad, biomimetic cationic residue patterning),[53] and aromatic-rich Peptoid B1.[20] are presented at 5 minutes adsorption in FIGS. 3A, 3B, 3C, and 3D. Mean adsorptions (γ)±standard deviation (σ) at selected time intervals for all films are presented in Tables 2 and 3). For static-bubble experiments, relative closeness of γ values for different lipid-polymer films was largely determined by comparing the σ of the mean γ for the films; however, as a guideline, a difference of ≥2 mN m$^{-1}$ among adsorptive γ values of different films is generally considered significant.

Figure 3A:
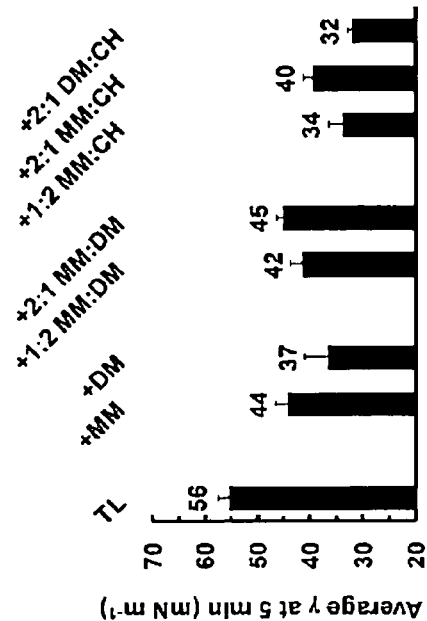
FIGS. 3A, 3B, 3C, and 3D are histograms depicting PBS adsorption data for lipid-polymer films in static-bubble mode at 37° C. Mean γ (mN m$^{-1}$) at 5 minutes adsorption are presented for all films including polymers or positive controls in each of FIGS. 3A-3D. Error bars are the standard deviation of the mean (σ). See Tables 2-3 for mean adsorption γ data±σ at selected time intervals.
Figure 3B:
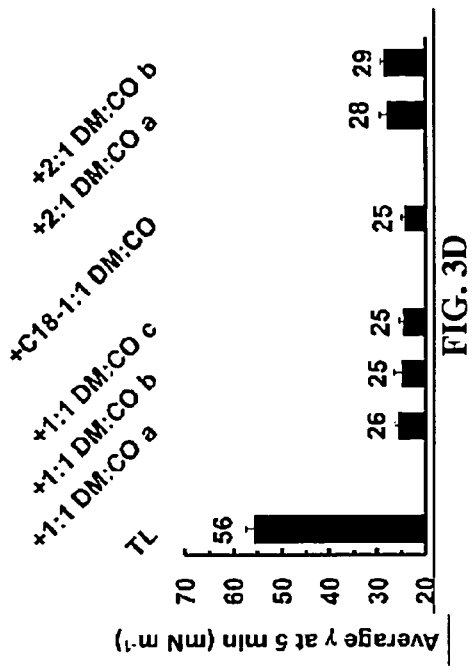
Figure 3C:
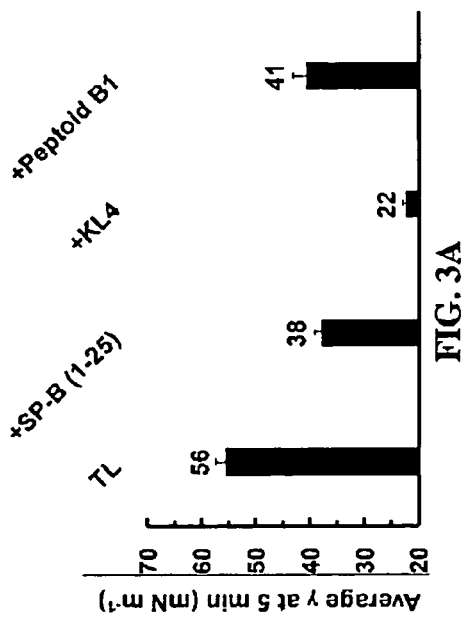
Figure 3D:
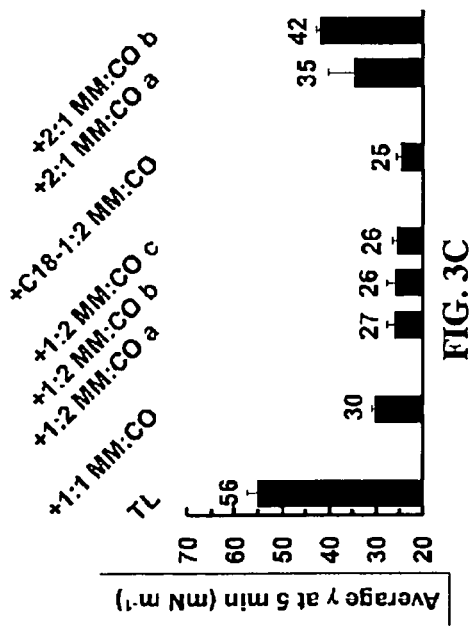

Any additive to the lipid film significantly improved adsorptive characteristics relative to TL alone, with TL+KL$_4$ exhibiting the most positive surfactant activity among the positive controls, reaching 22 mN m$^{-1}$ at 5 minutes (FIG. 3A). Control TL+SP-B$_{1-25}$ was more active than TL+B1, but both were less active than TL+KL4. All of the nylon-3 polymers displayed surface activity in this assay. Among the nylon-3 homopolymers, TL+DM outperformed TL+MM, and an analogous trend was evident among the films containing MM:DM copolymers. The introduction of lipophilic CH subunits to polymers in the lipid films moderately improved adsorption relative to films containing polymers with entirely cationic subunits (MM homopolymer, DM homopolymer, or MM:DM copolymers). Among CH-containing copolymer-lipid films, an increasing proportion of lipophilic subunits (1:2 MM:CH vs. 2:1 MM:CH) or replacement of MM subunits with DM subunits (2:1 DM:CH vs. 2:1 MM:CH) improved surface activity (FIG. 3B).

The best surface activities were observed among films with nylon-3 copolymers containing CO subunits. Both TL+1:1 DM:CO and TL+1:2 DM:CO displayed excellent activities, with γ reaching 26-28 mN m$^{-1}$ after as little as 2.5 minutes of adsorption (FIG. 2; Table 2). Replacing the p-(tert-butyl) benzoyl group at the N-terminus with an octadecanoyl group did not affect PBS static-mode surface activity (films containing 1:1 DM:CO copolymers). Raising the cationic subunit proportion to 67% led to a significant decrease in surface activity, and among these polymers, the use of the DM subunit provided improvement relative to use of the MM subunit (2:1 DM:CO vs. 2:1 MM:CO). In addition, the adsorptive activities of the nylon-3 copolymers were reproduced in subsequent batches (FIGS. 3A-3D).

Pulsating Bubble Surfactometry: Dynamic-Bubble Mode. The dynamic surfactant activity during changes in volume or film surface area provides an indication of film sustainability over time. Bubble pulsation at the approximate adult respiratory rate of 20 cycles per minute (cpm) in PBS dynamic-bubble mode at 37° C. permits a simplified evaluation of such dynamic film behavior.[44] In dynamic mode, after static-bubble adsorption, the bubble was subsequently pulsed for 10 minutes and γ was recorded with respect to surface area. FIGS. 4A, 4B, 4C, and 4D depict the attained maximum and minimum γ ($\gamma_{max/min}$) at 5 minutes of cycling for all lipid films containing polymers or positive controls. Mean $\gamma_{max/min}$'s±σ at selected time intervals for up to 10 minutes of cycling are located in Tables 4 and 5.

Representative single pulsation γ-surface area (SA) bubble hysteresis loops at 5 minutes cycling for select lipid-polymer films are presented in FIGS. 4A-4D. Bubble expansion corresponds to a clockwise loop direction, and vice versa for compression. The absence of low-γ data in some loops is caused by the limited ability of the image analysis system to trace the bubble shape in this regime.[44] The highly compressed state of the film, which enables it to reach near-zero γ, often causes significant bubble shape deformation. This deformation may prevent the level of bubble tracing needed to obtain SA and to calculate γ via the ellipsoidal Laplace equation.[44] However, visual, real-time bubble inspection during the experiment confirmed that γ reached near-zero in these films.[44] In addition, lipid-polymer films that did not reach <1 mN m$^{-1}$ could be accurately traced to the minimum value reported and never exhibited significant bubble deformation. Although bubble size was not uniform for every experiment, differences in x-axis positioning (SA) had no appreciable effect on γ (data not shown).

The key features for good surfactant activity of a film in dynamic-mode are a reduced $\gamma_{max}$ and a $\gamma_{min}$ near zero. The PBS cycling loop for Infasurf® maintains a $\gamma_{max}$ of ~35 mN m$^{-1}$ and a $\gamma_{min}$ near-zero,[44] while the TL+porcine-derived SP-B film exhibits a $\gamma_{max}$ of ~36 mN m$^{-1}$ and near-zero $\gamma_{min}$.[30] To enable normal respiration and minimize the work of breathing, a near-zero $\gamma_{min}$ should occur upon compression of the first cycle, and reduced $\gamma_{max/min}$ values should remain throughout the time tested with minimal SA compression to reach near-zero $\gamma_{min}$. The latter parameter is monitored as percent SA compression to reach 20 mN m$^{-1}$, and is graphically represented in FIG. 5. Tabulated data are presented in Table 6. The TL+SP-B film displayed ~21% compression to reach 20 mN m$^{-1}$.[30]

Although the significance of $\gamma_{max}$ is debated with regard to the efficacy of an additive (peptide, peptoid, etc.) as a lung surfactant protein mimic, and no specific criteria exist for estimating the ideal value of $\gamma_{max}$, it has been established that $\gamma_{min}$ must reach <2 mN m$^{-1}$ in an lipid-additive film if the additive is to be considered an effective mimic.[18] In light of the high TL $\gamma_{max}$ of 60 mN m$^{-1}$ and the low TL+SP-B $\gamma_{max}$ of ~36 mN m$^{-1}$, it is concluded that a very surface-active mimic should exhibit a $\gamma_{max}$ of ≤45 mN m$^{-1}$ and a $\gamma_{min}$ of <2 mN m$^{-1}$. It should be noted that the former criterion is ~5 mN m$^{-1}$ below the $\gamma_{max}$ of all peptide- and peptoid-based positive controls. Relative closeness of γ values for different lipid-polymer films were largely determined by comparing the σ of the mean γ for the films. A difference in $\gamma_{max}$ of >3 mN m$^{-1}$ and a difference in $\gamma_{min}$ of ≥2 mN between films is generally considered to be significant.

Figure 4A:
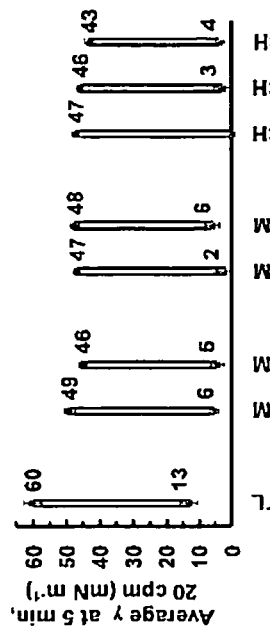
FIGS. 4A, 4B, 4C, and 4D are histograms depicting PBS data for lipid-polymer films in dynamic-bubble mode at 5 minutes at 37° C. Mean maximum ($65_{max}$, red circles) and minimum ($γ_{min}$, blue triangles) surface tensions (γ, mN m$^{-1}$) at 5 minutes of dynamic-bubble pulsation, 20 cycles per minute (cpm), are presented for all lipid films containing polymers or positive controls in an aqueous buffer (150 mM NaCl, 10 mM HEPES, 5 mM $CaCl_2$, pH 6.9) suspension at 37° C. The faint line at 45 mN m$^{-1}$ represents the defined activity threshold for a very surface-active mimic.
Figure 4B:
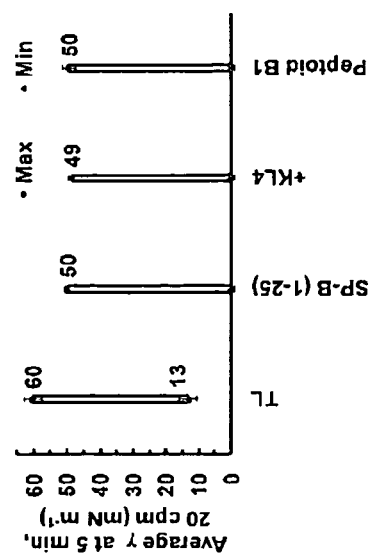
Figure 4C:
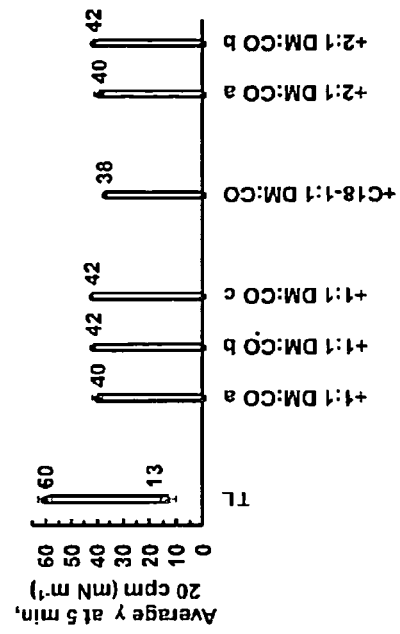
Figure 4D:
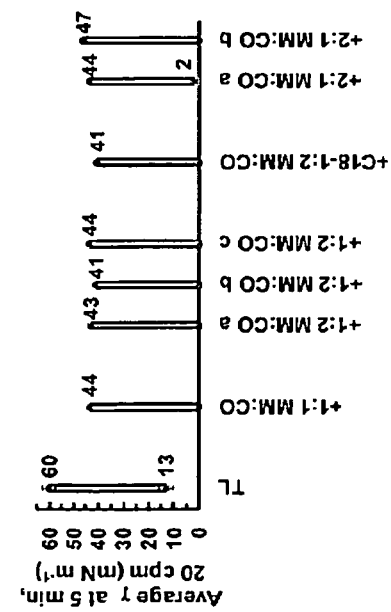

As in static-bubble mode, the addition of any mimic to the TL film in dynamic-bubble mode significantly reduced $\gamma_{max/min}$ values, demonstrating surfactant activity (see FIGS. 4A-4D). The TL film manifested poor surface activity, with a high $\gamma_{max}$~60 mN m$^{-1}$, a $\gamma_{min}$~13 mN m$^{-1}$, and ~43% SA compression to reach 20 mN m$^{-1}$ (FIG. 4A and FIG. 5). Among the films containing positive control compounds, addition of SP-B$_{1-25}$, KL$_4$, or Peptoid B1 to the film reduced $\gamma_{max}$ to ~50 mN m$^{-1}$ and $\gamma_{min}$ to near zero, with TL+KL$_4$ displaying the lowest percent SA compression of the positive controls, at 25%. Lipid films containing MM homopolymer, DM homopolymer, or MM:DM copolymers displayed slightly reduced $\gamma_{max}$ relative to the controls, but none of these purely cationic polymers was able to achieve $\gamma_{min}$<2 mN m$^{-1}$, and all displayed percent SA compressions in the range between films containing SP-B$_{1-25}$ and KL$_4$ (FIG. 4B and FIG. 5).

The inclusion of CH in nylon-3 copolymers slightly reduced the $\gamma_{max}$ relative to lipid-MM and lipid-DM films; the lowest $\gamma_{max}$ observed among these polymers was for TL+2:1 DM:CH at 43 mN m$^{-1}$, but the $\gamma_{min}$ only reached ~4 mN in$^{-1}$ in this case (FIG. 4). TL+1:2 MM:CH reached a near-zero $\gamma_{min}$, which was not achieved among lipid-polymer films containing purely cationic polymers. However, the CH-containing copolymers exhibited percent SA compressions in the realm of peptide-based controls (FIG. 5).

Lipid films containing nylon-3 copolymers with CO subunits displayed surfactant activity that was remarkably enhanced relative to all other copolymers, with significantly lower percent SA compression values, near-zero $\gamma_{min}$ in most cases, and consistently low $\gamma_{min}$ (44 mN m$^{-1}$ for TL+1:1 MM:CO and TL+2:1 MM:CO a, 43 mN m$^{-1}$ for TL+1:2 MM:CO a, and 40 mN m$^{-1}$ for TL+1:1 DM:CO a and TL+2:1 DM:CO a (FIGS. 4C and 4D and FIG. 5)). TL+2:1 MM:CO a did not quite reach $\gamma_{min}$=0 (1.77 mN m$^{-1}$±1.63 mN m$^{-1}$) and demonstrated a slightly higher percent compression (26%) than other CO-containing polymers (18-24%, FIG. 5). As in static-bubble mode, the dynamic activities of the nylon-3 copolymers were reproduced in subsequent batches (FIGS. 4A-4D and FIG. 5).

Inclusion of copolymers with an N-terminal octadecanoyl group, C18-1:1 DM:CO and C18-1:2 MM:CO, resulted in the greatest surface activity improvements to the lipid film. The TL+C18-1:2 MM:CO film reached $\gamma_{max}$~41 mN m$^{-1}$, which matched that of the most surface-active batch of TL+1:2 MM:CO (b), and the sample containing the octadecanoyl end group displayed a percent compression roughly ~2% lower (14% vs. 16% for TL+1:2 MM:CO b). TL+C18-1:1 DM:CO demonstrated the highest surface activity, with $\gamma_{max}$~38 mN m$^{-1}$ and a low ~12% SA compression.

In addition to low $\gamma_{max/min}$ and percent SA compression values, a loop shape during dynamic cycling that is qualitatively similar to natural LS or TL+SP-B is considered desirable and an indication of high surfactant activity. Although the significance of loop shape and hysteresis have yet to be clearly defined, it has been observed that Infasurf®[44] and the TL+SP-B[30] film exhibit 'knob-like' loop shapes that have a small extent of hysteresis and no dramatic changes in slope or shape upon expansion or compression. In contrast, the TL film had a significantly different but characteristic loop shape that resulted in a high percent SA compression to reach the $\gamma_{min}$ (FIG. 6A-6D).

Figure 6A:
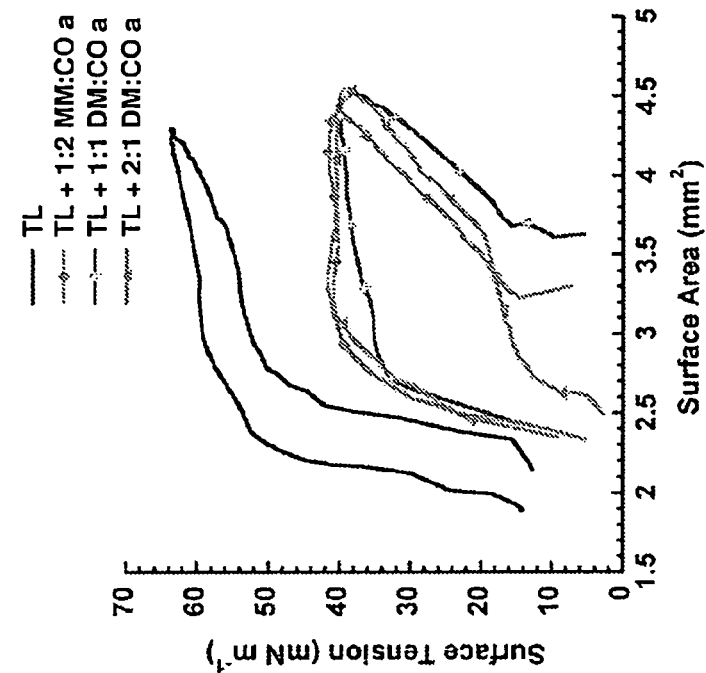
FIGS. 6A, 6B, 6C, and 6D are graphs depicting PBS bubble pulsation hysteresis loops for lipid-polymer films in dynamic-bubble mode at 5 Minutes at 37° C. Representative loops are shown for lipid-polymer films after 5 minutes of pulsation (20 cpm) in dynamic-bubble mode on the PBS in an aqueous buffer (150 mM NaCl, 10 mM HEPES, 5 mM CaCl$_2$, pH 6.9) suspension at 37° C. In dynamic cycling, bubble surface area expansion is clockwise from left to right, and vice-versa for compression. See Tables 4-6) for mean dynamic γ data±σ at selected time intervals at tabulated % Compression data±σ.
Figure 6B:
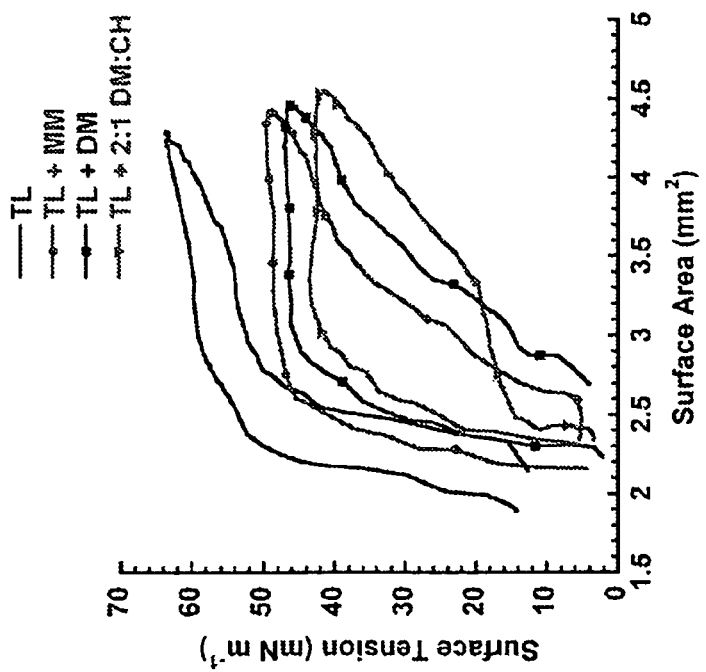
Figure 6C:
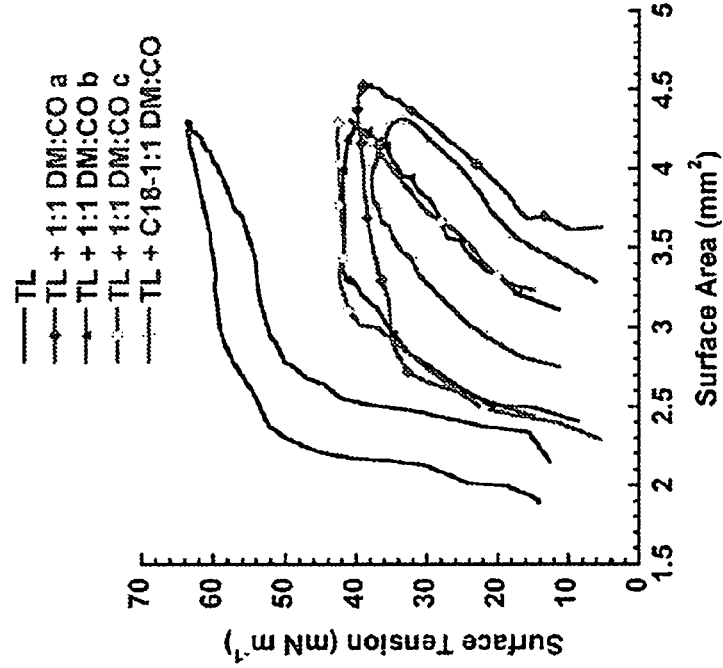
Figure 6D:
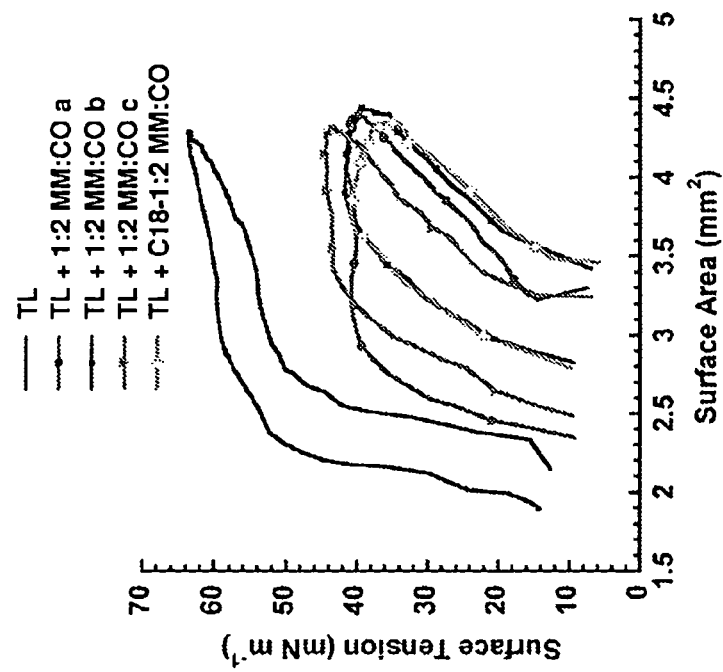

The loop shapes of TL+MM homopolymer or TL+DM homopolymer were very similar to one other, as can be seen in FIG. 6A; a similar loop shape was also observed for TL+SP-B$_{1-25}$, KL$_4$, and +Peptoid B1 (data not shown). TL+2:1 DM:CH also had a similar loop shape, but a distinctive feature was present upon compression, starting at 20 mN m$^{-1}$, wherein large changes in SA occurred with relatively small changes in $\gamma$. The loop features remained consistent for films containing MM:CO and DM:CO copolymers, aside from a lower $\gamma_{max}$, with the distinctive compression feature observed for TL+2:1 DM:1CO a (FIG. 6B).

The loop shapes remained fairly consistent among different batches of MM:CO and DM:CO copolymers, although there were some inter-batch variations in hysteresis (TL+2:1 DM:CO a vs. b; Figure S30). Small variations in hysteresis are not uncommon between lipid-only batches or films containing different batches of peptides or peptoids. Interestingly, in the case of TL+1:2 MM:CO b, TL+C18-1:2 MM:CO, and TL+C18-1:1 DM:CO, the loop shape closely resembled that seen for Infasurf®[44] and TL+SP-B films (FIG. 6A and FIG. 6B).[30] The 'knob-like' shape at expansion and low amount of hysteresis are very characteristic for Infasurf® and TL+SP-B films; the presence of these features in some TL+polymer films suggests that these materials may be very effective LS protein mimics.

Cytotoxicity Assay Against NIH 3T3 Fibroblasts. The biocompatibility of select nylon-3 copolymers was evaluated with NIH 3T3 fibroblasts using an MTS colorimetric assay. FIG. 7 shows that the 50% metabolic inhibitory dose (ID$_{50}$) of all tested copolymers compared favorably to that of the SP-B 1.25 peptide and Peptoid B1. Copolymers 1:2 MM:CO a, C18-1:2 MM:CO, and 1:1 DM:CO a were the least toxic materials, with ID$_{50}$ values more than five-fold higher than that of SP-B$_{1-25}$, and nearly 15-fold higher than that of Peptoid B1. Interestingly, an increased proportion of charged subunits correlated with increased cytotoxicity (2:1 MM:CO vs. 1:2 MM:CO, and 2:1 DM:CO vs. 1:1 DM:CO). Polymers bearing an N-terminal octadecanoyl group exhibited equal or greater cytoxicity relative to analogous polymers bearing an N-terminal p-(tert-butyl)benzoyl group. This trend may result from the increased hydrophobicity of the octadecanoyl group relative to the p-(tert-butyl)benzoyl group, which should lead to enhanced lipid binding for the former relative to the latter. The highest toxicities (lowest ID$_{50}$ values) were observed for copolymers with a high proportion of DM subunit, 2:1 DM:CH (12.0 µg mL$^{-1}$) and 2:1 DM:CO (9.0 µg mL$^{-1}$). Polymers with a comparable proportion of MM were not as toxic (2:1 MM:CO vs. 2:1 DM:CO). This trend may arise from the increased hydrophobicity of DM subunit relative to the MM subunit.

CHEMISTRY EXAMPLES

Example 1

Monomer and Co-Initiator Synthesis

Synthesis of Coinitiator (2):

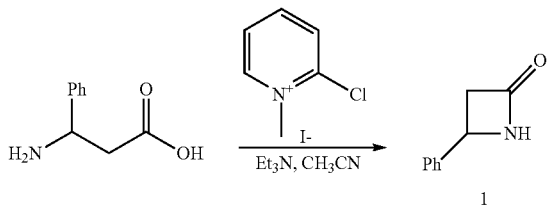

Compound 1 was prepared using the method of Huang and coworkers (Huang, H.; Iwasawa, N.; Mukaiyama, T. (1984) "A Convenient Method for the Construction of β-Lactam Compounds from β-Amino Acids Using 2-Chloro-1-Methyl Pyridinium Iodide as Condensing Reagent," Chem. Len. 1465-1466). In a 1 L round-bottomed flask was combined DL-3-amino-3-phenyl propionic acid (0.007 mol, 1.156 g), 2-chloro-1-methyl pyridinium iodide (1.1 eq., 0.0077 mol, 1.74 g), acetonitrile (700 mL) and triethylamine (2.2 eq., 0.0154 mol, 2.15 mL). The reaction was stirred under nitrogen and heated to reflux overnight. The solvent was removed by rotary evaporation and the crude product was purified by column chromatography in 1:1 hexanes: ethyl acetate. Yield: 0.808 g, 40%. $^1$H NMR (CDCl$_3$) δ 2.84-2.9, m, 1 H; 3.40-3.48, m, 1 H; 4.71-4.74, m, 1 H; 6.38, br s, 1 H; 7.2-7.4, m, 5 H.

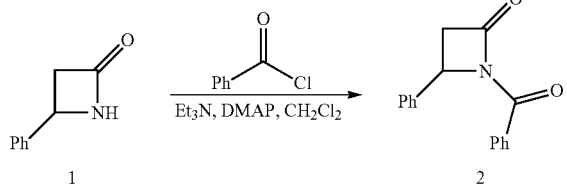

Compound 2 was prepared using the method of Park and coworkers (Park, H.; Hepperle, M.; Boge, T. C.; Himes, R. H.; Georg, G. I. (1996) "Preparation of Phenolic Paclitaxel Metabolites," J. Med. Chem. 39:2705-2709). In a 25 mL round-bottomed flask was combined (1) (0.0017 mol, 0.250 g), triethylamine (4.63 eq., 0.0073 mol, 1.02 mL), dry methylene chloride (6.3 tnL), and dimethylamino pyridine (10 mol %, 1.7 E-4 mol, 0.021 g). The reaction was cooled to 0° C. and benzoyl chloride (3.33 eq., 0.0057 mol, 0.66 mL) was added. The reaction was warmed to room temperature and stirred for 1 h. The reaction was quenched with saturated ammonium chloride (30 mL) and diluted with methylene chloride (150 mL). The reaction mixture was then washed with NaHCO$_3$ and then with brine. The organic portion was dried over MgSO$_4$ and the solvent removed by rotary evaporation. The crude product was purified by column chromatography in 1:1 hexanes: ethyl acetate. Yield: 0.320 g, 75%. $^1$H NMR (CDCl$_3$) δ 3.094, dd J=16.5, 3.9 Hz, 1 H; 3.528, dd J=16.5, 6.9 Hz, 1 H; 5.29, m, 1 H; 7.26-7.60, m, 8 H; 8.01-8.04, m, 2 H. $^{13}$C {$^1$H} NMR (CDCl$_3$) δ 44.23, 51.56, 125.77, 127.99, 128.26, 128.73, 129.75, 131.68, 133.22, 137.99, 163.91, 165.65. FTIR (ATR): 1675 cm$^{-1}$, 1735 cm$^{-1}$, 1778 cm$^{-1}$, 1795 cm$^{-1}$. MS-ESI: m/z =525.2 [2 M+Na]$^+$.

β-Lactam 3 was synthesized according to the literature precedent. See Parsons, P. J.; Camp, N. P.; Underwood, J. M.; Harvey, D. M. (1996) "Tandem Reactions of Anions: A Short and Efficient Route to±Anatoxin-a," *Tetrahedron*, 52:11637-11642.

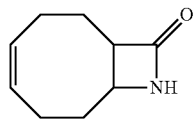
3

β-Lactams 4 and 5 were synthesized according to the literature precedent. See Dener, J. M.; Fantauzzi, P. P.; Kshirsagar, T. A.; Kelly, D. E.; Wolfe, A. B. (2001) "Large-Scale Synthesis of FMOC-Protected Non-Proteogenic Amino Acids: Useful Building Blocks for Combinatorial Libraries," *Organic Process Research and Development*, 5:445-449.

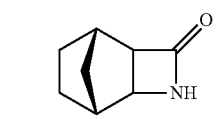
4

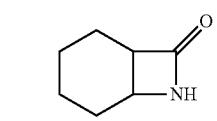
5

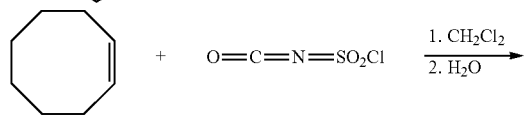

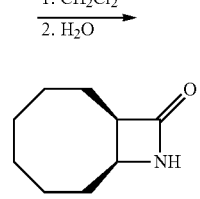
6

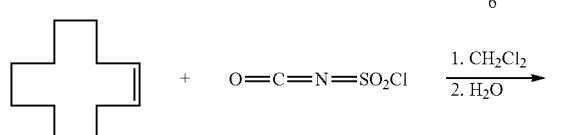

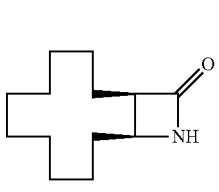
7

Compounds 6 and 7 were prepared using the same general method used for compounds 4 and 5.[4] For compound 6: In an oven-dried 25 mL round-bottomed flask was combined cis-cyclooctene (0.023 mol, 3 mL) and dry CH$_2$Cl$_2$ (3.3 mL). The reaction was cooled to 0° C. and stirred under N$_2$. A solution of chlorosulfonyl isocyanate (CSI) (1 eq., 0.023 mol, 2 mL) in dry CH$^2$C$_2$ (1.1 mL) was made and added dropwise to the cooled reaction mixture. The reaction was allowed to stir at 0° C. for 1 h and then warned to room temperature overnight. The reaction was then re-cooled to 0° C. and quenched by adding water. The quenched reaction mixture was added to a suspension of Na$_2$SO$_3$ (1.45 g) in water (4.3 mL), keeping the temperature below 25° C. and the pH between 5 and 7 using 2 M NaOH. The reaction was allowed to warm to room temperature overnight. The layers were separated and the aqueous portion was extracted with EtOAc. The combined organic portions were dried over MgSO$_4$ and the solvent removed by rotary evaporation. The crude product can be purified by column chromatography (EtOAc as eluent) or recrystallization from CH$_2$Cl$_2$ and hexanes. Yield=3.6 g, 51%. $^1$H NMR (CDCl$_3$) δ 1.30-1.99, m, 12 H; 3.01-3.10, m, 1 H; 3.62-3.69, m, 1 H; 5.86, br s, 1 H. $^{13}$C {$^1$H} NMR (CDCl$_3$) δ 21.34, 25.25, 25.69, 27.24, 28.59, 27.72, 53.58, 171.0. FTIR (ATR): 1725 cm$^{-1}$, 3205 cm$^{-1}$. MS-EI: m/z=154.1 [M+H]$^+$.

For Compound 7: In an oven-dried round-bottomed flask was combined cyclododecene (0.023 mol, 3.97 mL) and CSI (1 eq., 0.023 mol, 2 mL). The reaction was put under nitrogen and heated to 50° C. overnight. The reaction was allowed to cool, diluted with CH$_2$Cl$_2$, and quenched by adding water. The quenched reaction was added to a suspension of Na$_2$SO$_3$ (1.6 g) in water (5 mL), keeping the temperature below 25° C. and the pH between 5 and 7 using 2 M NaOH. The reaction was allowed to warm to room temperature overnight and then the layers were separated. The aqueous layer was extracted twice with EtOAc and the combined organic layers were dried over MgSO$_4$ and the solvent was removed by rotary evaporation. The crude product was purified by recrystallization from CH$_2$Cl$_2$ and hexanes. Yield=0.47 g, 10%. $^1$H NMR (CDCl$_3$) δ 1.30-1.80, m, 20 H; 3.10-3.16, m, 1 H; 3.64-3.70, m, 1 H; 6.11, br s, 1 H. $^{13}$C {$^1$H} NMR (CDCl$_3$) δ 2.24, 22.84, 23.22, 24.90, 27.62, 27.83, 28.12, 28.21, 29.20, 53.20, 54.20, 171.78. FTIR (ATR): 1740 cm$^{-1}$, 3204 cm$^{-1}$. MS-ESI: m/z=232.3 [M+Na]$^+$.

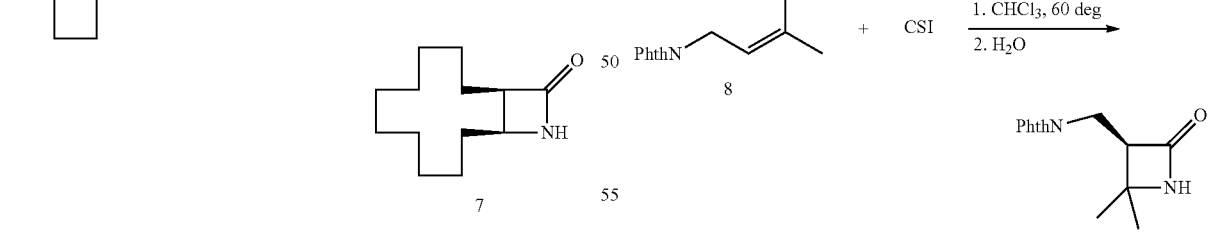

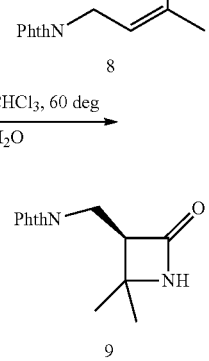
9

For Compound 8: In a 500 mL round-bottomed flask was combined potassium phthalimide (1.5 eq., 0.067 mol, 12.33 g) and DMF (140 mL). The reaction was stirred and a solution of 1-chloro-3-methyl-2-butene (1 eq., 0.044 mol, 5 mL) in DMF (95 mL) was added to the reaction. The flask was put under N$_2$ and heated to 60° C. overnight. The reaction was allowed to cool and then poured into 1400 mL ice and water with vigorous stirring. The stirring was continued until the ice melted. The resulting white precipitate was isolated by filtration. The wet solid was dissolved in CH$_2$Cl$_2$ and the layers were separated. The organic portion was dried over MgSO$_4$ and the solvent removed by rotary evaporation to give crude product. The product was purified by recrystallization from CH$_2$Cl$_2$ and hexanes. Yield=7.2 g, 76%.

Compound 9 was prepared from Compound 8 in the following manner. In a 100 mL round-bottomed flask was placed Compound 8 (1 eq., 0.033 mol, 7 g). It was dissolved in as little dry CH$_2$Cl$_2$ as possible and the flask put under N$_2$ and cooled to 0° C. CSI (1 eq., 0.033 mol, 2.9 mL) was added to the flask and the reaction allowed to stir and warm to room temperature for 1-2 days. The reaction was quenched by adding water and the quenched reaction mixture was added to a suspension of Na$_2$SO$_3$ and Na$_2$HPO$_4$ (5 g each) in water (140 mL). The pH was maintained between 5 and 7 using 2 M NaOH and the reaction was allowed to stir at room temperature for 2 days. The layers were then separated and the aqueous portion was extracted twice with CH$_2$Cl$_2$. The combined organic portions were dried over MgSO$_4$ and the solvent removed by rotary evaporation. The crude product was recrystallized from CH$_2$Cl$_2$ and hexanes. Yield=6.2 g, 73%. $^1$H NMR (CDCl$_3$) δ 1.45, s 3 H; 1.47, s, 3 H; 3.41, td J=8.1, 0.9 Hz, 1 H; 3.91, dd J=14.1, 8.1 Hz, 1 H; 4.05-4.13, m, 1 H; 6.44 br s, 1 H; 7.71-7.74, m, 2 H; 7.84-7.87, m, 2 H. $^{13}$C {$^1$H} NMR (CDCl$_3$) δ 14.31, 21.15, 23.38, 25.58, 34.31, 55.18, 56.66, 60.48, 123.52, 132.11, 134.17, 167.47, 168.06. FTIR (ATR): 1715 cm$^{-1}$, 1741 cm$^{-1}$, 3200 cm$^{-1}$. MS-ESI: m/z=259.3 [M+H]$^+$.

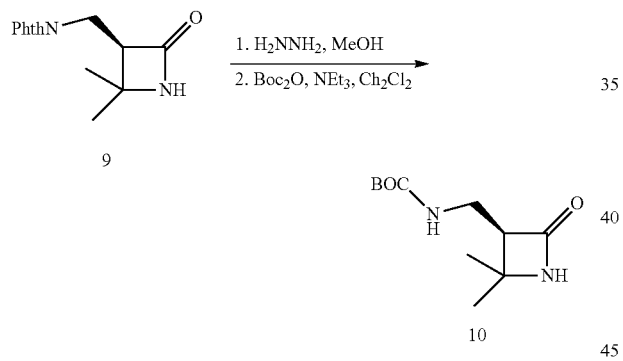

9

10

Compound 10 was prepared from Compound 9 in the following manner: In a 250 mL round-bottomed flask was suspended Compound 9 (1eq., 0.024 mol, 6.2 g) in methanol (36 mL). Hydrazine (3 eq., 0.072 mol, 2.26 mL) was added and the reaction was allowed to stir at room temperature under N$_2$ overnight. The methanol was removed by rotary evaporation and the resulting solid was triturated with chloroform. The solvent was removed from the chloroform washings by rotary evaporation. The residue was placed in a 500 mL round-bottomed flask with CH$_2$Cl$_2$ (200 mL). Triethylamine (1.1 eq., 0.053 mol, 7.39 mL) was then added followed by a solution of di-cert-butyl-dicarbonate (BOC$_2$O) (1.1 eq., 0.053 mol, 11.6 g) in CH$_2$Cl$_2$ (100 mL). The reaction was allowed to stir at room temperature overnight and then washed twice with 2 M HCl, twice with 2 M NaOH, and once with brine before being dried over MgSO$_4$ and stripped by rotary evaporation to yield crude product. The product was purified by column chromatography using EtOAc as eluent. Yield=2.9 g, 53%. $^1$H NMR (CDCl$_3$) δ 1.40, s, 3 H; 1.44, s, 3 H; 1.45, s, 9 1-1; 2.97 app t J=7.8 Hz, 1 H; 3.29, m, 1 H; 3.58, m, 1 H; 5.10, br s, 1 H. $^{13}$C {$^1$H} NMR (CDCl$_3$) δ 22.92, 28.49, 28.68, 37.20, 54.83, 58.34, 79.61, 155.89, 169.32. FTIR (ATR): 1688 cm$^{-1}$, 1716 cm$^{-1}$, 1744 cm$^{-1}$, 3194 cm$^{-1}$, 3280 cm$^{-1}$. MS-ESI/EMM: m/z=Calc. 251.1372 [M+Na]$^+$. Meas. 251.1372 [M+Na]$^+$.

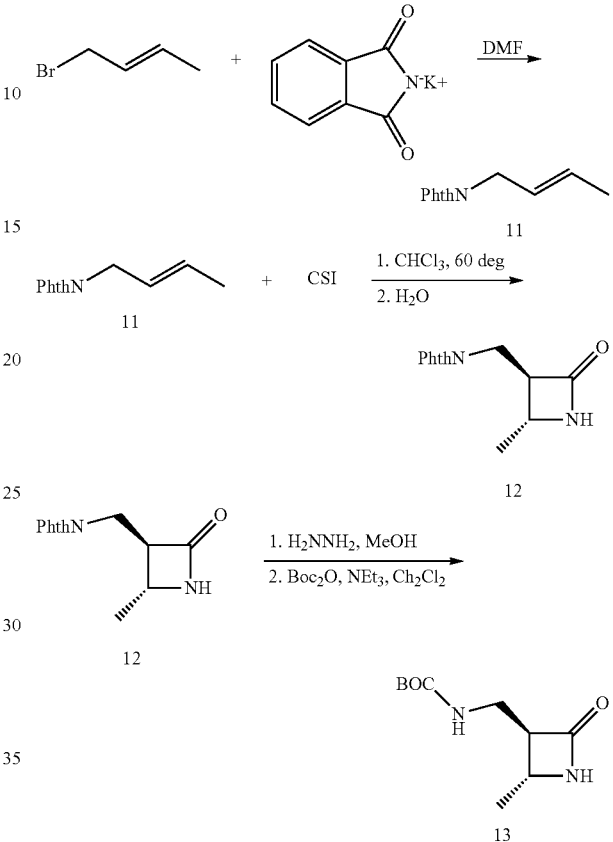

Compound 11: In a 2 L round-bottomed flask was combined potassium phthalimide (1.5 eq., 0.28 mol, 52 g) and DMF (400 mL). A solution of crotyl bromide (1 eq., 0.185 mol, 25 g) in DMF (300 mL) was then added and the reaction stirred at 60° C. overnight. The reaction was allowed to cool and then poured into 4000 mL ice and water with vigorous stirring. The stirring was continued until the ice melted. The resulting white precipitate was isolated by filtration. The wet solid was dissolved in CH$_2$Cl$_2$ and the layers were separated. The organic portion was dried over MgSO$_4$ and the solvent removed by rotary evaporation to give crude product. The product was purified by recrystallization from CH$_2$Cl$_2$ and hexanes. Yield =17.8 g, 56%.

Compound 12: In a 100 mL round-bottomed flask was placed Compound 11 (1 eq., 0.085 mol, 17 g). It was dissolved in as little dry CHCl$_3$ as possible and the flask put under N$_2$ and cooled to 0° C. CSI (1 eq., 0.033 mol, 2.9 mL) was added to the flask and the reaction allowed to stir and warm to room temperature, then heated to 60° C. for 4-5 days. The reaction was quenched by adding water and the quenched reaction mixture was added to a suspension of Na$_2$SO$_3$ and Na$_2$HPO$_4$ (40 g each) in water (700 mL). The pH was maintained between 5 and 7 using 2 M NaOH and the reaction was allowed to stir at room temperature for 2 days. The layers were then separated and the aqueous portion was extracted twice with CH$_2$Cl$_2$. The combined organic portions were dried over MgSO., and the solvent removed by rotary evaporation. The crude product was recrystallized from $CH_2Cl_2$ and hexanes. Yield=7.6 g, 38%. $^1$H NMR ($CDCl_3$) δ 1.32, d J=6 Hz, 3 H; 3.15 app t J=6.9 Hz, 1 H; 3.79-3.83, m, 1 H; 3.97, dd J=14, 9.6 Hz, 1 H; 4.14, dd J=14, 5.7 Hz, 1 H; 6.01, br s, 1 H; 7.72-7.77, m, 2 H; 7.84-7.88, m, 2 H. $^{13}$C {$^1$H} NMR ($CDCl_3$) δ 20.75, 36.62, 50.46, 57.12, 123.69, 132.11, 134.37, 167.07, 168.23. MS-ESI: m/z=267.2 [M+Na]$^+$.

Compound 13: In a 25 mL round-bottomed flask was suspended Compound 12 (1 eq., 0.0021 mol. 0.5 g) in methanol (10 mL). Hydrazine (5 eq., 0.0105 mol. 0.33 mL) was added and the reaction was allowed to stir at room temperature under $N_2$ overnight. The reaction was filtered on a frit and washed with copious amounts of methanol. The solvent was removed from the filtrate by rotary evaporation. The residue was placed in a 100 mL round-bottomed flask with $CH_2Cl_2$ (20 mL). Triethylamine (1.1 eq., 0.0057 mol, 0.8 mL) was then added followed by a solution of di-tert-butyl-dicarbonate ($BOC_2O$) (1.1 eq., 0.0057 mol, 1.25 g) in $CH_2Cl_2$ (10 mL). The reaction was allowed to stir at room temperature overnight and then washed twice with 2 M HCl, twice with 2 M NaOH, and once by brine before being dried over $MgSO_4$ and stripped by rotary evaporation to yield crude product. The product was purified by column chromatography using EtOAc as eluent. Yield =0.071 g, 16%. $^1$H NMR ($CDCl_3$) δ 1.37, d J=6 Hz, 3 H; 1.44, s, 9 H; 2.89, tdd J=6, 2.1, 0.9 Hz, 1 H; 3.48, m, 2 H; 3.64, qd J=6, 2.1 Hz, 1 H; 4.95, br s, 1 H; 6.06, br s, 1 H. $^{13}$C NMR ($CDCl_3$) δ20.54, 28.55, 38.46, 48.84, 58.57, 79.89, 164.71, 168.99. MS-ESI/EMM: m/z =Calc. 237.1215 [M+Na]$^+$. Meas. 237.1208 [M+Na]$^+$.

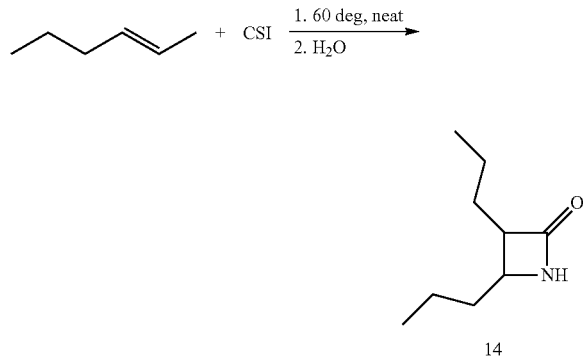

Compound 14: In a dry 25 mL round-bottomed flask was placed trans-4-octene (1 eq., 0.009 mol, 1.4 mL). CSI (1 eq., 0.009 mol, 0.78 mL) was added to the flask and the reaction allowed to stir at 60° C. overnight. The reaction was diluted with $CH_2Cl_2$ and then quenched by adding water. The quenched reaction mixture was added to a suspension of $Na_2SO_3$ and $Na_2HPO_4$ (1 g each) in water (20 mL). The pH was maintained between 5 and 7 using 2 M NaOH and the reaction was allowed to stir at room temperature overnight. The layers were then separated and the aqueous portion was extracted twice with $CH_2Cl_2$. The combined organic portions were dried over $MgSO_4$ and the solvent removed by rotary evaporation. The crude product was purified by column chromatography using 1:1 hexanes:EtOAc as eluent. Yield=0.38 g, 27%. $^1$H NMR ($CDCl_3$) δ 0.98, m, 6 H; 1.31-1.77, m, 8 H; 2.73, br t J=7.5 Hz, 1 H; 3.29, td J=6.9, 2.1 Hz, 1 H; 6.48, br s, 1 H. $^{13}$C NMR ($CDCl_3$) δ 14.11, 14.16, 19.90, 20.78, 30.89, 37.47, 55.38, 56.91, 171.83. MS-EI: m/z=156.2 [M+H]$^+$.

Synthesis of Compound (15):

Compound 15 was prepared using a modified literature procedure. See Parsons, P. J.; Camp, N. P.; Underwood, J. M.; Harvey, D. M. (1996) "Tandem Reactions of Anions: A Short and Efficient Route to ±Anatoxin-a." *Tetrahedron* 52: 11637-11642. In a 50 mL round-bottomed flask was combined 4-tert-butylstyrene (0.016 mol, 2.62 g) and dry diethyl ether (5 mL). The mixture was cooled to 0° C. and stirred under $N_2$. Chlorosulfonyl isocyanate (CSI) (1 eq., 0.016 mol, 2.32 g) was added dropwise to the cooled reaction mixture. The reaction was allowed to stir at 0° C. for 1 h and then warmed to room temperature overnight. The reaction was then diluted with chloroform (20 mL), cooled to 0° C. and quenched by addition into a stirring aqueous solution (100 mL) of $Na_2SO_3$ (12 g) and $Na_2PO_4$ (14 g), keeping the temperature below 25° C. and the pH between 6 and 8 by additions of 2 M NaOH. The reaction was allowed to warm to room temperature overnight. The layers were separated and the aqueous portion was extracted with chloroform. The combined organic portions were dried over $MgSO_4$ and the solvent removed by rotary evaporation. The crude product was recrystallized from diethyl ether. Yield: 1.8 g, 54%. $^1$H NMR (300 MHz, $CDCl_3$, ppm) δ 1.32, s, 9 H; 2.90, ddd J=15, 2.5, 1.1 Hz, 1 H; 3.43, ddd J=15, 5.1, 2.4 Hz, 1 H; 4.70, dd J=5.4, 2.7 Hz, 1 H; 6.1, s, 1 H; 7.37, app. dd J=33, 10.8 Hz, 4 H. MS (ESI)=429.5 [2M+Na]$^+$ Example 2

Polymer Synthesis

Materials:

All reagents were obtained from Aldrich (Milwaukee, Wis.) and used as received. $CH_2Cl_2$ and THF were distilled under reduced pressure over $CaH_2$.

Instrumentation:

$^1$H (300 MHz) and $^{13}$C (75 MHz) NMR spectra were obtained on a Bruker AC+ 300 NMR spectrometer. Gel Permeation Chromatography (GPC) was performed using a Shimadzu LC-10AD liquid chromatography (HPLC) pump equipped with Wyatt miniDawn and Optilab rex detectors. The mobile phase was THF with a flow rate of 1 mL/min. Separations were performed using TSK-GEL column set (2× $GMH_{HR}$-H).

Homopolymerization of 6:

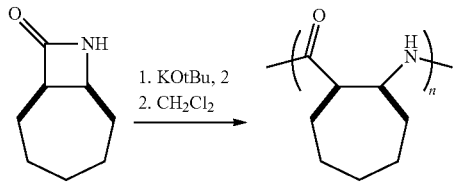

Polymerization of 6 is a representative procedure for the polymerizations of β-lactam monomers 3-7, 10, and 13-15. Any experimental and observational exceptions will be noted. In a 7 mL glass vial, under inert atmosphere, was combined 6 (1 mmol, 153 mg), potassium tert-butoxide (KOtBu, 0.045 mmol, 5 mg) as base to deprotonate a certain fraction of the monomer, and 2 (0.02 mmol, 5 mg) as coinitiator and as the means to control the molecular weight. Monomer to coinitiator ratios ranging from 1/10 to 1/250 were successfully employed depending on the targeted molecular weight. The mixture was dissolved by addition of dichloromethane ($CH_2Cl_2$, 1 mL), or THF (1 mL) and kept under room temperature for 0.5 to 4 hours depending on the monomer to coinitiator ratio where higher ratios require longer polymerization times. Then the mixture was opened to air, the polymer was precipitated into pentane (10 mL), and isolated by centrifuging and removing the supernatant. Polymer was dried overnight under reduced pressure at room temperature. The isolated yield was 95% (146 mg). $^1$H NMR (300 MHz, $CDCl_3$, ppm) δ 1.10-2.10, broad s. 12 H; 2.15-3.10, broad m, 1 H; 4.2-5.0, broad m, 1 H; 7.43, m, end-group low-resolution peak; 7.89, m, end-group low-resolution peak. $M_n$=5840 g/mol, polydispersity index (PDI)=1.02 (dn/dc=1.37).

Alternative Compounds as Base Initiator:

The general procedure described in the above paragraph was employed by replacing KOtBu with an alternative base including lithium bis(trimethylsilyl)amide ($LiN(TMS)_2$), potassium bis(trimethylsilyl)amide ($KN(TMS)_2$), sodium methoxide (NaOEt, in tetrahydrofuran). All of the above mentioned bases resulted in low PDI polymers with molecular weights in close approximation to targeted molecular weights.

Less Preferred Initiators:

The following metal complexes $Sc(N(TMS)_2)_3$, $Al_2(N(Me)_2)_6$, $Al(N(TMS)_2)_3$, $Zn(N(TMS)_2)_2$, $Sn(N(TMS)_2)_2$, and $CpTi(N(Me)_2)_2Cl$ were employed in the above described general polymerization procedure and initial results showed the reactions resulted in the recovery of more than 90 mol % of the monomers. Little polymeric product was obtained. Thus, these metal complexes are not preferred for use in the present invention.

Alternative Homopolymerization of 6:

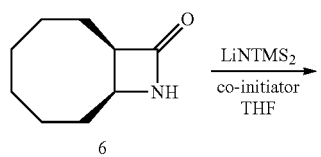

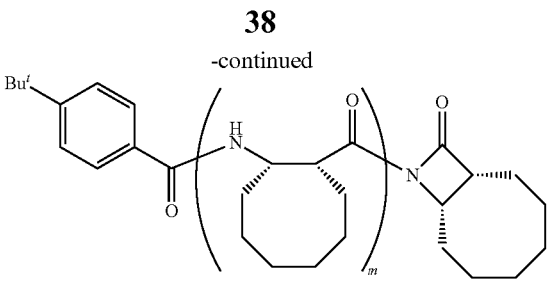

Here, the reaction takes place in THF at ambient temperature in the presence of a base [$LiN(SiMe_3)_2$] and a co-initiator (as shown either 4-tert-butyl benzoyl chloride (TBBC) or compound 2). The appropriate amounts of the monomer and co-initiator were mixed together in THF, whereupon a solution of base was added to the mixture in one portion. After 1 hour, the polymer product was precipitated by adding pentane to the reaction solution. The product was isolated by centrifugation and dried under high vacuum. 4-Tert-butyl benzoyl chloride or the N-benzoyl-β-lactam (compound 2) were used as co-initiators.

Reactions using 4-tert-butyl benzoyl chloride as the co-initiator showed narrower polydispersity of the polymer product obtained as compared to reactions using compound 2 as the co-initiator. Other bases (KOtBu, KH, NaOMe, NaOH) and alternative solvents and solvent mixtures ($CH_2Cl_2$, MeOH, $THF/H_2O$) were also tried for this reaction. Polymerization readily occurred in $CH_2Cl_2$, but the resulting polymer had slightly broader polydispersity. Similar increased broadening of the polydispersity was observed when KOtBu and NaOMe(THF) were used as the base. The use of heterogeneous KH as a base yielded a polymer with PDI>2. Adding water or amine (20 mol %) to the reaction yields a polymer product with a relatively small molecular weight, but without any broadening of the PDI of the product (<2). Both water and amine are known to poison other anionic polymerization reactions. Polydispersity broadened (from about 1.06 to 1.27) when the polymerization reaction is allowed to proceed for several hours.

A host of monomer, co-initiator, solvent, and base combinations were fabricated in the same fashion as reported here. The results are summarized in Table 7.

TABLE 7

Polymerization results for monomers 1-5 ([monomer]/[co-initiator] = 30):

| Monomer | Co-initiator | Base | Solvent | Yield, % | $M_n$ | PDI |
|---|---|---|---|---|---|---|
| 6 | TBBC | LiN(SiMe$_3$)$_2$ | THF | 96 | 4,900 | 1.05 |
| 6 | Cmpd 2 | LiN(SiMe$_3$)$_2$ | THF | 95 | 4,700 | 1.12 |
| 6 | TBBC | LiN(SiMe$_3$)$_2$ | CH$_2$Cl$_2$ | 93 | 5,100 | 1.14 |
| 6 | TBBC | KOtBu | THF | 96 | 5,400 | 1.11 |
| 6 | Cmpd 2 | KOtBu | CH$_2$Cl$_2$ | 95 | 4,900 | 1.15 |
| 6 | TBBC | KH | THF | 94 | 6,800 | 2.40 |
| 6 | TBBC | MeONa | THF | 97 | 5,100 | 1.14 |
| 6 | TBBC | MeONa | MeOH | No reaction | | |
| 6 | Cmpd 2 | NaOH | THF/H$_2$O (1:1) | No reaction | | |
| 6 | Cmpd 2 | LiN(SiMe$_3$)$_2$ | THF/BnNH$_2$ (20% mol to monomer) | 92 | 5,200 | 1.12 |
| 6 | Cmpd 2 | LiN(SiMe$_3$)$_2$ | THF/H$_2$O (20% mol to monomer) | 90 | 4,950 | 1.14 |
| 6 | Cmpd 2 | LiN(SiMe$_3$)$_2$ | THF/H$_2$O (1:20) | 93 | 4,500 | 1.16 |
| 5 | TBBC | LiN(SiMe$_3$)$_2$ | THF | 97 | Insoluble in THF | |
| 7 | TBBC | LiN(SiMe$_3$)$_2$ | THF | 95 | 7,300 | 1.10 |
| 10 | TBBC | LiN(SiMe$_3$)$_2$ | THF | 98 | 5,200 | 1.06 |
| 13 | TBBC | LiN(SiMe$_3$)$_2$ | THF | 98 | 5,900 | 1.10 |

This Example demonstrates a general approach for preparing β-polypeptides bearing side chains having polar functional groups.

Homopolymerization of Other β-Lactam-Containing Monomers:

Using the approach recited in the immediately prior Example, the following bicyclic and monocyclic monomers were also successfully polymerized:

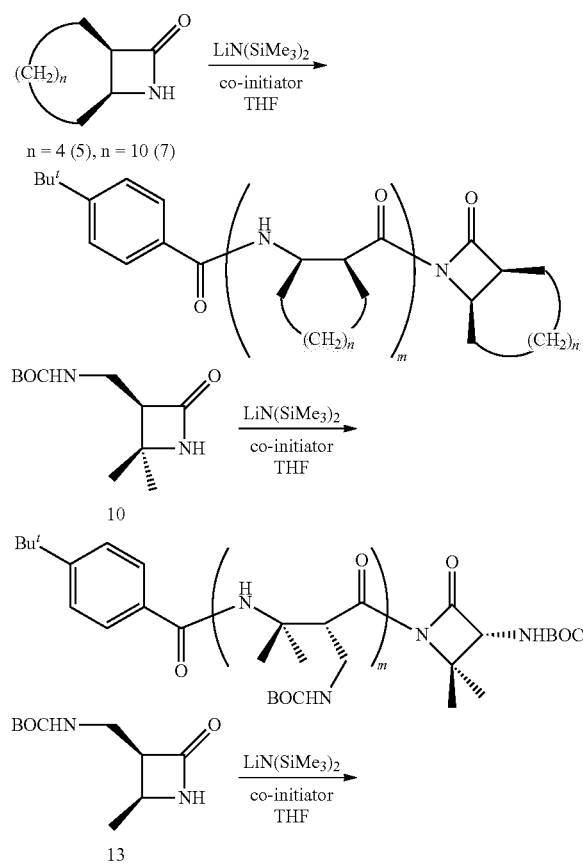

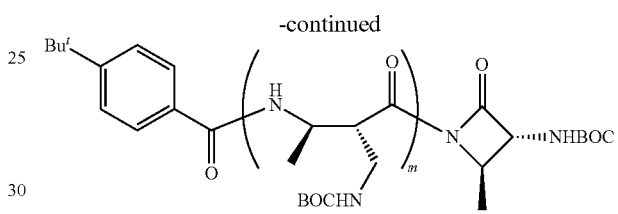

Homopolymerization of 3:

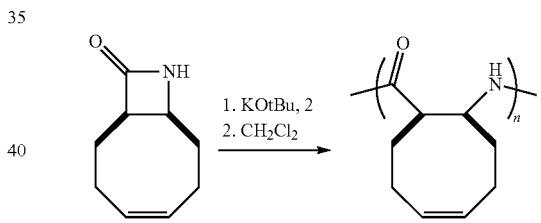

In a 7 mL glaSs vial, under inert atmosphere, was combined 3 (0.2 mmol, 30 mg), potassium cert-butoxide (KOtBu, 0.0045 mmol, 0.5 mg), and 2 (0.002 mmol, 0.5 mg). The polymer was isolated as described above for poly(6). The isolated yield was 92% (142 mg). $^1$H NMR (300 MHz, CDCl$_3$, ppm) δ 1.30-3.20, broad m, 9 H; 4.20-4.80, broad s, 1 H; 5.40-5.80, broad s, 2 H; 7.43, m, end-group low-resolution peak; 7.89, m, end-group low-resolution peak. $M_n$=16,000 g/mol, PDI=1.2 (for dn/dc=1.37). The GPC curve for this polymer is shown in FIG. 1.

Homopolymerization of 5:

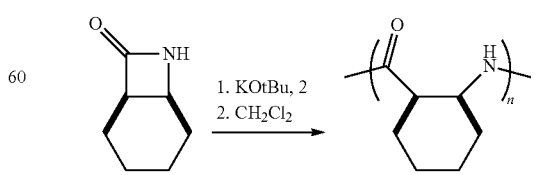

The isolated yield was 90% (139 mg). $^1$H NMR (300 MHz, CDCl$_3$, ppm) δ 1.10-2.05, broad m, 8 H; 2.53, s, 1 H; 3.98, s, 1 H; 7.43, m, end-group low-resolution peak; 7.89, m, end-group low-resolution peak. The resulting polymer was mostly insoluble in THF.

Homopolymerization of 10:

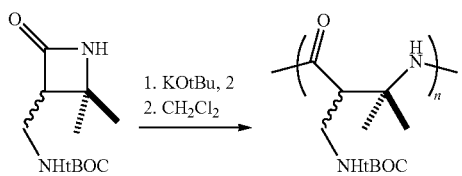

In a 7 mL glass vial, under inert atmosphere, was combined 10 (0.2 mmol, 45 mg), potassium tert-butoxide (KOtBu, 0.02 mmol, 2 mg), and 2 (0.014 mmol, 3.5 mg). The polymer was isolated as described above for poly(6). The isolated yield was 95% (44 mg). $^1$H NMR (300 MHz, CDCl$_3$, ppm) δ 1.00-1.80, broad s, 9 H; 2.05-3.70, overlapping resonances, broad m, 9 H; 7.50, m, end-group low-resolution peak; 7.94, m, end-group low-resolution peak. $M_n$=10,400 g/mol, PDI=1.16 (for dn/dc=1.37). The t-BOC protected primary amine groups on this polymer were deprotected by dissolution of the polymer in trifluoroacetic acid (100 mg/mL) and treating at 55° C. for 8 hours, resulting in a water soluble polymer. $^1$H NMR (300 MHz, D$_2$O, ppm) δ 1.10-1.70, m, 6 H; 2.9-3.6, broad overlapping peak, 3.19, s, 1 H; 3.40, s, 1 H; 7.42-7-71, m, end-group low-resolution peak.

Homopolymerization of 13:

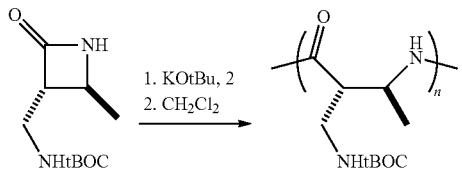

In a 7 mL glass vial, under inert atmosphere, was combined 10 (0.14 mmol, 30 mg), potassium tert-butoxide (KOtBu, 0.01 mmol, 1 mg), and 2 (0.004 mmol, 1 mg). The polymer was isolated as described above for poly(6). The isolated yield was 91% (27 mg). $^1$H NMR (300 MHz, CDCl$_3$, ppm) δ 1.18, broad s, 3 H; 1.43, broad s, 9 H; 2.2, s, 1H, 2.4-4.4, set of overlapped resonances, 4 H; 7.50, m, end-group low-resolution peak; 7.94, m, end-group low-resolution peak. Deprotected water soluble poly(13) was obtained as described for poly(10). NMR (300 MHz, D$_2$O, ppm) δ 1.11, s, 3 H; 2.9, in, 2 H; 3.22, s, 1 H; 4.17, s, 1 H; 7.35-7-62, m, end-goup low-resolution peak.

Homopolymerization of 14:

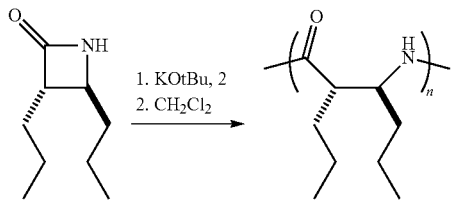

When the general polymerization procedure is applied to 14, the polymerization mixture solidifies within 5 minutes. Polymer is extensively washed with ether resulting in a white powder, insoluble in chloroform, THF, and DMSO.

Homopolymerization of 15:

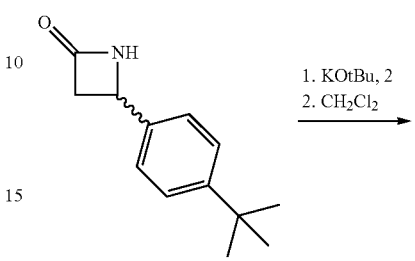

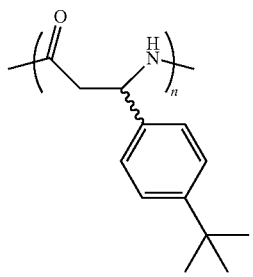

When the general polymerization procedure is applied to 14, the polymerization mixture stays homogeneous. However when polymer is precipitated in pentane the resulting white powder is insoluble in chloroform, THF, and DMSO.

Example 3

Living Polymerization (a) Molecular Weight of the Product Polymer as a Function of the Ratio of Monomer-to-Co-Initiator Ratio ([Monomer]/[Co-Initiator]):

A study was conducted to determine if systematically adjusting the ratio of the concentration of monomer reactants to the concentration of the co-initiator ([monomer]/[co-initiator]) would have a corresponding effect on the molecular weight of the resulting polymer product. Compound 6 was used as the monomer for this Example. The results (not shown) show that the molecular weight of the polymers obtained versus the [monomer]/[co-initiator] ratio exhibits a linear, proportional dependence up to about [monomer]/[co-initiator]=80. These results reflect and confirm the living character of the polymerization reaction.

(b) Degenerate Block Co-Polymerization:

The living character of polymerization was also confirmed by carrying out degenerate block-copolymerization of monomer 6 as shown in Reaction Scheme 6:

Reaction Scheme 6

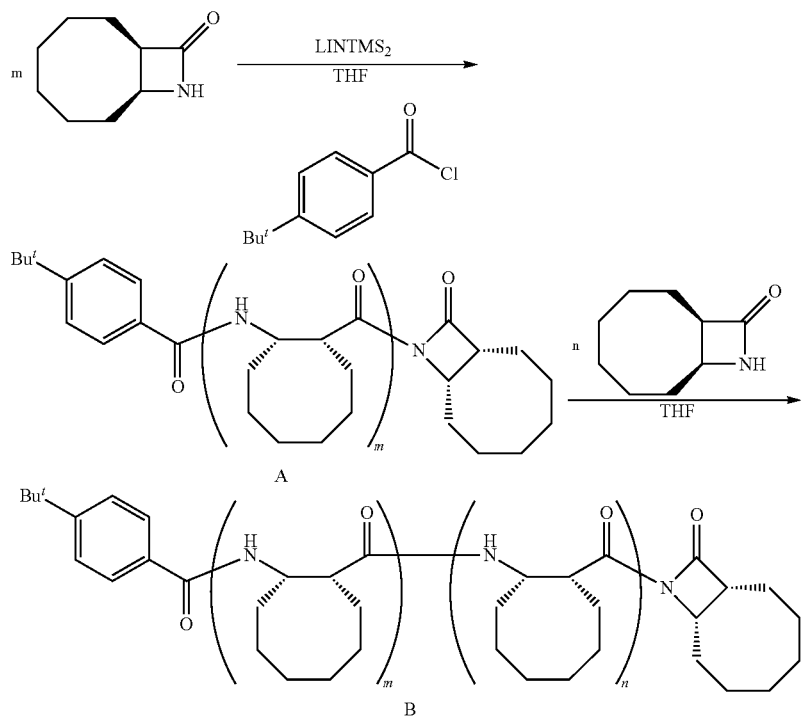

The GPC curves, shown in FIGS. 4 and 5, show the complete consumption of the initial polymer product A (FIG. 4) and the appearance of a degenerate monomodal block-copolymer product B (FIG. 5). Polymerization of compound 6 with MeONa and compound 5 with $LiN(SiMe_3)2$ were also confirmed to proceed in living fashion. This is significant because it allows for exquisite control of the product using homopolymerization or copolymerization.

Example 4

Random Copolymerizations

The general polymerization procedure was applied to mixtures of monomers resulting in polymers without any broadening in molecular weight distributions. $^1$H NMR analysis showed the presence of all resonances from individual homopolymers overlapped.

Example 5

Block Copolymerizations

Block copolymers were prepared by sequential comonomer addition. First a desired homopolymer was prepared according to the general polymerization procedures recited above, and after allowing time for the completion of first block (20 to 120 minutes depending on monomer to initiator ratios) a second monomer was added and second block was formed. Alternatively a homopolymer can be isolated by precipitation, redissolved in a polymerization mixture according to the general polymerization procedure as a replacement for coinitiator 2, and lead to growth of a second block from the chain-end of the first block. Comparisons of molecular weights of first block and diblock showed the expected increase in molecular weight without a significant broadening in molecular weight distributions. In particular, see FIG. 2, which shows two superimposed GPC curves for a homopolymer and a diblock co-polymer fabricated using the homopolymer. The earlier eluting peak in FIG. 2 is the diblock copolymer. and the later eluting peak is the homopolymer.

Example 6

Terminal Functionalization

Because the polymerization proceeds in a living fashion, the termini of the polymer chains can be functionalized using appropriate co-initiators that also function as a terminal co-monomer reactant. Co-monomers for terminal functionalization can include broad classes of functional groups. including hydrophobic, anionic. cationic and neutral hydrophilic groups, without limitation. An attractive feature of the polymerization method is the ability to control the functional groups located at either end of the polymer. The acylating agent used as the co-initiator (in combination with a strong base) functionalizes one end of the polymer chain and the other end of the chain possesses an imide group that will react with suitable nucleophiles (e.g., primary amines) after the polymerization reaction is complete. By exploiting the fundamental characteristics of the inventive polymerization technique, one can introduce a wide range of functional groups into the polymer, both along the main chain (via side chains incorporated into the monomers) and at each end of the polymer (by choosing an appropriate co-initiator and reaction the terminal imide group after polymerization is complete). These functional groups are expected to play a significant role in the biological activity of the material.

In this Example, 4-chloromethyl benzoyl chloride (C) was used as a co-initiator to yield a polymer having a 4-chloromethyl benzoyl terminus. See Reaction Scheme 7:
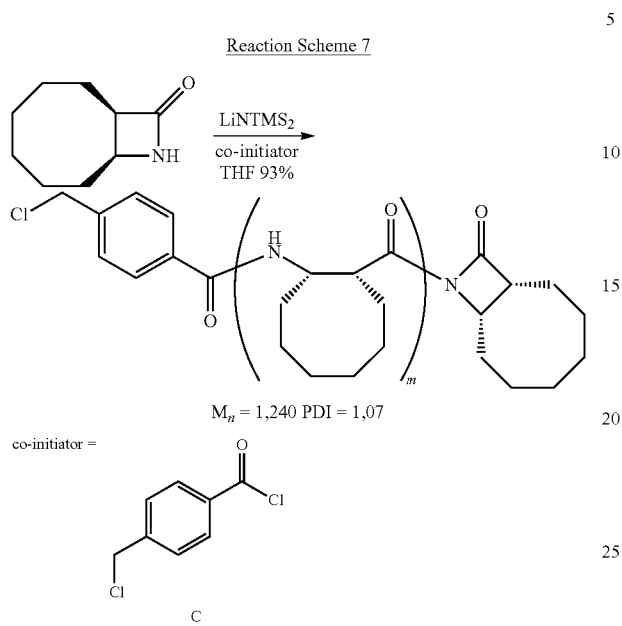
Reaction Scheme 7
$M_n = 1,240$ PDI = 1,07
Further chemical modification of the 4-chloromethyl end-group yielded a host of end-group functionalized β-polypeptide polymer derivatives as shown in Reaction Scheme 8:

Reaction Scheme 8
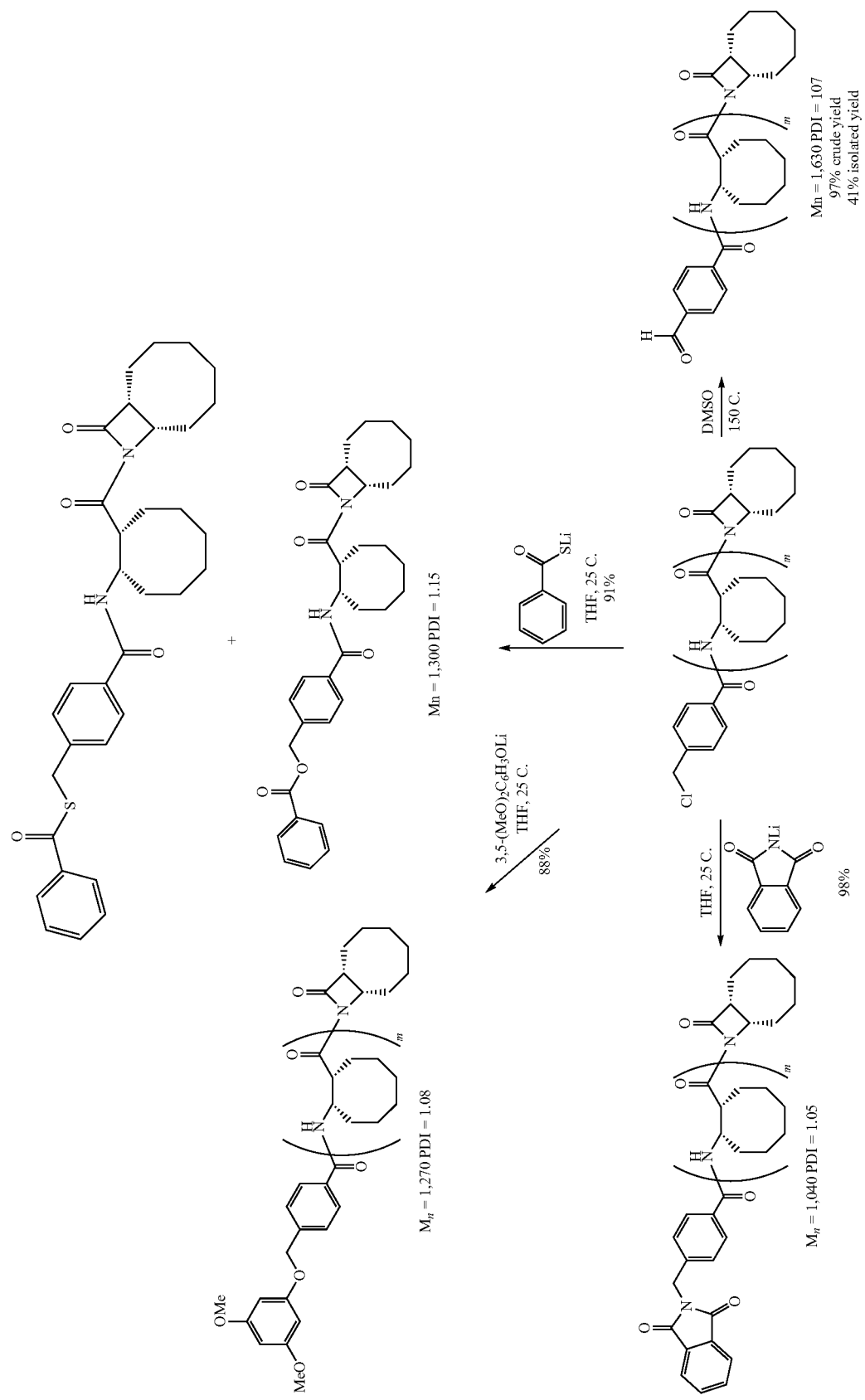

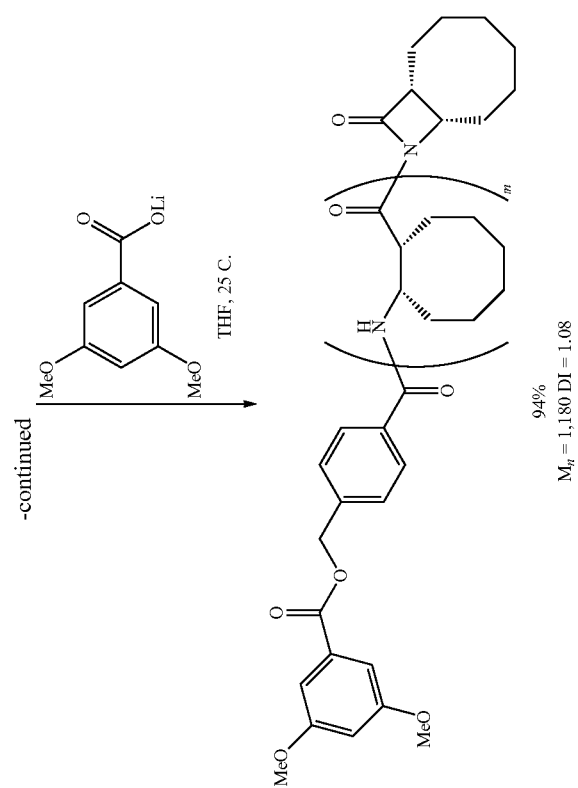

As shown in Reaction Scheme 8, the reactive 4-chloromethyl group can be used to append various functional end groups in high yields, such as aldehyde, esters, thioesters, amines and imides (phthalimide followed by deprotection), and the like.

An α,β-unsaturated carbonyl terminus can be appended to the polymer chain by running the reaction using an appropriate co-initiator, as shown in Reaction Scheme 9:

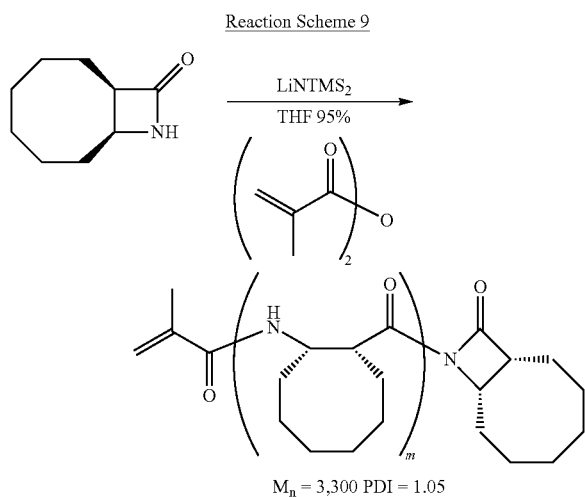

REFERENCES (1) Creuwels, L.; vanGolde, L. M. G.; Haagsman, H. P. *Lung* 1997. 175, 1-39.
(2) Notter, R. H. *Lung Surfactants: Basic Science and Clinical Applications*; Marcel Dekker. New York, 2000.
(3) Orgeig, S.; Bernhard, W.; Biswas, S. C.; Daniels, C. B.; Hall, S. B.; Hetz, S. K.; Lang, C. J.; Maim., J. N.; Panda, A. K.; Perez-Gil, J.; Possmayer, F.; Veldhuizen, R. A.; Yan, W. *Integr. Comp. Biol.* 2007, 47, 610-627.
(4) Mingarro, I.; Lukovic, D.; Vilar, M.; Perez-Gil. J. *Curr. Med. Chem.* 2008, 15, 393-403.
(5) Avery, M. E.; Mead, J. *Am. J. Dis. Child.* 1959, 97, 517-523.
(6) Pison, U.; Seeger, W.; Buchhorn, R.; Joka, T.; Brand, M.; Obertacke, U.; Neuhof, H.; Schmit-Nauerburg, K. P. *Am. Rev. Respir. Dis.* 1989, 140, 1033-1039.
(7) Lewis, J. E.; Jobe, A. H. *Am. Rev. Respir. Dis.* 1993, 147, 218-233.
(8) Moya, F.; Maturana, A. *Clin. Perinatol.* 2007, 34, 145-177.
(9) Hawgood, S.; Schiffer, K. *Annu. Rev. Physiol.* 1991, 53, 375-394.
(10) Vandenbussche, G.; Clercx, A.; Clercx, M.; Curstedt, T.; Johansson, J.; Jornvall, H.; Ruysschaert, J. M. *Biochemistry* 1992, 31, 9169-9176.
(11) Beck, D. C.; Ikegami, M.; Na, C. L.; Zaltash, S.; Johansson, J.; Whitsett, J. A.; Weaver, T. E. *J. Biol. Chem.* 2000, 275, 3365-3370.
(12) Haagsman, H. P.; Diemel, R. V. *Comp. Biochem. Physiol. A. Mol. Integr. Physiol.* 2001, 129, 91-108.
(13) Johansson, J.; Szyperski, T.; Curstedt, T.; Wuthrich, K. *Biochemistry* 1994, 33.
(14) Johansson, J.; Curstedt, T.; Robertson, B. *Eur. Respir. J.* 1994, 7, 372-391.
(15) Creuwels, L. A.; Boer, E. H.; Demel, R. A.; van Golde, L. M. G.; Haagsman, H. P. *J. Biol. Chem.* 1995, 270, 16225-16229.
(16) Kramer, A.; Wintergalen, A.; Sieber, M.; Galla, H. J.; Amrein, M.; Guckenberger, R. *Biophys. J.* 2000, 78, 458-465.
(17) Bi, X. H.; Flach, C. R.; Perez-Gil, J.; Plasencia, I.; Andreu, D.; Oliveira, E.; Mendelsohn, R. *Biochemistry* 2002, 41, 8385-8395.
(18) Perez-Gil, J. *Biochim. Biophys. Acta* 2008, 1778, 1676-1695.
(19) Wu, C. W.; Seurynck, S. L.; Lee, K. Y. C.; Barron, A. E. *Chem. Biol.* 2003, 10, 1057-1063.
(20) Seurynck, S. L.; Patch, J. A.; Barron, A. E. *Chem. Biol.* 2005, 12, 77-88.
(21) Seurynck-Servoss, S. L.; Dohm, M. T.; Barron, A. E. *Biochemistry* 2006, 45, 11809-11818.
(22) Seurynck-Servoss, S. L.; Brown, N. J.; Dohm, M. T.; Wu, C. W.; Barron, A. E. *Coll. Surf B. Biointerfaces* 2007, 57, 37-55.
(23) Brown, N. J.; Wu, C. W.; Seurynck-Servoss, S. L.; Barron, A. E. *Biochemistry* 2008, 47, 1808-1818.
(24) Dohm, M. T.; Seurynck-Servoss, S. L.; Seo, J.; Zuckermann, R. N.; Barron, A. E. *Biopolymers Peptide Science* 2009, in press.
(25) Hawgood, S.: Ogawa, A.; Yukitake, K.; Schlueter, M.; Brown. C.; White, T.; Buckley, D.; Lesikar, D.; Benson, B. J. *Am. J. Respir. Crit. Care Med.* 1996, 154, 484-490.
(26) Waring, A.; Taeusch, H. W.; Bruni, R.; Amirkhanian, J. D.; Fan, B. R.; Stevens, R.; Young, J. *Pept. Res.* 1989, 2, 308-313.
(27) Bruni, R.; Taeusch, H. W.; Waring, A. J. *Proc. Natl. Acad. Sci. U.S.A.* 1991, 88, 7451-7455.
(28) Veldhuizen, E. J. A.; Waring, A. J.; Walther, F. J.; Batenburg, J. J.; van Golde, L. M. G.; Haagsman, H. P. *Biophys. J.* 2000, 79, 377-384.
(29) Waring, A. J.; Walther, F.; Gordon, L. M.; Hemandez-Juviel, J.; Hong, T.; Sherman, M. A.; Alonso, C.; Alig, T.; Brauner, J. W.; Bacon, D.; Zasadzinski, J. *J. Pept. Res.* 2005, 66, 364-374.
(30) Dohm, M. T.; Brown, N. J.; Seurynck-Servoss, S. L.; Bernardino de la Sema, J.; Barron, A. E. submitted 2009.
(31) Kirshenbaum, K.; Barron, A. E.; Goldsmith, R. A.; Armand, P.; Bradley, E. K.; Truong, K. T. V.; Dill, K. A.; Cohen, F. E.; Zuckermann, R. N. *Proc. Natl. Acad Sci. U.S.A.* 1998, 95, 4303-4308.
(32) Appella, D. 1-1.; Christianson, L. A.; Katie, I. L.; Powell, D. R.; Gellman, S. H. *J. Am. Chem. Soc.* 1996, 118, 13071-13072.
(33) Cheng, R. P.; Gellman, S. H.; DeGrado, W. F. *Chem. Rev.* 2001, 101, 3219-3232.
(34) Hayen, A.; Schmitt, M. A.; Ngassa, F.; Thomasson, K. A.; Gellman, S. H. *Angew. Chem. Int. Ed.* 2004, 43, 505-510.
(35) Home, W. S.; Gellman, S. H. *Acc. Chem. Res.* 2008, 41, 1399-1408.
(36) Zuckermann, R. N.; Kerr, J. M.; Kent, S. B. H.; Moos, W. H. *J. Am. Chem. Soc.* 1992, 114, 10646-10647.
(37) Gelman, M. A.; Lynn, D. M.; Weisblum, B.; Gellman, S. H. *Org. Len.* 2004, 6, 557-60.
(38) Schmitt, M. A.; Weisblum, B.; Gellman, S. H. *J. Am. Chem. Soc.* 2007, 129, 417-428.
(39) Shai. Y. *Biochim. Biophys. Acta* 1999, 1462, 55-70.
(40) Mowery, B. P.; Lee, S. E.; Kissounko, D. A.; Epand, R. F.; Epand, R. M.; Weisblum, B.; Stahl, S. S.; Gellman, S. H. *J. Am. Chem. Soc.* 2007, 129, 15474-15476.

(41) Epand, R. F.; Mowery, B. P.; Lee, S. E.; Stahl, S. S.; Lehrer, R. I.; Gellman, S. H. *J. Mol. Biol.* 2008, 379, 38-50.
(42) Mowery. B. P.: Lindner, A. H.; Weisibum, B.; Stahl, S. S.; Gellman, S. H. *J. Am. Chem. Soc.* 2009, 131, 9735-9745.
(43) Putz. G.; Goerke, J.; Taeusch, H. W.; Clements, J. A. *J. Appl. Physiol.* 1994, 76, 1425-1431.
(44) Seurynck, S. L.; Brown, N. J.; Wu, C. W.; Germino, K. W.; Kohlmeir, E. K.; Ingenito, E. P.; Glucksberg, M. R.; Barron, A. E.; Johnson, M. *J. Appl. Physiol.* 2005, 99, 624-633.
(45) Tanaka, Y.; Takei, T.; Aiba, T.; Masuda, K.; Kiuchi, A.; Fujiwara, T. *J. Lipid Res.* 1986, 27, 475-485.
(46) Mang, J.; Kissounko, D. A.; Lee, S. E.: Gellman, S. H.; Stahl, S. S. *J. Am. Chem. Soc.* 2009, 131, 1589-1597.
(47) Ryan, M. A.; Qi, X.; Serrano, A. G.; Ikegami, M.; Perez-Gil, J.; Johansson, J.; Weaver, T. E. *Biochemistry* 2005, 44, 861-872.
(48) Serrano, A. G.; Ryan, M. A.; Weaver, T. E.; Perez-Gil, J. *Biophys. J.* 2006, 90, 238-249.
(49) Wang, Y. D.; Rao, K. M. K.; Demchuk, E. *Biochemistry* 2003, 42, 4015-4027.
(50) Brown, N. J.; Bernardino de la Sema, J.; Barron, A. E. submitted 2009.
(51) Hashimoto, K. *Prog. Polym. Sci.* 2000, 25, 1411-1462.
(52) Cheng, J. J.; Deming, T. J. *J. Am. Chem. Soc.* 2001, 123, 9457-9458.
(53) Cochrane, C. G.; Revak, S. D. *Science* 1991, 254, 566-568.
(54) Nadolski, M. J.; Linder, M. E. *FEBS J.* 2007, 274, 5202-5210.
(55) Chu-Kung, A. F.; Bozzelli, K. N.; Lockwood, N. A.; Haseman, J. R.; Mayo, K. H.; Tirrell, M. *Bioconj. Chem.* 2004, 15, 530-535.
(56) Bringezu, F.; Ding, J. Q.; Brezesinski, G.; Zasadzinski, J. A. *Langmuir* 2001, 17, 4641-4648.
(57) Bernardino de la Serna, J.; Perez-Gil, J.; Simonsen, A. C.; Bagatolli, L. A. *J. Biol. Chem.* 2004, 279, 40715-40722.
(58) Schurch, S.; Qanbar, R.; Bachofen, H.; Possmayer, F. *Biol. Neonate* 1995, 67, 61-76.
(59) Veldhuizen, E. J. A.; Haagsman, H. P. *Biochim. Biophys. Acta* 2000, 1467, 255-270.
(60) Ryan, M. A.; Akinbi, H. T.; Serrano, A. G.; Perez-Gil, J.; Wu, H. X.; McCormack, F. X.; Weaver, T. E. *J. Immunol.* 2006, 176, 416-425.
(61) Andersson. M.; Curstedt, T.; Jomvall, H.; Johansson, J. *FEBS Lett.* 1995, 362, 328-332.
(62) Merrifield, R. B. *J. Am. Chem. Soc.* 1963. 85, 2149-2154.

What is claimed is:

1. A method of treating infant, acute, or adult respiratory distress syndromes, and pulmonary disorders involving deficient or dysfunctional lung surfactant in mammals, the method comprising:
administering to a mammalian subject in need thereof an artificial lung surfactant composition comprising a nylon-3 homopolymer or nylon-3 copolymer as an artificial lung surfactant present in the artificial lung surfactant composition in an amount effective to treat a respiratory distress syndrome or pulmonary disorder involving deficient or dysfunctional lung surfactant in the mammalian subject, wherein monomers of the nylon-3 homopolymer or nylon-3 copolymer are selected from the group consisting of:

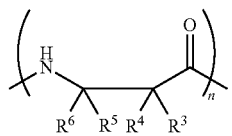

wherein:
$R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl; or
one of $R^3$ and $R^4$ combined with one of $R^5$ and $R^6$, together with the carbon atoms to which they are attached, define a cyclic moiety "A"

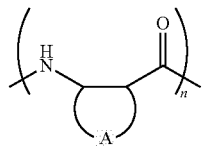

wherein "A" is selected from the group consisting of substituted or unsubstituted $C_5$-$C_{12}$ cycloalkyl, $C_5$-$C_{12}$ cycloalkenyl, and five- to twelve-membered heterocyclic;
provided that at least two of $R^3$, $R^4$, $R^5$, or $R^6$ are not hydrogen; and
wherein "n" is a positive integer.

2. The method of claim 1, wherein the nylon-3 homopolymer or nylon-3 copolymer is a nylon-3 random copolymer.

3. The method of claim 1, wherein the nylon-3 homopolymer or nylon-3 copolymer is a nylon-3 non-random copolymer.

4. The method of claim 1, wherein the nylon-3 homopolymer or nylon-3 copolymer is a nylon-3 block copolymer.

5. The method of claim 1, which is a method treating infant, acute, or adult respiratory distress syndromes.

6. The method of claim 1, wherein:
one of $R^3$ and $R^4$ combined with one of $R^5$ and $R^6$, together with the carbon atoms to which they are attached, define a cyclic moiety "A"

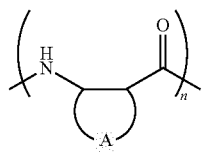

wherein "A" is selected from the group consisting of substituted or unsubstituted $C_5$-$C_{12}$ cycloalkyl, $C_5$-$C_{12}$ cycloalkenyl, and five- to twelve-membered heterocyclic; and
the other of $R^3$ and $R^4$ and the other of $R^5$ and $R^6$ are independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, and protected-amino-$C_1$-$C_6$-alkyl.

7. The method of claim 6, wherein "A" is substituted or unsubstituted $C_5$-$C_{12}$ cycloalkyl.

8. The method of claim 6, wherein "A" is substituted or unsubstituted $C_5$-$C_{12}$ cycloalkenyl.

9. The method of claim 6, wherein "A" is substituted or unsubstituted five- to twelve-membered heterocyclic.

10. The method of claim 6, wherein the other of $R^3$ and $R^4$ and the other of $R^5$ and $R^6$ are independently selected from the group consisting of substituted or unsubstituted $C_1$-$C_6$-alkyl, aryl, and $C_1$-$C_6$-alklyaryl.

11. The method of claim 6, wherein the other of $R^3$ and $R^4$ and the other of $R^5$ and $R^6$ are independently selected from the group consisting of substituted or unsubstituted amino, protected-amino, amino-$C_1$-$C_6$-alkyl, and protected-amino-$C_1$-$C_6$-alkyl.

12. The method of claim 6, wherein the nylon-3 homopolymer or the nylon-3 copolymer is a nylon-3 random copolymer.

13. The method of claim 6, wherein the nylon-3 homopolymer or the nylon-3 copolymer is a nylon-3 non-random copolymer.

14. The method of claim 6, wherein the nylon-3 homopolymer or the nylon-3 copolymer is a nylon-3 block copolymer.

15. The method of claim 6, which is a method treating infant, acute, or adult respiratory distress syndromes.

\* \* \* \* \*